United States Patent
Tompkins

(10) Patent No.: US 9,784,722 B2
(45) Date of Patent: *Oct. 10, 2017

(54) SYSTEMS AND METHODS FOR EVALUATION OF WINE CHARACTERISTICS

(71) Applicant: VineSleuth, Inc., Spring, TX (US)

(72) Inventor: Michael J. Tompkins, San Francisco, CA (US)

(73) Assignee: VineSleuth, Inc., Spring, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/271,964

(22) Filed: Sep. 21, 2016

(65) Prior Publication Data

US 2017/0010247 A1  Jan. 12, 2017

Related U.S. Application Data

(63) Continuation of application No. 14/454,689, filed on Aug. 7, 2014, now Pat. No. 9,494,566.

(Continued)

(51) Int. Cl.
*G06F 7/00* (2006.01)
*G06F 17/30* (2006.01)
(Continued)

(52) U.S. Cl.
CPC ....... *G01N 33/146* (2013.01); *G01N 33/0001* (2013.01); *G06F 17/3053* (2013.01); *G06F 17/30867* (2013.01); *G06F 17/30876* (2013.01)

(58) Field of Classification Search
None
See application file for complete search history.

(56) References Cited

U.S. PATENT DOCUMENTS 5,200,909 A 4/1993 Juergens
6,606,624 B1 8/2003 Goldberg
(Continued)

OTHER PUBLICATIONS

Smith, Lindsey I., "A Tutorial on Principal Component Analysis," University of Otago, Feb. 26, 2002 [retrieved from the Internet at http://www.cs.otago.ac. nz/cosc453/student_ tutorials/principal_ components.pdf on Mar. 24, 2016].

(Continued)

*Primary Examiner* — Tuan A Pham
(74) *Attorney, Agent, or Firm* — Sheppard, Mullin, Richter & Hampton LLP

(57) ABSTRACT

A method comprises: receiving wine evaluations of wines from wine panelists, each wine evaluation including intensity values describing a plurality of wine characteristics for each of a set of wines, each wine evaluation generated by a wine panelist; generating a global intensity value from particular intensity values describing a particular wine characteristic of a particular wine, the particular intensity values being from the wine evaluations; comparing a selected intensity value generated by a selected wine panelist describing the particular wine characteristic for the particular wine against the global intensity value to determine an accuracy deviation; comparing the accuracy deviation against an accuracy deviation threshold to determine whether the selected intensity value is deemed inaccurate based on the comparison; updating the global intensity value for the particular wine characteristic for the particular wine based on the accuracy determination; and storing the updated global intensity value in a wine database.

12 Claims, 62 Drawing Sheets
(29 of 62 Drawing Sheet(s) Filed in Color)

Related U.S. Application Data

(60) Provisional application No. 61/863,364, filed on Aug. 7, 2013.

(51) Int. Cl.
  *G01N 33/14* (2006.01)
  *G01N 33/00* (2006.01)

(56) References Cited

U.S. PATENT DOCUMENTS

| | | |
|---|---|---|
| 7,194,458 B1 | 3/2007 | Micaelian et al. |
| 7,461,055 B2 | 12/2008 | Atcheson et al. |
| 7,587,331 B2 | 9/2009 | Pelletier |
| 7,878,390 B1 | 2/2011 | Batten et al. |
| 7,881,960 B2 | 2/2011 | Ramamurti |
| 7,917,503 B2 | 3/2011 | Mowatt et al. |
| 8,364,545 B2 | 1/2013 | Arsenault |
| 2005/0210025 A1 | 9/2005 | Dalton et al. |
| 2006/0085292 A1* | 4/2006 | Lafay .............. G06Q 10/103 705/301 |
| 2007/0104832 A1 | 5/2007 | Tomlinson |
| 2007/0106651 A1 | 5/2007 | Isaacson et al. |
| 2007/0179837 A1 | 8/2007 | Finley et al. |
| 2007/0282696 A1 | 12/2007 | Strodtman |
| 2008/0275761 A1 | 11/2008 | Seifer et al. |
| 2009/0043640 A1 | 2/2009 | Sutton |
| 2009/0144272 A1 | 6/2009 | Adarsh et al. |
| 2009/0157486 A1* | 6/2009 | Gross .............. G06Q 30/02 705/319 |
| 2009/0187550 A1 | 7/2009 | Mowatt et al. |
| 2009/0210321 A1 | 8/2009 | Rapp |
| 2010/0312650 A1 | 12/2010 | Pinckney et al. |
| 2011/0054968 A1 | 3/2011 | Galaviz |
| 2011/0063468 A1 | 3/2011 | Ahn et al. |
| 2011/0202423 A1 | 8/2011 | Pratt et al. |
| 2013/0339348 A1* | 12/2013 | Pickelsimer ....... G06Q 30/0631 707/723 |

OTHER PUBLICATIONS

Wikimedia Foundation Inc., "Multidimensional Scaling," Wikipedia online encyclopedia entry, Jun. 27, 2011 [retrieved rom the Internet at https://en.wikipedia.org/w/index.php?title=Multidimensional_scaling&oldid=436486301 on Mar. 4, 2016].

Wikimedia Foundation Inc., "Principal Component Analysis," Wikipedia online encyclopedia entry, Jul. 26, 2011 [retrieved from the Internet at https://en.wikipedia.org/w/index.php?title=Principal_component_analysis&oldid=441474173> on Mar. 4, 2016].

European Patent Application No. 12837132.5, Search Report mailed May 21, 2015.

International Application No. PCT/US2012/057336, International Search Report and Written Opinion mailed Nov. 30, 2012.

European Patent Application No. 12837132.5, Examination Report dated Apr. 21, 2017.

* cited by examiner

| Vintage | Wine Country | Wine Region | Wine Appellation | Wine Varietal | Wine Producer | Fruit | Earth | Spice | Resin |
|---|---|---|---|---|---|---|---|---|---|
| 2005 | USA | Napa Valley | Howell Mountain | Cabernet | Example Wine Co. | 0.5 | 2.5 | 2.0 | 3.5 |

FIG. 3

Difference between Scores by Panel Group (2-4 vs. 5-6), Red Wines

| Descriptor | Panels 2-4 Avg | Panels 5-6 Avg | p Value |
|---|---|---|---|
| Aroma Intensity | 0.682 | 0.573 | 0.001 |
| Dried Fruits Jam | 0.960 | 0.808 | 0.000 |
| Berries | 0.746 | 0.629 | 0.001 |
| Citrus | 0.160 | 0.087 | 0.000 |
| Tropical Fruits Melon | 0.091 | 0.091 | 0.979 |
| Tree Fruits | 0.180 | 0.110 | 0.000 |
| Native Grapy | 0.062 | 0.054 | 0.734 |
| Candied Fruit | 0.445 | 0.347 | 0.001 |
| Floral | 0.578 | 0.460 | 0.000 |
| Green Notes | 0.717 | 0.610 | 0.035 |
| Hay Straw | 0.230 | 0.165 | 0.006 |
| Sweet aromas | 0.776 | 0.573 | 0.000 |
| Baking Spices | 0.726 | 0.600 | 0.000 |
| Pepper | 0.552 | 0.442 | 0.034 |
| Earthy | 0.782 | 0.541 | 0.000 |
| Beef | 0.304 | 0.237 | 0.014 |
| Woody | 0.742 | 0.643 | 0.011 |
| Lees Butter | 0.257 | 0.150 | 0.000 |
| Petrol | 0.208 | 0.183 | 0.644 |
| Mineral | 0.394 | 0.305 | 0.002 |
| Flavor Intensity | 0.613 | 0.479 | 0.000 |
| Texture | 0.817 | 0.534 | 0.000 |
| Palate Weight | 0.614 | 0.413 | 0.000 |
| Length of Finish | 0.688 | 0.463 | 0.000 |
| Acidity | 0.552 | 0.398 | 0.000 |
| Perceived Sugar | 0.401 | 0.207 | 0.000 |
| Alcohol | 0.518 | 0.363 | 0.000 |

FIG. 16

Difference between Scores by Panel Group (2-4 vs. 5-6), White Wines

| Descriptor | Panels 2-4 Avg | Panels 5-6 Avg | p Value |
|---|---|---|---|
| Aroma Intensity | 0.730 | 0.730 | 0.628 |
| Dried Fruits Jam | 0.434 | 0.363 | 0.238 |
| Berries | 0.174 | 0.097 | 0.069 |
| Citrus | 0.859 | 0.667 | 0.033 |
| Tropical Fruits Melon | 0.964 | 0.778 | 0.048 |
| Tree Fruits | 0.927 | 0.754 | 0.046 |
| Native Grapy | 0.178 | 0.040 | 0.011 |
| Candied Fruit | 0.535 | 0.314 | 0.000 |
| Floral | 0.702 | 0.587 | 0.066 |
| Green Notes | 0.634 | 0.535 | 0.208 |
| Hay Straw | 0.483 | 0.357 | 0.086 |
| Sweet aromas | 0.647 | 0.504 | 0.039 |
| Baking Spices | 0.443 | 0.444 | 0.514 |
| Pepper | 0.300 | 0.300 | 0.697 |
| Earthy | 0.390 | 0.159 | 0.035 |
| Brett | 0.009 | 0.016 | 0.912 |
| Woody | 0.458 | 0.437 | 0.717 |
| Lees Butter | 0.474 | 0.356 | 0.072 |
| Petrol | 0.509 | 0.286 | 0.000 |
| Mineral | 0.702 | 0.429 | 0.000 |
| Flavor Intensity | 0.728 | 0.571 | 0.028 |
| Texture | 0.682 | 0.556 | 0.114 |
| Palate Weight | 0.618 | 0.476 | 0.025 |
| Length of Finish | 0.705 | 0.552 | 0.040 |
| Acidity | 0.704 | 0.516 | 0.011 |
| Perceived Sugar | 0.632 | 0.333 | 0.000 |
| Alcohol | 0.546 | 0.413 | 0.023 |

FIG. 17

Difference between Scores by Panel Group (3-4 vs. 5-6), Red Wines

| Descriptor | Panels 3-4 Avg | Panels 5-6 Avg | p Value |
|---|---|---|---|
| Aroma Intensity | 0.697 | 0.573 | 0.004 |
| Dried Fruits Jam | 0.834 | 0.668 | 0.021 |
| Berries | 0.759 | 0.629 | 0.009 |
| Citrus | 0.139 | 0.087 | 0.000 |
| Tropical Fruits Melon | 0.119 | 0.091 | 0.132 |
| Tree Fruits | 0.197 | 0.119 | 0.002 |
| Native Grapy | 0.034 | 0.054 | 0.514 |
| Candied Fruit | 0.461 | 0.347 | 0.002 |
| Floral | 0.506 | 0.460 | 0.193 |
| Green Notes | 0.669 | 0.610 | 0.241 |
| Hay Straw | 0.266 | 0.165 | 0.003 |
| Sweet aromas | 0.722 | 0.573 | 0.004 |
| Baking Spices | 0.669 | 0.600 | 0.094 |
| Pepper | 0.455 | 0.447 | 0.802 |
| Earthy | 0.706 | 0.541 | 0.001 |
| Brett | 0.275 | 0.237 | 0.176 |
| Woody | 0.670 | 0.643 | 0.388 |
| Lees Butter | 0.301 | 0.159 | 0.000 |
| Petrol | 0.291 | 0.183 | 0.009 |
| Mineral | 0.309 | 0.205 | 0.070 |
| Flavor Intensity | 0.506 | 0.479 | 0.585 |
| Texture | 0.653 | 0.534 | 0.035 |
| Palate Weight | 0.547 | 0.413 | 0.000 |
| Length of Finish | 0.581 | 0.462 | 0.018 |
| Acidity | 0.456 | 0.398 | 0.098 |
| Perceived Sugar | 0.309 | 0.207 | 0.000 |
| Alcohol | 0.463 | 0.363 | 0.002 |

FIG. 18

Difference between Scores by Panel Group (3-4 vs. 5-6), White Wines

| Descriptor | Panels 3-4 Avg | Panels 5-6 Avg | p Value |
|---|---|---|---|
| Aroma Intensity | 0.668 | 0.730 | 0.907 |
| Dried Fruits Jam | 0.407 | 0.363 | 0.301 |
| Berries | 0.189 | 0.097 | 0.141 |
| Citrus | 0.684 | 0.667 | 0.846 |
| Tropical Fruits Melon | 0.889 | 0.778 | 0.410 |
| Tree Fruits | 0.821 | 0.754 | 0.359 |
| Native Grapy | 0.053 | 0.040 | 0.912 |
| Candied Fruit | 0.319 | 0.214 | 0.000 |
| Floral | 0.568 | 0.587 | 0.978 |
| Green Notes | 0.589 | 0.532 | 0.434 |
| Hay Straw | 0.423 | 0.357 | 0.243 |
| Sweet aromas | 0.637 | 0.504 | 0.115 |
| Baking Spices | 0.516 | 0.444 | 0.458 |
| Pepper | 0.143 | 0.206 | 0.581 |
| Earthy | 0.368 | 0.159 | 0.002 |
| Brett | 0.016 | 0.016 | 0.819 |
| Woody | 0.511 | 0.437 | 0.464 |
| Lees Butter | 0.489 | 0.356 | 0.190 |
| Petrol | 0.479 | 0.286 | 0.004 |
| Mineral | 0.421 | 0.429 | 0.980 |
| Flavor Intensity | 0.537 | 0.571 | 0.691 |
| Texture | 0.547 | 0.356 | 0.010 |
| Palate Weight | 0.616 | 0.476 | 0.088 |
| Length of Finish | 0.553 | 0.552 | 0.981 |
| Acidity | 0.579 | 0.516 | 0.322 |
| Perceived Sugar | 0.532 | 0.333 | 0.004 |
| Alcohol | 0.500 | 0.413 | 0.216 |

FIG. 19

Difference between Scores by Number of Wines per Flight, Red Wines

| Descriptor | N Wines=5 | N Wines=6 | N Wines=7 | N Wines=8 | N Wines=9 | P value |
|---|---|---|---|---|---|---|
| Aroma Intensity | 0.565 | 0.677 | 0.400 | 0.343 | 0.786 | 0.023 |
| Dried Fruits Jam | 0.682 | 0.699 | 0.557 | 0.543 | 0.786 | 0.564 |
| Berries | 0.641 | 0.632 | 0.600 | 0.457 | 0.786 | 0.580 |
| Citrus | 0.076 | 0.123 | 0.029 | 0.290 | 0.071 | 0.029 |
| Tropical Fruits Melon | 0.076 | 0.105 | 0.100 | 0.229 | 0.071 | 0.206 |
| Tree Fruits | 0.094 | 0.182 | 0.129 | 0.143 | 0.214 | 0.145 |
| Native Grapy | 0.047 | 0.075 | 0.086 | 0.029 | 0.000 | 0.661 |
| Candied Fruit | 0.328 | 0.439 | 0.371 | 0.343 | 0.571 | 0.202 |
| Floral | 0.460 | 0.474 | 0.514 | 0.314 | 0.429 | 0.534 |
| Green Notes | 0.603 | 0.606 | 0.657 | 0.600 | 0.571 | 0.853 |
| Hay Straw | 0.170 | 0.144 | 0.143 | 0.257 | 0.071 | 0.347 |
| Sweet aromas | 0.560 | 0.684 | 0.544 | 0.457 | 0.357 | 0.298 |
| Baking Spices | 0.396 | 0.386 | 0.700 | 0.600 | 0.357 | 0.635 |
| Pepper | 0.448 | 0.443 | 0.357 | 0.514 | 0.714 | 0.383 |
| Earthy | 0.358 | 0.541 | 0.435 | 0.486 | 0.643 | 0.705 |
| Brett | 0.094 | 0.133 | 0.100 | 0.143 | 0.143 | 0.003 |
| Woody | 0.652 | 0.699 | 0.551 | 0.486 | 0.643 | 0.421 |
| Lees Butter | 0.163 | 0.158 | 0.116 | 0.114 | 0.357 | 0.505 |
| Petrol | 0.200 | 0.158 | 0.186 | 0.143 | 0.000 | 0.332 |
| Mineral | 0.306 | 0.348 | 0.114 | 0.171 | 0.286 | 0.373 |
| Flavor Intensity | 0.482 | 0.474 | 0.439 | 0.429 | 0.786 | 0.230 |
| Texture | 0.537 | 0.544 | 0.529 | 0.600 | 0.308 | 0.804 |
| Palate Weight | 0.422 | 0.447 | 0.400 | 0.286 | 0.214 | 0.247 |
| Length of Finish | 0.470 | 0.466 | 0.486 | 0.486 | 0.590 | 0.913 |
| Acidity | 0.403 | 0.406 | 0.300 | 0.343 | 0.786 | 0.045 |
| Perceived Sugar | 0.156 | 0.246 | 0.257 | 0.229 | 0.429 | 0.043 |
| Alcohol | 0.357 | 0.376 | 0.400 | 0.343 | 0.286 | 0.940 |

FIG. 20

Difference between Scores by Number of Wines per Flight, White Wines

| Descriptor | N Wines=5 | N Wines=7 | N Wines=8 | N Wines=9 | P value |
|---|---|---|---|---|---|
| Aroma Intensity | 0.651 | 0.762 | 0.657 | 1.714 | 0.086 |
| Dried Fruits/Jam | 0.349 | 0.381 | 0.394 | 0.286 | 0.861 |
| Berries | 0.048 | 0.190 | 0.091 | 0.286 | 0.232 |
| Citrus | 0.521 | 0.524 | 0.886 | 0.857 | 0.328 |
| Tropical Fruits/Melon | 0.746 | 1.095 | 0.743 | 0.286 | 0.105 |
| Tree Fruits | 0.730 | 0.714 | 0.800 | 0.857 | 0.894 |
| Native Grapy | 0.016 | 0.048 | 0.029 | 0.286 | 0.007 |
| Candied Fruit | 0.333 | 0.095 | 0.200 | 0.429 | 0.609 |
| Floral | 0.587 | 0.667 | 0.514 | 0.714 | 0.730 |
| Green Notes | 0.556 | 0.381 | 0.571 | 0.571 | 0.431 |
| Hay/Straw | 0.302 | 0.571 | 0.343 | 0.286 | 0.362 |
| Sweet aromas | 0.397 | 0.429 | 0.514 | 0.857 | 0.280 |
| Baking Spices | 0.444 | 0.524 | 0.371 | 0.571 | 0.633 |
| Pepper | 0.079 | 0.190 | 0.429 | 0.286 | 0.077 |
| Earthy | 0.222 | 0.143 | 0.086 | 0.000 | 0.266 |
| Brett | 0.032 | 0.000 | 0.000 | 0.000 | 0.801 |
| Woody | 0.540 | 0.571 | 0.229 | 0.143 | 0.045 |
| Lees/Butter | 0.508 | 0.762 | 0.514 | 0.571 | 0.646 |
| Petrol | 0.270 | 0.524 | 0.200 | 0.143 | 0.266 |
| Mineral | 0.413 | 0.286 | 0.514 | 0.571 | 0.431 |
| Flavor Intensity | 0.429 | 0.762 | 0.686 | 0.714 | 0.050 |
| Texture | 0.524 | 0.619 | 0.571 | 0.571 | 0.872 |
| Palate Weight | 0.508 | 0.476 | 0.400 | 0.571 | 0.636 |
| Length of Finish | 0.540 | 0.714 | 0.471 | 0.571 | 0.338 |
| Acidity | 0.460 | 0.667 | 0.486 | 0.714 | 0.511 |
| Perceived Sugar | 0.383 | 0.476 | 0.143 | 0.857 | 0.010 |
| Alcohol | 0.413 | 0.667 | 0.386 | 0.286 | 0.078 |

2-way ANOVA Results for Wines, within each Varietal

| | Zinfandel | Cabernet Sauvignon | Chardonnay | Sauvignon Blanc |
|---|---|---|---|---|
| Aroma Intensity | 0.0002 | 0.0002 | 0.0000 | 0.0000 |
| Dried Fruits Jam | 0.0002 | 0.0307 | 0.0006 | 0.0003 |
| Berries | 0.0004 | 0.0308 | 0.3647 | 0.3488 |
| Citrus | 0.4483 | 0.0371 | 0.0035 | 0.0000 |
| Tropical Fruits Melon | 0.1653 | 0.0710 | 0.1387 | 0.0174 |
| Tree Fruits | 0.0002 | 0.0002 | 0.1093 | 0.3568 |
| Native Grape | #N/A | 0.2333 | 0.8442 | 0.0820 |
| Candied Fruit | 0.8191 | 0.3976 | 0.0012 | 0.0733 |
| Floral | 0.1479 | 0.0023 | 0.0390 | 0.0420 |
| Green Notes | 0.7333 | 0.0000 | 0.0006 | 0.0000 |
| Hay Straw | 0.0306 | 0.0171 | 0.0801 | 0.3189 |
| Sweet aromas | 0.0000 | 0.0010 | 0.0000 | 0.0001 |
| Baking Spices | 0.0011 | 0.0233 | 0.0000 | 0.0098 |
| Pepper | 0.0661 | 0.1400 | 0.3139 | 0.0000 |
| Earthy | 0.0046 | 0.0012 | 0.0000 | 0.0756 |
| Burnt | 0.5858 | 0.5020 | 0.3187 | #N/A |
| Woody | 0.0000 | 0.0000 | 0.0000 | 0.0404 |
| Lees Butter | 0.4684 | 0.0277 | 0.0000 | 0.0002 |
| Petrol | 0.9010 | 0.4799 | 0.0001 | 0.3879 |
| Mineral | 0.4473 | 0.0010 | 0.0000 | 0.0003 |
| Flavor Intensity | 0.0000 | 0.2834 | 0.0000 | 0.0000 |
| Texture | 0.0193 | 0.0622 | 0.0021 | 0.0030 |
| Palate Weight | 0.0025 | 0.0085 | 0.0000 | 0.1031 |
| Length of Finish | 0.0003 | 0.0141 | 0.0000 | 0.0000 |
| Acidity | 0.0187 | 0.4344 | 0.0000 | 0.0000 |
| Perceived Sugar | 0.0000 | 0.0177 | 0.0000 | 0.0001 |
| Alcohol | 0.0000 | 0.0003 | 0.0000 | 0.0029 |

FIG. 23

Principal Component Analysis: Full Dataset

| | Component | | | | | |
|---|---|---|---|---|---|---|
| | 1 | 2 | 3 | 4 | 5 | 6 |
| Tree Fruits | 0.880 | | | | | |
| Citrus | 0.856 | | | | | |
| Tropical Fruits Melon | 0.849 | | | | | |
| Berries | 0.722 | | | | | |
| Lees Butter | 0.662 | | | | | |
| Earthy | -0.557 | 0.490 | | | | |
| Texture | -0.548 | | 0.410 | | | |
| Baking Spices | | 0.772 | | | | |
| Sweet aromas | | 0.761 | | | | |
| Woody | | 0.731 | | | | |
| Dried Fruits Jam | | 0.589 | | | | |
| Flavor Intensity | | | 0.881 | | | |
| Length of Finish | | | 0.831 | | | |
| Palate Weight | | 0.481 | 0.687 | | | |
| Aroma Intensity | | | 0.621 | | | |
| Alcohol | | 0.406 | 0.607 | | | |
| Green Notes | | | | 0.749 | | |
| Hay Straw | | | | 0.552 | | |
| Pepper | | | | 0.516 | | |
| Brett | | | | 0.494 | | |
| Petrol | | | | 0.482 | | |
| Acidity | | | | | -0.716 | |
| Mineral | 0.457 | | | | -0.613 | |
| Perceived Sugar | | | | | 0.603 | |
| Floral | | | | | | 0.756 |
| Candied Fruit | | | | | | 0.616 |
| Native Grapy | | | | | | 0.610 |

FIG. 24

Principal Component Analysis: Dataset excluding Non-repeatable Descriptors

| | Component | | | | | |
|---|---|---|---|---|---|---|
| | 1 | 2 | 3 | 4 | 5 | 6 |
| Tree Fruits | 0.879 | | | | | |
| Citrus | 0.857 | | | | | |
| Tropical Fruits Melon | 0.850 | | | | | |
| Berries | -0.719 | | | | | |
| Lees Butter | 0.660 | | 0.433 | | | |
| Earthy | -0.574 | | 0.529 | | | |
| Texture | -0.560 | | | | | |
| Flavor Intensity | | 0.888 | | | | |
| Length of Finish | | 0.830 | | | | |
| Palate Weight | | 0.674 | 0.492 | | | |
| Aroma Intensity | | 0.632 | | | | |
| Alcohol | | 0.586 | 0.434 | | | |
| Woody | | | 0.749 | | | |
| Sweet aromas | | | 0.738 | | | |
| Baking Spices | | | 0.694 | | | |
| Dried Fruits Jam | | | 0.574 | | | |
| Green Notes | | | | 0.726 | | |
| Hay Straw | | | | 0.558 | | |
| Pepper | | | | 0.548 | | |
| Petrol | | | | 0.520 | | |
| Brett | | | | 0.505 | | |
| Acidity | | | | | -0.717 | |
| Mineral | 0.444 | | | | -0.669 | |
| Perceived Sugar | | | | | 0.538 | |
| Floral | | | | | | 0.754 |
| Candied Fruit | | | | | 0.432 | 0.659 |
| Native Grapy | | | | | | 0.612 |

FIG. 25

Principal Component Analysis: Dataset excluding Non-repeatable
Descriptors and Outliers

| | Component | | | | | | |
|---|---|---|---|---|---|---|---|
| | 1 | 2 | 3 | 4 | 5 | 6 | 7 |
| Tree Fruits | 0.842 | | | | | | |
| Tropical Fruits Melon | 0.819 | | | | | | |
| Citrus | 0.809 | | | | | | |
| Berries | 0.758 | | | | | | |
| Lees Butter | 0.756 | | | | | | |
| Texture | -0.523 | | | | | | |
| Woody | | 0.783 | | | | | |
| Baking Spices | | 0.734 | | | | | |
| Sweet aromas | | 0.712 | | | | | |
| Red Fruits Jam | | 0.621 | | | | | |
| Earthy | -0.548 | 0.597 | | | | | |
| Flavor Intensity | | | 0.895 | | | | |
| Length of Finish | | | 0.834 | | | | |
| Palate Weight | | 0.444 | 0.675 | | | | |
| Aroma Intensity | | | 0.637 | | | | |
| Alcohol | | 0.505 | 0.549 | | | | |
| Acidity | | | | -0.683 | | | |
| Perceived Sugar | | | | 0.659 | | | |
| Brett | | | | | 0.667 | | |
| Petrol | | | | | 0.636 | | |
| Pepper | | | | | 0.549 | | |
| Hay Straw | 0.435 | | | | 0.438 | | |
| Mineral | | | | | | 0.711 | |
| Floral | | | | 0.414 | | 0.676 | |
| Green Notes | | | | | | 0.459 | |
| Native Grapy | | | | | | | 0.758 |
| Candied Fruit | | | | 0.536 | | | 0.572 |

FIG. 26

Principal Component Analysis: Dataset excluding Outliers

| | Component | | | | | | |
|---|---|---|---|---|---|---|---|
| | 1 | 2 | 3 | 4 | 5 | 6 | 7 |
| Tree Fruits | 0.848 | | | | | | |
| Tropical Fruits Melon | 0.823 | | | | | | |
| Citrus | 0.812 | | | | | | |
| Lees Butter | 0.754 | | | | | | |
| erries | -0.754 | | | | | | |
| Earthy | -0.553 | 0.531 | | | | | |
| Texture | -0.532 | | 0.404 | | | | |
| Woody | | 0.781 | | | | | |
| Baking Spices | | 0.771 | | | | | |
| Sweet aromas | | 0.762 | | | | | |
| Dried Fruits Jam | | 0.616 | | | | | |
| Flavor Intensity | | | 0.888 | | | | |
| Length of Finish | | | 0.836 | | | | |
| Palate Weight | | 0.441 | 0.688 | | | | |
| Aroma Intensity | | | 0.621 | | | | |
| Alcohol | | 0.480 | 0.380 | | | | |
| Acidity | | | | -0.683 | | | |
| Perceived Sugar | | | | 0.662 | | | |
| Brett | | | | | 0.713 | | |
| Petrol | | | | | 0.579 | | |
| Pepper | | | | | 0.488 | | |
| Hay Straw | 0.416 | | | | 0.473 | | |
| Floral | | | | | | 0.721 | |
| Mineral | | | | | | 0.671 | |
| Green Notes | | | | | | 0.452 | -0.447 |
| Native Grape | | | | | | | 0.739 |
| Candied Fruit | | | | 0.497 | | | 0.525 |

Panelist Grouping Analysis (Hierarchical Clustering and Multidimensional Scaling): Dataset excluding Non-repeatable Descriptors Panelist Grouping Analysis (Hierarchical Clustering and Multidimensional Scaling): Dataset excluding Non-repeatable Descriptors and Outliers Panelist Grouping Analysis (Hierarchical Clustering and Multidimensional Scaling): Dataset excluding Outliers

FIG. 39

SYSTEMS AND METHODS FOR EVALUATION OF WINE CHARACTERISTICS

CROSS-REFERENCE TO RELATED APPLICATIONS

The present application is a continuation of and claims priority to U.S. Nonprovisional application Ser. No. 14/454,689 filed Aug. 7, 2014, entitled "Systems and Methods for Evaluation of Wine Characteristics" which claims priority to U.S. Provisional Application Ser. No. 61/863,364 filed Aug. 7, 2013, entitled "Systems and Methods for Robust Evaluation of Wine Characteristics" which are hereby incorporated by reference herein. U.S. application Ser. No. 13/627,738 filed Mar. 28, 2013, entitled "Systems and Methods for Wine Ranking" and U.S. Provisional Application Ser. No. 61/539,937 filed Sep. 26, 2012, entitled "Method and System for Hierarchical Wine Ranking" are also hereby incorporated by reference herein.

NOTICE REGARDING COLOR DRAWINGS

The patent or application file contains at least one drawing executed in color. Copies of this patent or patent application publication with color drawing(s) will be provided by the Office upon request and payment of the necessary fee.

TECHNICAL FIELD

Embodiments of the present invention(s) relate to wine selections and more particularly to systems and methods for evaluating wine characteristics for wine ranking.

DESCRIPTION OF THE RELATED ART

Although the number of mobile and web applications that recommend wines to users based on user-defined categorical requests (e.g., wine type, varietal, region, or food type) is becoming commonplace, these applications generally employ one of two inefficient techniques: a simple relational database or crowd sourcing (social networking). Typical relational databases tend to have static (i.e., unchanging) relationships between wines and foods without regard to user-specific preferences (e.g., based solely on one expert's opinion). For example, a typical relational database approach may always mandate a specific wine varietal for a specific food (e.g., Chardonnay or White Burgundy with chicken in cream sauce). This approach typically ignores the preferences or palate of the consumer in favor of an expected static interplay of the characteristics of the food versus the wine.

While crowd-sourcing techniques try to provide wine recommendations based on either personal relationships or statistical or demographic similarity between a given user and other users (i.e., the crowd), these techniques easily fail to distinguish the popularity of a given wine from an individual's preferences. In order for crowd-sourced opinion to be practical, a wine must be "sampled" by many users to provide reasonable statistical relationships. For a wine to be sufficiently sampled for crowd-sourcing, the wines must be widely available. Smaller and/or elite wineries are virtually ignored because of the lack of availability (e.g., the number of people who have sampled the wines may not be statistically significant, so these wines are not recommended).

A wine recommendation utilizing crowd-sourcing techniques may have no basis on the consumer's personal taste or individual preferences. Rather, the wine recommendation is based on the consumer's friends' or demographic preferences. Unfortunately, the range in wine preferences between users and others' preferences can be significant.

Studies also suggest a negative correlation between expert opinion of quality and non-expert preferences. It would be helpful to evaluate wine characteristics in a manner that more accurately accommodates the preferences of the consumers who actually drink the wine.

SUMMARY OF EMBODIMENTS

In some embodiments, a system comprises a wine panelist interface module configured to receive wine evaluations of wines from wine panelists, each wine evaluation including intensity values describing a plurality of wine characteristics for each of a set of wines, each wine evaluation generated by a wine panelist; an accuracy management module configured to generate a global intensity value from particular intensity values describing a particular wine characteristic of a particular wine, the particular intensity values being from the wine evaluations, configured to compare a selected intensity value generated by a selected wine panelist describing the particular wine characteristic for the particular wine against the global intensity value to determine an accuracy deviation, and configured to compare the accuracy deviation against an accuracy deviation threshold to determine whether the selected intensity value is deemed inaccurate based on the comparison; a wine panelist statistical processing module configured to update the global intensity value for the particular wine characteristic for the particular wine based on the accuracy determination; and a wine database configured to store the updated global intensity value.

A method comprises receiving wine evaluations of wines from wine panelists, each wine evaluation including intensity values describing a plurality of wine characteristics for each of a set of wines, each wine evaluation generated by a wine panelist; generating a global intensity value from particular intensity values describing a particular wine characteristic of a particular wine, the particular intensity values being from the wine evaluations; comparing a selected intensity value generated by a selected wine panelist describing the particular wine characteristic for the particular wine against the global intensity value to determine an accuracy deviation; comparing the accuracy deviation against an accuracy deviation threshold to determine whether the selected intensity value is deemed inaccurate based on the comparison; updating the global intensity value for the particular wine characteristic for the particular wine based on the accuracy determination; and storing the updated global intensity value in a wine database.

In some embodiments, a system comprises a wine panelist interface module configured to receive wine evaluations of wines from wine panelists, each wine evaluation including intensity values describing a plurality of wine characteristics for each of a set of wines, each wine evaluation generated by a wine panelist; a precision management module configured to receive a first intensity score and a second intensity score generated by a particular wine panelist describing a particular wine characteristic of a particular wine, the first intensity score and the second intensity score being received from a particular wine evaluation of the particular wine panelist, configured to compare the first intensity value against the second intensity value to determine a precision deviation, and configured to compare the precision deviation against a precision deviation threshold to determine whether the particular wine panelist is deemed precise as to the particular wine characteristic of the particular wine based on the comparison; a wine panelist statistical processing module configured to generate a global intensity value for the particular wine characteristic for the particular wine based on the precision determination; and a wine database configured to store the global intensity value.

In some embodiments, a method comprises receiving wine evaluations of wines from wine panelists, each wine evaluation including intensity values describing a plurality of wine characteristics for each of a set of wines, each wine evaluation generated by a wine panelist; receiving a first intensity score and a second intensity score generated by a particular wine panelist describing a particular wine characteristic of a particular wine, the first intensity score and the second intensity score being received from a particular wine evaluation of the particular wine panelist; comparing the first intensity value against the second intensity value to determine a precision deviation; comparing the precision deviation against a precision deviation threshold to determine whether the particular wine panelist is deemed precise as to the particular wine characteristic of the particular wine based on the comparison; generating a global intensity value for the particular wine characteristic for the particular wine based on the precision determination; and storing the global intensity value in a wine database.

In some embodiments, a system comprises a wine panelist interface module configured to receive wine evaluations of wines from wine panelists, each wine evaluation including intensity values describing a plurality of wine characteristics for each of a set of wines, each wine evaluation generated by a wine panelist; a bias management module configured to generate a global intensity value from particular intensity values describing a particular wine characteristic for each of the set of wines, the particular intensity values being from the wine evaluations, configured to compare respectively selected intensity values generated by a selected wine panelist describing the particular wine characteristic across the set of wines against the global intensity values across the set of wines to determine accuracy deviations across the set of wines, configured to modify the particular intensity values if the accuracy deviations across the set of wines meet a predetermined condition; and a wine panelist statistical processing module configured to update the global intensity values describing the particular wine characteristic for the set of wines based on the accuracy deviations; and a wine database configured to store the updated global intensity values.

In some embodiments, a method comprises receiving wine evaluations of wines from wine panelists, each wine evaluation including intensity values describing a plurality of wine characteristics for each of a set of wines, each wine evaluation generated by a wine panelist; generating a global intensity value from particular intensity values describing a particular wine characteristic for each of the set of wines, the particular intensity values being from the wine evaluations; comparing respectively selected intensity values generated by a selected wine panelist describing the particular wine characteristic across the set of wines against the global intensity values across the set of wines to determine accuracy deviations across the set of wines; modifying the particular intensity values if the accuracy deviations across the set of wines meet a predetermined condition; updating the global intensity values describing the particular wine characteristic for the set of wines based on the accuracy deviations; and storing the updated global intensity values in a wine database.

Other features and aspects of various embodiments will become apparent from the following detailed description, taken in conjunction with the accompanying drawings, which illustrate, by way of example, the features of the various embodiments.

BRIEF DESCRIPTION OF THE DRAWINGS

FIG. 3 depicts an exemplary abbreviated wine database entry, according to some embodiments.

FIG. 16 depicts a table that illustrates the difference between intensity values of two wine panels, according to some embodiments.

FIG. 17 depicts a table that illustrates the difference between intensity values of two wine panels, according to some embodiments.

FIG. 18 depicts a table that illustrates the difference between intensity values of two wine panels, according to some embodiments.

FIG. 19 depicts a table that illustrates the difference between intensity values of two wine panels, according to some embodiments.

FIG. 20 depicts a table that illustrates the difference between the scores by the number of wines per flight, according to some embodiments.

FIG. 21 depicts a table that illustrates the difference between the scores by the number of wines per flight, according to some embodiments.

FIG. 22 depicts a table that illustrates average panelist bias, according to some embodiments.

FIG. 23 depicts a table that illustrates the results of wine ranking processing for several varieties of wine, according to some embodiments.

FIG. 24 depicts a table that illustrates principal component analysis of a dataset of descriptors, according to some embodiments.

FIG. 25 depicts a table that illustrates principal component analysis of a dataset that excludes non-repeatable descriptors, according to some embodiments.

FIG. 26 depicts a table that illustrates principal component analysis of a dataset that excludes non-repeatable descriptors and outliers, according to some embodiments.

FIG. 27 depicts a table that illustrates principal component analysis of a dataset that excludes outliers, according to some embodiments.

FIG. 28 depicts a table that illustrates repeatability analysis of a dataset of wines, according to some embodiments.

FIG. 39 depicts an example of a wine score sheet for sensory evaluation, according to some embodiments.

DETAILED DESCRIPTION OF VARIOUS EMBODIMENTS

In various embodiments, user-specific input, experiences, and feedback may be used to train a system to rank wines from a general wine database. The system may provide wine rankings in the context of user preferences without regard to other users or static relationships. One exemplary method uses numerical (or other scoring criteria) wine characteristics (e.g., based on a predefined character "map" and an expert-derived intensity scale), which are compiled for wines from a user-specific wine experience database to compute a statistical "proxy" of the user's experiences and preferences in wine characteristics. This "wine proxy" may be treated as a linear mathematical operator by which future user wine requests or searches can be filtered in order to provide user-specific ranked results for the purposes of purchase or general wine education. Once users have tried wines from the system's ranked wines, they can provide their own ratings which are incorporated (e.g., via a proxy regression) into future rankings from the database.

Some embodiments allow a relatively small wine database to be used to generate useable statistics thereby making the system efficient. The user proxy and subsequent filtering operations may be generated with little computational overhead (i.e., the system may be scalable). Those skilled in the art will appreciate that, in some embodiments, the wine characteristics used for analysis may be uncorrelated and/or may be statistically independent.

As opposed to other techniques known in the fields of machine learning such as Bayesian classification (based on poorly informed prior probabilities or poor assumptions of parameter independence), or cluster analysis (which usually depends on vague distance measures in a parameter space), some exemplary embodiments may: 1) assure that parameters are uncorrelated (and usually independent in cases of Gaussian posterior probability distributions); 2) be implemented so as to be insensitive to statistical priors; and 3) maintain wine character correlation information for future classifications or rankings. In addition, the analysis may be performed in a reduced-dimensional user preference space, which may add efficiency to the problem of statistical classification with large datasets.

The following example method can have several embodiments including, but not limited to, web-based or mobile application, static platform-specific application (e.g., PC/MAC/Linux), or cloud-based (server-based) application.

Figure 1:
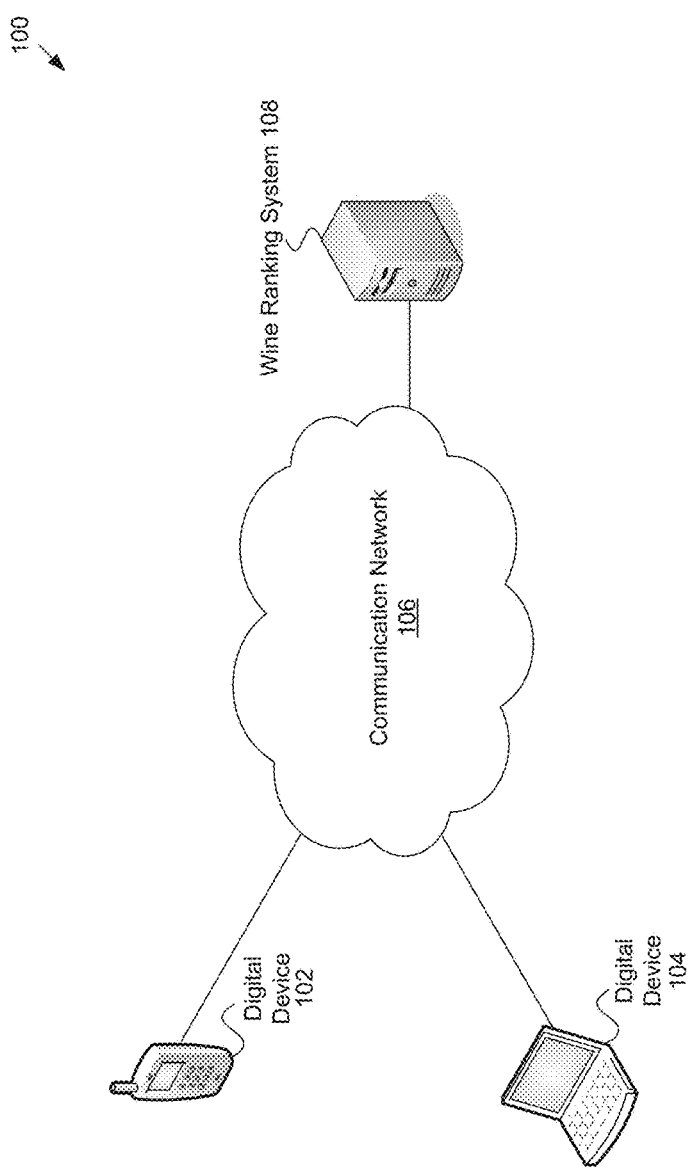
FIG. 1 depicts two digital devices in communication with a wine ranking system over a communication network, according to some embodiments.

FIG. 1 depicts two digital devices 102 and 104 in communication with a wine ranking system 108 over a communication network 106 in some embodiments. The digital device 102, digital device 104, and the wine ranking system 108 may be digital devices. A digital device is any device with memory and a processor. In some examples, digital devices 102 and 104 may be a mobile or stationary user device such as, but are not limited to, smart phones, cell phones, laptops, media tablets, desktop computers, ultrabooks, smart peripherals (e.g., smart glasses), media players, or the like. In some embodiments, the digital device 102 and/or digital device 104 may comprise an application (e.g., an app) that communicates with the wine ranking system 108.

In various embodiments, a user of either digital device 102 and 104 may register with and/or request wine rankings from the wine ranking system 108. In one example, digital device 102 provides the wine ranking system 108 with information regarding a user's wine preferences. The wine ranking system 108 may build a user wine database based on the user's past wine consumption and indications of the user's preference for the wine. The wine ranking system 108 may determine the user's preferences of different wine characteristics (e.g., acidity, sugar, alcohol, and tannins) and then rank a list of wines based on the user's personally desired characteristics.

The wine ranking system 108 may comprise a wine database. The wine database may comprise wine identifiers as well as wine descriptors correlated with each wine identifier. A wine identifier identifies a particular wine (e.g., Robert Foley Claret 2010). A wine descriptor is a characteristic of a wine (e.g., acidity, alcohol, sugar, tannins, or the like). Each wine descriptor may have an associated intensity value. An intensity value represents a degree of actual and/or perceived presence of the wine characteristic. An intensity value may be defined for a certain range. For example, an intensity value may be zero to six, with zero indicating that the related wine characteristic is not present (e.g., no perceivable tannins) and a six being a maximum amount of the related wine characteristic. Those skilled in the art will appreciate that there may be any range or representation of intensity values.

The wine ranking system 108 may utilize the user wine database to select wines based on a similarity of the user wine characteristic preferences with the different intensity values of descriptors of wines contained in the wine database.

In one example, the user may register with the wine ranking system 108 and train a user wine database based on previously preferred wines and the user's past experiences. The user may train and/or update an associated database by providing wine identifiers (e.g., brand names, varietals, and/or vintages) as well as an indication of how much they enjoyed the wine (e.g., one to five stars).

After the user wine database is created and trained, the digital device 102 may provide a wine request to the wine ranking system 108 to request a selection of wines as well as a ranking of wines selected. The wine request may identify the user (and/or the digital device 102) and may provide one or more categorical classifications. A categorical classification is a category associated with wine such as, but not limited to, a name of a wine, a varietal of a preferred type of wine, a region of preferred wines, a color of preferred wines, and/or the like. The wine database may associate one or more wines and/or intensity values with categorical classifications. In various embodiments, the user may not be sophisticated and, as a result, the user may provide general types of wine or categorical classifications.

The wine ranking system 108 may generate a wine proxy for the user based on the user's past experiences with wine and preferences. The wine proxy may be utilized to select and rank a list of wines based on the wine database. For example, the wine ranking system 108 may correlate or find similarities of the user wine proxy to the predetermined descriptors and/or intensity values of different wines contained within the wine database. The system may utilize these similarities or correlations to select and/or rank wines for the user. The wine ranking system 108 may also utilize one or more categorical classifications from a wine request and the user's wine proxy to select, rank, and/or filter a list of selected wines as further described herein. The ranked wines may be provided to the user via the requesting digital device 102.

In various embodiments, the wine ranking system 108 may comprise or be associated with a web server that provides wine recommendations and/or rankings to the digital device 102 via the Internet. The wine ranking system 108 may include any number of digital devices (e.g., servers) configured to identify and/or rank wines for users.

Those skilled in the art will appreciate that the wine database and/or user wine databases may be stored on any digital device such as the digital devices 102 or 104 or the wine ranking system 108. Further, the wine database and user database may be stored on one or more other databases in one or more other digital devices coupled to the communications network 106, the digital device 102, the digital device 104, or the wine ranking system 108.

Although only two digital devices are depicted in FIG. 1, those skilled in the art will appreciate that there may be any number of users with user databases and/or associated digital devices. Further, there may be any number of networks 106 and/or wine ranking systems 108. In some embodiments, the wine ranking system 108 recommends wine based on the user's preferences as described herein. Those skilled in the art will appreciate that the wine ranking system 108 may operate to recommend wines, rank wines, or both.

Figure 2:
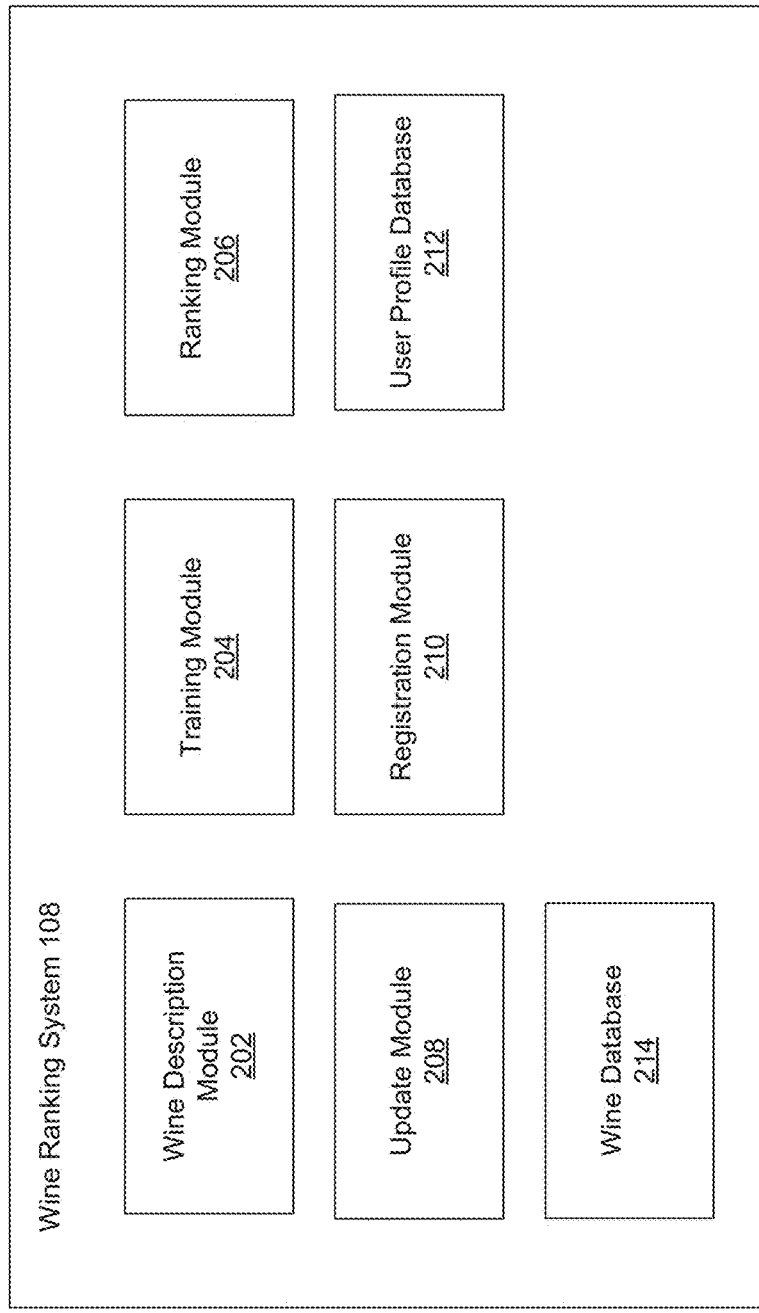
FIG. 2 depicts a block diagram of a wine ranking system, according to some embodiments

FIG. 2 is a block diagram of a wine ranking system 108 in some embodiments. The wine ranking system 108 may comprise a wine description module 202, a training module 204, a ranking module 206, an update module 208, a registration module 210, a user profile database 212, and a wine database 214. The wine description module 202 may generate and/or update a wine database. The wine database is a database or any data structure that comprises wine identifiers with corresponding wine characteristics. Each discrete characteristic for a wine, or descriptor, may be based, for example, on aroma or taste. A wine descriptor is a wine characteristic such as, but not limited to, acidity, alcohol, sugar, tannins, or the like which may be used to describe any number of wines. These discrete characteristics, or descriptors, for each wine may be elementized (i.e., identified), and quantified (i.e., intensities assigned) to create a discrete parameter. Each wine descriptor may have an associated intensity value. An intensity value may be any value such as a number or score that represents a degree of actual and/or perceived presence of the descriptor in a particular wine.

In some embodiments, one or more wines in the wine database may be associated with any number of categorical classifications (e.g., wine name, varietal, vintage, region, and/or appellation). Categorical classifications include categories that may apply to and classify wine. The categorical classifications may include categories that relate to wine that may represent a type of wine (e.g., color, varietal, vintage, region, winery, wine name, appellation, or the like).

The wine database may comprise information regarding wines numbering as few as hundreds to as many as millions of distinct wines (constituting an appropriate representation spanning various wine types, varietals, regions, etc.).

In some embodiments, experienced individuals (e.g., experts) identify wines and quantify a set of discrete parameters. The experienced individuals may be any individual with training and/or experience to describe wine utilizing the discrete parameter set. Wines that define a set of discrete data may be analyzed by the experienced individuals in terms of the wine characteristics or parameter set. An exemplary method defines wine characters using wine tasting criteria and descriptive language.

Experts or any individuals may be trained to utilize a scoring system (e.g., determine intensity values) for a limited number of wine characteristics (e.g., descriptors) of the discrete set. By training the individuals to use the scoring system and the previously determined descriptors, different experts may utilize a similar language (e.g., based on the descriptors) and a more objective approach to describing wine.

In some embodiments, each experienced individual may assign numerical values (i.e., scores or intensity values) denoting how much a particular character is perceived to be represented in each wine. The intensities may be assigned utilizing a taster-subjective (i.e., expert opinion) intensity scale. The intensity value may be based on or converted to any scale. In one example, the intensity values may range from 0-6 for each character (i.e., for each descriptor). Those skilled in the art will appreciate that any range of intensity values may be utilized. The intensity values need not be restricted to integers. The intensity values may be positive, negative, or a combination of both.

The character data, the relative intensities, and the wine descriptive information constitute a wine parameter database that may cover many different wine varietals, geographic regions, wine producers, and vintages.

FIG. 3 depicts an exemplary abbreviated wine database entry in some embodiments. In this case, the first six columns correspond to various identifying and searchable information for the wine, while the last four columns represent example wine characteristics and their relative intensities assigned by the system. Here, the wine has characteristics denoting "Fruit, Earth, Spice, and Resin" with respective intensities equal to "0.5, 2.5, 2.0 and 3.5," respectively. This wine with its four parameters and intensities would then represent one datum for a 4-parameter character set. Those skilled in the art will appreciate that the number of characters may be much larger than four and the number of wine entries much larger than one.

Those skilled in the art will appreciate that any group of individuals and/or analytical devices may be used to associate wine with different descriptors and intensity values. An individual may not need to be a recognized expert to be able to associate the wine with a descriptor and intensity value. For example, a set of individuals (e.g., students) may be trained to utilize the system to associate different wines with descriptors and intensity values. The information may be stored in the wine database.

In various embodiments, natural language processing (NLP) techniques such as machine learning may be used to interpret contextual semantic text from existing wine tasting notes. For example, wine tasting notes or wine reviews from any expert or other individual may be processed to identify descriptors and intensity values associated with those descriptors. Natural language processing may be utilized with any document describing wine, including documents such as web pages or portions of web pages available on the Internet. Other sources may include wine bottle labels, wine descriptions in magazines or trade publications, blogs, Facebook discussions, or the like.

Natural language processing may scan and convert language to descriptors and intensity values. See Table 1 for an example of a very simple semantics-based character intensity scale.

TABLE 1

Example of semantic description and corresponding
intensities for relative wine character scale.

| Words typical of level of intensity | Suggested Scale Value |
|---|---|
| "aromas, nose of" | 0.5 (MINIMUM) |
| "nuance, hint, pungent-nose" | 1.0 |
| "mild, little, bit, light, touch" | 1.5 |
| "some, notes of" | 2.0 |
| If character is mentioned with NO descriptor | 2.5 |
| "(spice)'y', (fruit)'y', etc." | 3.0 |
| "plenty, long, moderate, layered, concentrated" | 3.5 |
| "lingering, pungent, powerful, generous" | 4.0 |
| "extravagance, abundance, intense, overpowering" | 4.5 |
| "lots, burning, excessive" | 5.0 (MAXIMUM) |

Wine identifiers (i.e., identifiers that identify a specific wine), associated descriptors and related intensity scores (e.g., by utilizing experts and/or natural language processing) may be stored in the wine database.

The training module 204 of FIG. 2 is configured to generate and/or train a user wine database based on wines identified by the user. In various embodiments, in order to train the system to rank wines for each user, a user database of wines (e.g., a subset of the wine database) that is unique to each user is determined from input about the user's wine experiences. In one example, a user input may comprise messages from the user regarding wines, preference scores, and/or any other information.

In some embodiments, to keep the input simple, the system need not require the user to input specific characteristics in wine they like (since the user may or may not be knowledgeable of wine characteristics). Rather, the system (e.g., training module 204) may ask the user and/or the user may provide examples of wines or wine types that they have experienced and prefer. An exemplary system query for the user may request general wine information related to wines preferred or consumed in the past (See Columns 1-6 in FIG. 3). Such categorical classifications may include, but are not limited to: user preference for wine type(s), region(s), varietal(s), or producer(s). This information may then be used to limit (i.e., match) the wines in the wine database to a subset of wines (i.e., the "training" database) unique to each user's experiences.

In various embodiments, the training module 204 may translate one or more categorical classifications to wine descriptors and/or user preference intensity values. For example, the user may be provided a limited list of categorical classifications to choose from. The selections may be provided to the training module 204 which may associate the categorical classifications with one or more descriptors. The user preference intensity values related to the categorical classifications may be determined. A user preference intensity value is an intensity value associated with a descriptor. The intensity value may be provided by the user or determined based on information provided by the user. If the categorical classification does not relate to an intensity of the descriptor, the user preference intensity value associated with the categorical classification may be given a neutral value.

For example, the user may provide the wine ranking system 108 one or more categorical classifications. The training module 204 may retrieve wines from the wine database that match the one or more categorical classifications. The intensity scores of descriptors associated with the selected wines may be utilized to generate (e.g., by averaging the preexisting intensity scores) user preference intensity values. In some embodiments, the user may provide additional information, such as wine preference and appreciation value which may be used to weigh and determine the user preference intensity values. For example, the user may provide a categorical classification indicating that the user prefers red wine. Descriptors and related intensity values of wines associated with red wines may be utilized to generate the user's wine proxy (further discussed herein).

The training module 204 may also determine when limited user input is sufficient for further analysis based on statistical and hypothesis tests for small sample populations (e.g., critical T-values). The resulting training database may be used to calculate user-specific statistics. The user database may be stored and updated as necessary by the system for future use. Those skilled in the art will appreciate that any number of wines may be sufficient.

The ranking module 206 is configured to identify wines of interest to users based on descriptors and user preference intensity values from the associated user database (e.g., user profile). In various embodiments, the ranking module 206 takes parametric information (characters and intensities) from the user training database, performs a spatial correlation across parameters and wine entries, and uses the resulting statistical correlations to mathematically reduce the parameter set to a limited number of new uncorrelated variables which, taken in linear combination, may uniquely define the user's wine preference (i.e., the user wine proxy). There are multiple embodiments of this statistical de-correlation process which may include, but not limited to: principal component analysis (PCA), independent component analysis (ICA), singular value decomposition (SVD), or other matrix de-correlation method (e.g., discrete cosine transform (DCT), wavelet transform, or orthogonal polynomial decomposition).

Describing an approach utilizing principal component analysis as one example, the mathematical procedure transforms, a number of correlated variables (i.e., wine characters in this case) into an equal number of uncorrelated variables (vectors), called principal components, while maintaining their full variance and ordering the components by their contribution. The resulting transformation may be such that the first principal component represents the largest amount of variability (i.e., has the largest weight), while each successive component may account for at least some of the remaining variability. The number of wine parameters can be reduced significantly by replacing them with the first few principal components (based on relative amplitudes of weights) that capture most of the wine character variance.

In one example, let us assume that the training database has M wines and that each wine has N characters (e.g., descriptors). A wine character covariance (N×N) matrix then can be estimated from the training database according to the approximation:

$$C = 1/M \sum_{i=1}^{M} [ch_i - \langle ch \rangle]^T [ch_i - \langle ch \rangle] \qquad (1)$$

where M is the total number of wines in the training database, $\langle ch \rangle$ is the wine mean character intensity vector computed for all N characters (i.e., intensity values) across all M wines, and $ch_i$ is each character intensity vector (length=N) for each of the M wines in database.

The covariance matrix may include all or some wines that are included in the wine database. The covariance matrix, which may be termed an "experimental covariance," may be an estimate of the true covariance of all wines (including those that are not in the database). The covariance may be estimated (i.e., the estimated or experimental covariance). Every covariance may be centered.

In some embodiments, the statistics across all wines and all descriptors are averaged to get the mean which is subtracted from all wine in the wine database. In one example, an average of all descriptors across all wines is taken (e.g., average vector) and subtracted. The summation is the residuals (what is left) for all descriptors of all wines. The covariance may be computed by taking the correlation between every descriptor and every other descriptor. In some embodiments, the process correlates and/or relates descriptors with each other (e.g., how sugar relates to color, how sugar relates to alcohol, and the like).

For a twenty-seven (27) descriptors matrix, the covariance should be 27×27 (e.g., 27 squared values including a correlation between themselves and every other descriptor). The summation is the correlation between every descriptor in the database. Since C is a symmetric semi-positive definite matrix, the principal components of the training database may be computed by solving what is known as the Eigenvalue problem for the N wine characters:

$$C\lambda = \lambda V \quad (2)$$

The matrix V contains the N Eigenvectors (i.e., principal components) of the de-correlated user wine parameter basis. The vector λ contains the N Eigenvalues (principal component weights representing the relative importance of each individual Eigen-character, $V_i$, in describing the user's wine "type").

In various embodiments, the ranking module 206 may pick a small or smallest subset, P<<N, of Eigenvectors (e.g., in order to reduce ambiguity or uncorrelated noise in our character space) from this base that adequately account for most of our wine character variability according to the criteria, e.g.:

$$\Sigma \lambda_i[1:P]/\text{trace}[C] \geq 70\%. \quad (3)$$

Trace of C may be the summation of diagonal terms in a matrix. Weights for all columns of matrix V may be decreasing from largest to smallest. As a result, the first principal component of V first column may have a large λ compared to all the others. Although 70% represents the number of λ values whose sum is approximately 70% of the summation of all λ values, equation (3) may be to any percentage (e.g., higher or lower than 70%). In various embodiments, by cutting off λ values, noise may be reduced. Further, as the percentage is decreased, the process may become more efficient. In some examples P<10.

Whether the system uses all N or just P components of the de-correlated basis, these new wine Eigen-characters approximate the variance (and to a lesser extent the correlation) of wine characteristics (about the mean "composite wine" vector⟨ch⟩) in each user's wine database (e.g., user profile) following the mathematical form:

$$\text{var}[\text{wine}]_{user} = \langle ch \rangle + \lambda_{user} V. \quad (4)$$

We have denoted the user's variance in preferred wine experiences as $\text{var}[\text{wine}]_{user}$. In this context, the larger each $\lambda_i$, the more important (and more correlated across the database) each component, $V_i$, may be in describing the likes of the user for the particular set of wines in the training database; equation 4 may completely describe the user's individual "wine proxy" as the set of Eigen-characters V (i.e., a linear mathematical filter), the mean character vector ⟨ch⟩ and the relative importance values $\lambda_{user}$ (i.e., the filter weights). All or some of the components of the user proxy may be stored by the system for future steps.

In essence, equation 4 may project the wine characters into a new mathematical space (i.e., the user "proxy space") that exploits the statistical relationship between different wine characters. This is useful, because it: 1) allows the system to define wines with fewer variables (since, for example, "acidity" and "resin" wine characteristics may be perfectly correlated in many wines, we can represent both with a single principal component rather than the more complicated individual characteristics), and 2) it provides the system with a filter to make certain all future user wine requests and rankings are statistically consistent with each users' prior experiences.

Those skilled in the art will appreciate that the largest Eigenvalue ($\lambda_1$) in equation 4 may represent the least distinguishing proxy character for wine, because all wine share this character (this $v_1$ represents the maximum correlation between all wines in the subset), while the smallest Eigenvalue ($\lambda_N$) may represent the most distinguishing proxy character, because it is correlated between wines less than all other wine characters—it may be the most unique Eigen-character.

In some embodiments, matrix V is consistent with equation 2 and specific to the user. The statistical proxy may include the user's λ values, V, and CH. The ranking module 206 may utilize this process to create a basis for initial ranking of wine.

Once the user proxy is computed, future user wine requests may be filtered by the operator V in order to transform all wines from a new "dynamic" database into the user's proxy space. To this end, equation 4 may allow the user to specify new wine descriptors (e.g., wine type, varietal, producer, region) they are currently interested in having the system rank. The update module 208 then uses this information to build a dynamic database which is distinct from the training discussed herein. In one example, the update module 208 updates the existing user database with wines to those of current interest. Then the update module 208 "projects" each wine (e.g., the update module 208 projects each wine's characteristics as defined herein) contained in this dynamic database to the user proxy space by solving the small (P×P) principal component (PC) problem:

$$\lambda_{wine_i} = [ch_{wine_i} - \langle ch \rangle] V \quad (5)$$

Here, $\lambda_{wine}$ is each of i wines PC defined by each character vector, $ch_{wine}$, contained in the dynamic database and filtered by the Eigen-vector operator V.

The system may rank (in either ascending or descending order) all i wines from the dynamic database according to their mathematical similarity/difference, $S_i$, in the proxy space to the previously defined user wine proxy values, $\lambda_{user}$, from equation 4:

$$S_i = \sum_{i=1}^{P} |\lambda_{user} - \lambda_{wine_i}| \quad (6)$$

This similarity/difference values can also be determined using any number of techniques including Euclidean norm (simple summed difference as shown in equation 6), mean difference, root-mean-squared difference, chi-squared, etc.

In various embodiments, every wine in a database that matches a search may be assessed. In one example, wines are retrieved that match a search based on a user wine request and then the related descriptors may be converted to a mathematical space to look for similarity with the statistical proxy.

In various embodiments, the term ranking may include that the system includes all matching wines from the dynamic database, but then ranks them according to similarity, S, to user likes/dislikes (e.g., correlating the preexisting intensity values stored in the wine database with the user preference intensity values of the user wine database. Then the user can choose any of the wines they want according to or regardless of ranking. That is, the system may return all wines with additional information, but allows the user to decide on the wine. The term recommendation may include that the returns either a very limited subset of all matching wines from the dynamic database for the user to then choose from or the system returns all wines that match search terms irrespective of degree of similarity, S. Here, the system does most of the choosing for the user.

Because the system has statistical information regarding the user's wine preferences, the system may rank wines that are not in the dynamic database from Step 3. For example, if the composite wine, ⟨ch⟩, from equation 4, is more similar to the user's proxy than any other single wine from the dynamic database. In this sense, the exemplary system may interpret the mean wine vector to be a new composite wine (one derived from statistics not from the database of wines) that itself can be matched against the complete Step 1 static database, per equation 6, to compute a new ranking for all other wines outside the dynamic database. This may allow the system to provide the user with a set of alternative wines that potentially fit their taste better than any single wine from the types, producers, regions, etc. that they requested.

In one example, the user wine database is trained to include information regarding a preference for light-bodied wines from the south of France. Subsequently, the user may request that the system rank Barolos from Italy and Napa Valley cabernets. In computing the mean composite wine, ⟨ch⟩, from equation 4, the system may determine that the statistical mean fits the user's proxy (according to equation 6) better than any individual Barolo or Napa Valley cabernet. The system then may then match the composite to the entire static database and rank all wines relative to the composite. In this sense, the system may triangulate to rank wines that may be preferred by the user more than (but are still consistent with) either Barolos or Napa Valley cabernets.

In some embodiments, the system stores at least some wine rankings from Steps 2 and 4 that the user specifies and allows the user to rate (e.g., on a relative scale from 0-5) the wines they have tried from this list over time. The user wine proxy may then be updated to reflect these user feedback ratings by solving a regression problem (mathematical fitting problem). This technique (which has many embodiments) may incorporate new observations (user ratings) into the user proxy vector (λ) via the general mathematical form:

$$[\lambda_{update}] = [\lambda R_w \lambda^T + \epsilon I]^{-1} \lambda^T R_w C \qquad (7)$$

$R_w$ is a diagonal weighting matrix containing the relative user ratings for each wine, I is identity matrix, $\epsilon$ is a damping term for stabilization, C is the vector containing the sum of each wine vector residual (projected into the proxy space) for all wines (stored by the system from the previous training and ranking steps), and λ is per equation 5 for each wine. This updated $\lambda_{update}$ is used to update $\lambda_{user}$ ($\lambda_{new} = \lambda_{update} \cdot \lambda_{update}$), is stored by the system, and replaces $\lambda_{user}$ in all future Step 4 rankings. The average ⟨ch⟩ is also updated accordingly from the composite list of all wines rated and in the dynamic database. Then as the user tries/rates more wines, the system will better adapt to the user's likes/dislikes and rankings will increase in accuracy going forward.

Retrieved (e.g., selected) wines may be ranked based on the similarity to the statistical proxy. The identifiers (e.g., labels, names, or the like) of the wines may be ranked. In some embodiments, when the ranked wines are provided, wine identifiers, location where the wine is available, degree of similarity, and/or pricing may be provided to the user. In some embodiments, the ranking module 206 may provide a value number based on price and fitness (e.g., akin to a PE ratio of a stock).

In various embodiments, the wine ranking system 108 provides a ranking of wines based on a subset of the wines in the wine database. For example, the user may request wines that are available based on location (e.g., restaurant, wine bar, or the like) and/or based on categorical classifications (e.g., wine color, winery, or the like). In some embodiments, the wine ranking system 108 may select a subset of the wine database to correlate with the user's wine proxy.

In one example, the selected subset of the wine database may include wines that are available at the user's location (e.g., wines of Forbes Mill Steakhouse of Los Gatos, Calif.) but not include wines that are not available at the user's location. Similarly, the wine ranking system 108 may select a subset of wines from the wine database based on categorical classifications. For example, the user may request a selection and/or ranking of wines that are red in color and is described as having a light body. The wine ranking system 108 may receive the categorical classifications in a wine request and select a subset of wines from the wine database that meet the categorical classifications.

In some embodiments, the wine ranking system 108 may utilize all wines in the wine database but subsequently select a subset of ranked and/or individually identified wines based on the user's location and/or categorical classifications. For example, all wine of the wine database may be ranked based on the user's wine proxy. The results may be filtered based on the user's location (e.g., only wines currently available at Beltramos Wine and Spirits or Beverages and More!) or based on the categorical classification(s) (e.g., red wines from Paso Robles, Calif.). The subset or filtered results may be provided to the user. Those skilled in the art will appreciate that there are many ways to identify and/or rank one or more wines based on the wine request.

The update module 208 is configured to update the user database (i.e., the user profile). In various embodiments, the update module 208 may receive an update request from a user via a digital device 102. The update request may include an identifier (e.g., a user or digital device identifier), a wine identifier as well as an indication of preference (e.g., 1-5 stars). The update module 208 may update the user's proxy based on the new information. For example, the update module 208 may retrieve a wine from the wine database based on the wine identified in the update request, weigh preexisting intensity values from the wine database based on the indication of preference and recalculate the user's wine proxy including the new information.

The registration module 210 is configured to register users. In various embodiments, the digital device 102 may provide the wine ranking system 108 a wine registration message. The wine registration message may include a user identifier (e.g., username, password, and the like) as well as other information personal to the user. In one example, the wine ranking system 108 comprises a web page that requests registration information (e.g., user identifier and other information) from an interested user. The registration module 210 may receive the information and generate a consumer wine preference profile for the user. The consumer wine preference profile may identify and link the user with the user's associated user wine database. The registration module 210 may issue a username, password, account number of the like. The registration module 210 may allow for communication of wine rankings and other information via a mobile device or any other device.

If registration is successful (e.g., sufficient user information is provided), the registration module 210 may trigger the training module 204 to request information regarding past wines consumed by the user and/or other experiences. Subsequently, the training module 204 may generate and/or train the user database.

The user profile database 212 may include any database(s) or other user structure(s) to store user databases. As discussed herein, a user database and/or the consumer wine preference profile may include any information regarding a user's past experiences with wine, including past wines consumed, user scores of the wine, past wine requests, past wine recommendations and rankings, location of the user, price point preferences of the user, user intensity preference values, and the like. In some embodiments, the user database comprises a wine proxy for the user based on information as described herein.

Those skilled in the art will appreciate that the user profile database 212 may be remotely located from the user and/or the wine ranking system 108. In some embodiments, the user profile database 212 may be stored in the user's digital device.

The wine database 214 may include the wine database as described herein. The wine database 214. The wine database 214 may include any database(s) or other user structure(s) to store one or more wine databases. The wine database 214 may be remotely located from the user and/or the wine ranking system 108.

A module is any hardware, software, or combination of both hardware and software. Those skilled in the art will appreciate that the modules identified in FIG. 2 may perform more or less functionality as described herein. For example, some modules may perform the functions of other modules. Further, functions shown with respect to FIG. 2 are not limited to a single digital device but may be performed by multiple digital devices performing different functions. In some embodiments, multiple digital devices perform functions simultaneously.

In some embodiments, one or more of the functions described herein may be performed on the user's digital device 102. For example, instead of sending an update request, the user may input the update information into the digital device 102 which may, in turn, generate the user database and/or wine proxy. The wine proxy or any other information may be provided to the wine ranking system 108 to receive a recommendation or wine ranking. In some embodiments, some information is provided to the digital device 102 which subsequently may apply the wine proxy, select wines, and/or rank wines. Those skilled in the art will appreciate that the functions described herein may be performed by different devices in any number of ways.

Figure 4:
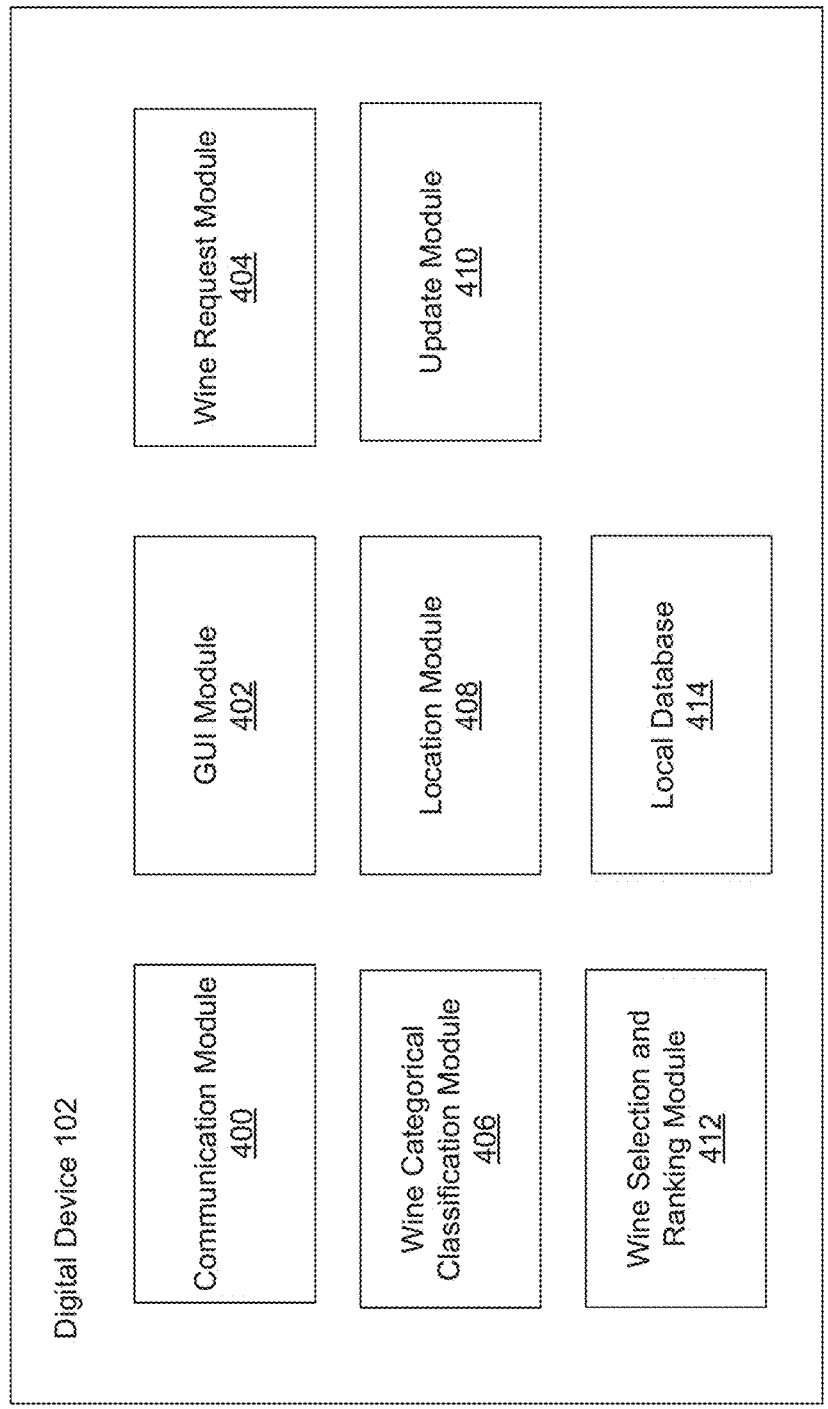
FIG. 4 depicts a block diagram of a digital device, according to some embodiments.

FIG. 4 is a block diagram of a digital device 102 in some embodiments. The digital device 102 may comprise a communication module 400, a GUI module 402, a wine request module 404, a wine categorical classification module 406, a location module 408, an update module 410, a wine selection module 412, and a local database 414.

In some embodiments, the digital device 102 is a mobile device such as a smart phone, tablet, or the like. The digital device 102 may comprise an application, app, or any other functionality to communicate with the wine ranking system 108 and provide wine selections and/or rankings. In one example, the communication module 400 comprises a browser configured to access a web page provided by the wine ranking system 108. The browser may be used to register, provide training information, provide update information, request wines, and/or request wine rankings. The communication module 400 may comprise any hardware or software configured to communicate with the wine ranking system 108.

In some embodiments, the communication module 400 communicates with the wine ranking system 108 over an encrypted link to protect user privacy and information. For example, a user may digitally sign communication or establish an encrypted connection with the wine ranking system 108 prior to registration, training the user wine preference profile, updating the user wine preference profile, and/or requesting wine rankings from the wine ranking system 108. Examples of encrypted technologies that may be utilized include, but are not limited to, hypertext transfer protocol secure (HTTPS), VPN, SSL, or the like.

The GUI module 402 may provide a graphical user interface to the user. The GUI module 402 may be a part of a wine ranking application or provide an interface for the user to provide and receive information. In some embodiments, the GUI module 402 may utilize one or more APIs of the wine ranking system 108 and/or any other device or software.

The wine request module 404 may provide a wine request to the wine ranking system 108. In one example, the user may activate a wine ranking application on a smartphone. The user may request a wine selection and/or a ranking of wines with the wine request module 404. The wine request module 404 may generate a wine request including a user identifier (i.e., an identifier of the user, the digital device 102, and/or the application providing the request) as well as categorical classifications for a desired wine (e.g., red wine). In some embodiments, the wine request module 404 generates a wine request including a type of food or other information that may assist in the determination of a selected wine or assist in the ranking of wines.

The wine categorical classification module 406 may provide a pull down menu or other selection options to assist the user in selecting relevant information that may affect wine selection and/or ranking of wines. As discussed herein, a user is not required to be sophisticated, rather, the user may have a general appreciation of wine. The wine categorical classification module 406, may provide the user with a vocabulary to help the user identify the desired wines. Selections provided by the wine categorical classification module 406 may be incorporated within the wine request by the wine request module 404.

The location module 408 may provide location information within the wine request provided by the wine request module 404. In various embodiments, the user may provide a location, such as restaurant, winery, or wine store information (e.g., identifying the restaurant, winery, or wine store), within the wine request. The wine request module 404 may provide the wine request, including the location, to the wine ranking system 108.

In various embodiments, the wine ranking system 108 may select wines based on the user's wine proxy and the categorical classifiers discussed herein. The wine ranking system 108 may select a subset of selected wines based on the location information (e.g., wines that are available at the location identified in the wine request). The subset may be ranked as discussed herein.

The update module 410 may be configured to generate and provide an update request to the wine ranking system 108. In various embodiments, the update module 410 and/or the GUI module 402 provides an interface to allow the user to input an identifier which identifies a previously consumed wine. The interface may include a field for the user to input the name of the wine. In some embodiments, the interface may include a list of possible wines (e.g., via a pull down menu or with radio buttons) or a grouping of fields and lists (e.g., a field for the name of the wine and pull down menus for the vintage and varietal). The update module and/or the GUI module 402 may also provide the user with a selection of options to score or otherwise rate the wine (e.g., 1-5 stars). Those skilled in the art will appreciate that the update module 410 may provide the wine ranking system 108 with any information to update the user database.

In various embodiments, the update module 410 may update the user database and/or update the wine proxy locally utilizing methods described herein.

The wine selection and ranking module 412 is configured to receive a wine selection and/or ranking from the wine ranking system 108. In various embodiments, the wine ranking system 108 provides wine selections and/or rankings in response to a wine request received from the wine request module 404. The wine selection and ranking module 412 may retrieve the wine selections and/or rankings received from the wine ranking system 108 and provide the results to the user. Those skilled in the art will appreciate that a single wine selection received from the wine ranking system 108 may be termed a wine recommendation.

In some embodiments, the wine selection and ranking module 412 may provide pricing and/or availability information to the user. For example, once wines are selected and ranked, the wine selection and ranking module 412 and/or the wine ranking system 108 may retrieve availability and/or pricing information for the ranked wines (or the wines ranked in the top ten). Pricing information may be retrieved from any source including retail stores, distributors, or collected information by the wine ranking system 108. Further, the wine selection and ranking module 412 may provide availability information to the user based on location information from the location module 408, the digital device's 102 location, location information provided in the user registration (e.g., based on state, city, or zip code), or general availability.

In some embodiments, the GUI module 402 may provide a preference ratio based on price and ranking. For example, the GUI module 402 may display highly ranked wines that are available under $20 with different colors, animations, a score (e.g., similar to a PE ratio in a stock), or other indicator that may encourage the user to try the wine, even if the wine is not identified as the highest ranked wine based on the user's historical wine characteristic preferences.

The local database 414 may comprise all or part of the consumer wine preference profile or user wine database. In some embodiments, the local database 414 may store information that may be used by the update module 410 (e.g., past wine preferences, past wine tried, purchase history, or the like). In one example, the update module 410 may provide update information periodically. For example, the update module 410 may provide update information after a predetermined duration, at predetermined times, or after a predetermined amount of information is gathered. In this example, information may be stored in the local database 414 at least until the update module 414 provides the update request to the wine ranking system 108.

In some embodiments, one or more of the functions described herein may be performed on the wine ranking system 108. Those skilled in the art will appreciate that the functions described herein may be performed by different devices in any number of ways.

Figure 5:
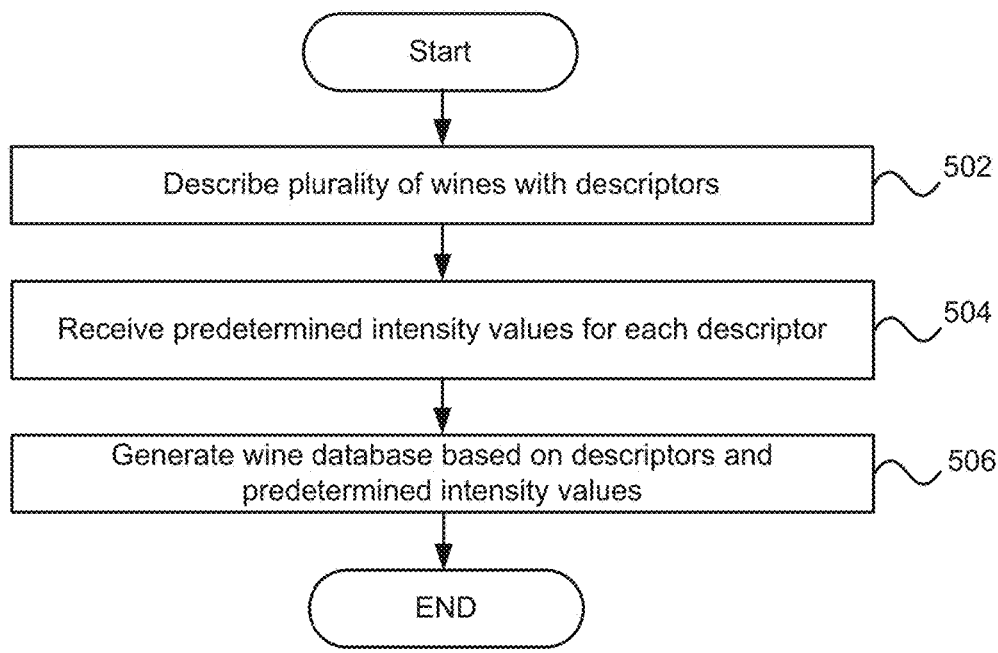
FIG. 5 depicts a flowchart of a method for generating a wine database, according to some embodiments.

FIG. 5 is a flowchart of a method for generating a wine database in some embodiments. By utilizing a panel of experts and/or trained individuals utilizing a common set of descriptors, individual taste preferences and other subjectivity may be reduced. Further, the collective scoring of the descriptors by the trained experts and/or individuals based on observation allows for objective weighting of the descriptors. As a result, a wine database may be generated and utilized to more accurately select and rank wines based on the user's experiences and tastes.

In step 502, a plurality of wines are described utilizing descriptors. In various embodiments, a common set of descriptors (e.g., a corpus of descriptors) may be identified based on different wine characteristics (e.g., acidity, tannins, structure, alcohol, terroir, and the like). The common set of descriptors may be used to describe all wines. For example, each wine may be associated with different intensity values associated with the different descriptors. As such, all wines may be commonly scored. The descriptors may be determined in any number of ways. Further, there may be any number of descriptors. In some embodiments, there are twenty-seven different descriptors that may be associated with intensity values to describe one wine.

Those skilled in the art will appreciate that the common set of descriptors may be defined using any methodology. For example, descriptors may be identified and included in the set based on common experience of the experts, ease of communication, and/or utility of meaning.

In step 504, the wine description module 202 is configured to receive predetermined intensity values for each descriptor. In some embodiments, experts or other individuals are trained to utilize the common set of descriptors as well as a scale for intensity values. Once trained, the experts and/or other individuals may taste a variety of different wines and individually assign intensity values for each descriptor associated with each wine. Once the intensity values for the descriptors associated with one or more wines is determined, the wine description module 202 may receive the intensity values. For example, the wine description module 202 may directly receive the intensity value data and/or tasting notes (e.g., the wines tasted, descriptors, and/or the assigned intensity values) from the experts and/or individuals. The wine description module 202 may be configured to translate the tasting notes from the experts and/or individuals into intensity values using NLP as discussed herein.

In some embodiments, the intensity values are averaged or combined in any number of ways. In various embodiments, the intensity values are not averaged but are maintained separately until a sufficient amount of information for each wine is gathered and then the information regarding the respective wine may be averaged or otherwise combined.

In step 506, the wine description module 202 generates a wine database based on the common set of descriptors and the predetermined intensity values (i.e., the intensity values provided by the experts and/or individuals described herein). In various embodiments, the wine description module 202 generates any number of databases or other data structures that contain any number of vectors associating intensity values with wine descriptors and/or wine identifiers.

Those skilled in the art will appreciate that the wine database may be continuously updated based on new tastings of previously tasted wines by experts and/or individuals. In this example, one or more experts may taste a previously tasted wine and provide intensity values that may be combined and/or added with the previous intensity values (e.g., previous intensity values of a particular descriptor may be combined with the new information and the average recalculated).

In some embodiments, the wine description module 202 may age wine and/or information regarding previous tastings. Those skilled in the art will appreciate that certain wines may improve or otherwise change over time. The wine description module 202 may apply less weight to previous tasting information (e.g., apply less weight to previous intensity values associated with a previous wine tasting past a predetermined duration of time) and apply more weight to current tasting information (e.g., apply equal or increased weight to intensity values associated with a more current wine tasting). In some embodiments, the wine description module 202 may be configured to reduce weights of some intensity values associated with descriptors that tend to reduce over time and, similarly, may be configured to increase weights of some intensity values associated with descriptors that tend to increase over time).

Figure 6:
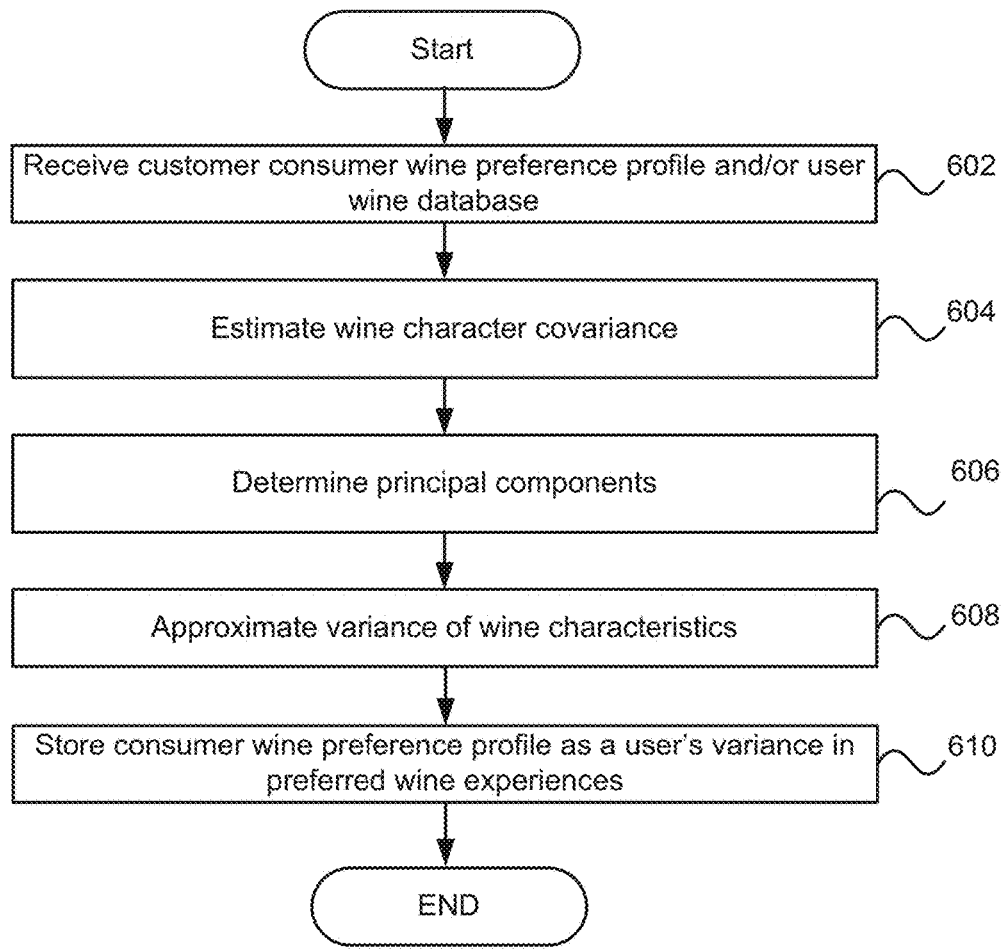
FIG. 6 depicts a flowchart of a method for training a user database, according to some embodiments.

FIG. 6 is a flowchart of a method for training a user database in some embodiments. Those skilled in the art will appreciate that, unlike systems in the prior art, various embodiments described herein rely on objective descriptions of wines in terms of descriptors.

In step 602, once the user has registered with the wine ranking system 108, the wine ranking system 108 may receive one or more customer wine characteristics and/or preferences. For example, the user may provide information regarding past wines that the user has tasted. In some embodiments, the user may provide only general information (e.g., categorical classifications) including wine type, varietal, or other general information. The user provide other categorical classifications including, for example, specific wine information such as wine maker, winery, specific name, vintage, or any other information.

In step 604, the wine description module 108 may estimate wine character covariance. For example, a wine character covariance may be an N×N matrix (where N is the number of descriptors) for the wines identified in step 602. In some embodiments, if the user provides sufficient information, intensity values may be included for sufficiently identified wines (e.g., from the wine database). Intensity values may be estimated based on the wine information provided the user (e.g., based on wines that are information provided by the user such as a similar wine maker, winery, specific name, region of wine, vintage, or other information).

The wine character covariance may be based on the total number of wines identified by the user, the wine mean character intensity vector computed for all N characters across the identified wines, and character intensity values for each of the wines. As discussed herein, may be an estimate of the true covariance of all wines (including those that are not in the database).

In step 606, the wine description module 108 determines principal components. The principal components of the training database is determined by solving the Eigenvalue problem for N wine characters utilizing on a matrix that contains N Eigenvectors (i.e., principal components) of the de-correlated user wine parameter basis.

In step 608, the wine description module 108 approximates variance of wine characteristics. For example, the wine description module 108 may pick a subset of Eigenvectors to recue ambiguity or uncorrelated noise. The new Eigen-characters may approximate variance of wine characteristics. The calculated variance may be utilized as the user's individual "wine proxy" as the set of Eigen-characters, mean character vector, and relative importance values (i.e., filter weights).

In step 610, the wine description module 202 stores the variance (e.g., the user's "wine proxy") within the user's preference profile. The wine description module 202 may store the information within the user profile database 212, the wine database 214, and/or on the user's digital device (e.g., digital device 102).

Figure 7:
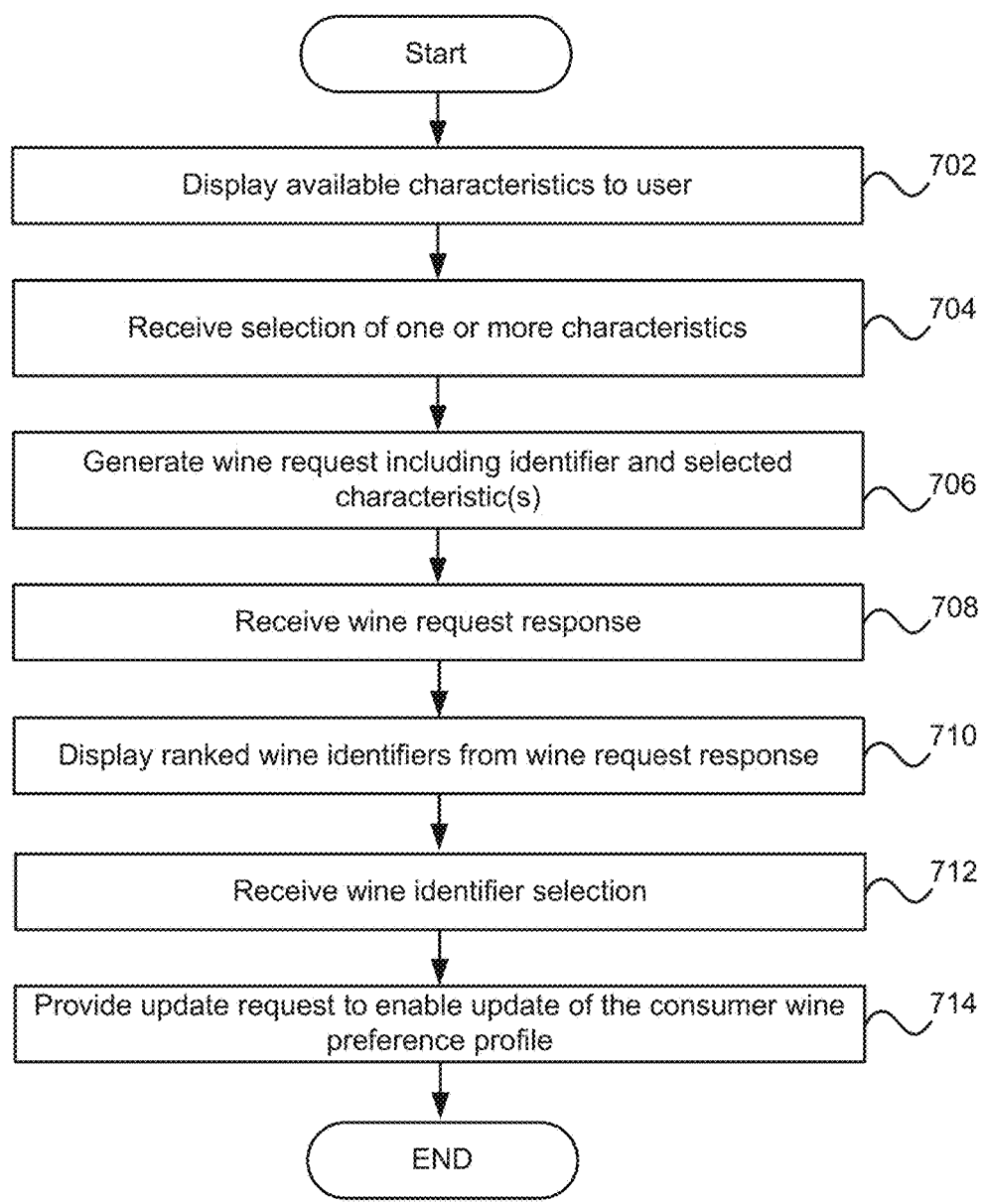
FIG. 7 depicts a flowchart of a method for a user receiving ranked wines on the user's digital device, according to some embodiments.

FIG. 7 is a flowchart of a method for a user receiving ranked wines on a user's digital device 102 in some embodiments. In various embodiments, the user may indicate a desire to receive a list of ranked wines. The user may engage an application or contact the wine ranking system 108 to provide a wine request. In step 702, the GUI module 402 displays available descriptors and/or categorical classifications to the user. In one example, the user may be encouraged to select one or more of the provided categorical classifications to indicate the type of wines to be ranked.

For example, the GUI module 402 may provide a list of descriptions of wines including possible wine regions of preferred wines, color of wines, common vintages, or the like. In some embodiments, a limited set of categorical classifications may be provided to the user to train the user wine database. The wine ranking system 108 may comprise translators to associate the user's selected categorical classifications with any number of descriptors and/or related intensity values. In some embodiments, the intensity values may be neutral until or unless the user indicates a degree of preferences (e.g., number of stars or other indication of preference). In some embodiments, the GUI module 402 provides fields that the user may provide text input identifying descriptors and/or categorical classifications.

In step 704, the GUI module 402 may receive a selection of one or more categorical classifications from the user. In step 706, the wine request module 404 may generate a wine request including an identifier (e.g., identifying the user, a related user account, and/or the device to receive the wine ranking). The wine request may also include the categorical classifications from the user. In some embodiments, the wine request includes the contents of fields input by the user.

In step 708, in response to the wine request, the wine selection and ranking module 412 may receive a wine request response in response from the wine ranking system 108. The wine request response may comprise a recommended wine (e.g., a selected wine) or a list of ranked wines based on the provided information as well as the previously provided information from the user. The list may comprise wine identifiers ranked by the user's preference as represented by the user wine database.

In step 710, the GUI module 402 displays ranked wine identifiers (e.g., the ranked list) from the wine request response. In various embodiments, the GUI module 402 may reorder the list or re-rank the list based on availability, location of the digital device, price, or any preferences not provided by the wine request module 404. In some embodiments, the GUI module 402 allows the user to filter the ranking in any number of ways.

In step 712, the update module 410 may receive a user's wine identifier selection (e.g., a selection of at least one of the ranked wines) indicating that the user has chosen to try the selection. In step 714, the update module 410 may provide the selection to the wine ranking system 108 to update the user's wine database and/or wine proxy. In some embodiments, the user may provide a score (e.g., star rating) to a wine at the time the update module 410 provides the selection. Alternately, the user may provide the scoring at a later time (e.g., the wine ranking system 108 may provide a message requesting that the user provide a score to the wine identified by the update module 410).

In various embodiments, the user may update the user wine database and/or consumer wine preference profile utilizing a card such as a loyalty card and/or credit card during purchases. For example, a user may provide such a card during wine purchases. An employee at a restaurant, retail establishment, winery, or the like may scan the card. As a result, the wine ranking system 108 may receive an indication of wines purchased by the user during the transaction. The wine ranking system 108 may updated the user's consumer wine preference profile based on the information. In some embodiments, the wine ranking system 108 may provide the user with an email or other communication requesting that the user provide a score or other indication of user preference which may be used to weight intensity values associated with the purchased wine(s). In some embodiments, if no response is received, the wine ranking system 108 may apply a neutral weight or disregard the purchases.

Those skilled in the art will appreciate that the purchase may not be limited to cards, but may include providing a code or other identifier during online purchases. Digital passports or wallets (e.g., possibly utilizing NFC communications) may similarly be used to provide purchase information to the wine ranking system 108. Moreover, in some embodiments, an application may be provided that allows a user's mobile device to scan bar codes and/or provide photographs of labels to allow the wine ranking system 108 to update the consumer wine preference profile. In this example, the wine ranking system 108 may include a bar code database that allows the wine ranking system 108 to identify the related wine. Similarly, the wine ranking system 108 may include a scanning module configured to process images from smartphone cameras to identify wines. Various labels and/or label information may be stored within one or more databases. The label information may be utilized to identify at least portions of a label to allow for matching (e.g., utilizing hashed information of the labels for matching) and wine identifications.

Figure 8:
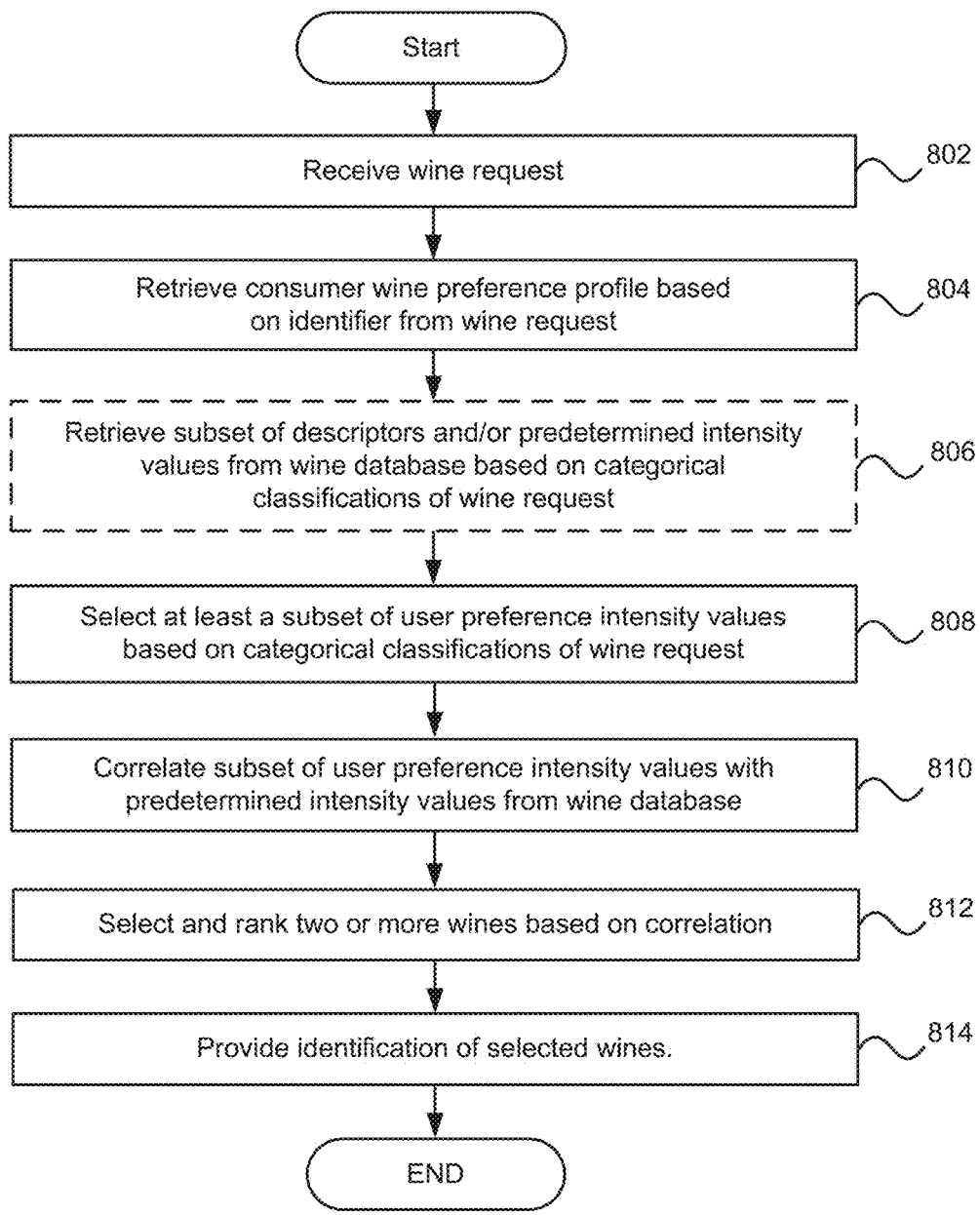
FIG. 8 depicts a flowchart of a method for providing ranked wines to the user's digital device in response to a wine request, according to some embodiments.

FIG. 8 is a flowchart of a method for providing ranked wines to the user's digital device 102 in response to a wine request in some embodiments. In step 802, the wine ranking system 108 receives a wine request from the digital device 102. In various embodiments, the ranking module 206 receives the request. The request may comprise an identifier that identifies the user (e.g., username, password, and/or account number) or the digital device 102.

In step 804, the ranking module 206 may retrieve the consumer wine preference profile based on the identifier from the wine request. The consumer wine preference profile may comprise the user's precalculated wine proxy and/or other information. In some embodiments, the ranking module 206 retrieves the user's wine database based on the consumer wine preference profile.

In optional step 806, the ranking module 206 may retrieve a subset of descriptors and/or predetermined intensity values from the wine database based on information contained in the wine request. For example, the user may include location information and/or categorical classification information within the wine request. The ranking module 206 may retrieve a subset of descriptors and/or predetermined intensity values from the wine database that are consistent with the location information (e.g., available at the user's current location) and/or categorical classification (e.g., white wine from France).

In some embodiments, the ranking module 206 may retrieve all descriptors and predetermined intensity values from the wine database and correlate the information with the user's wine proxy (e.g., the user preference intensity values). After wines are selected based on the correlation, the ranking module 206 may filter the results to remove wine that are not associated with the location and/or categorical classifications of the wine request. In some embodiments, the filtering may occur after the wines are ranked. In some embodiments, the entire selection and/or ranking may be provided to the digital device 102 of the user which performs the filtering step.

In step 808, the ranking module 206 may retrieve at least a subset of the user preference intensity values based on the categorical classifications within the wine request. For example, the ranking module 206 may select only those user preference intensity values associated with wines that meet the categorical classifications. In some embodiments, the ranking module 206 retrieves all of the user preference intensity values and/or the user's wine profile for all wines identified by the user.

In step 810, the ranking module 206 correlates the user preference intensity values with predetermined intensity values from the wine database as retrieved in step 806. The ranking module 206 may select any number of wines based on the correlation. The correlation process is described herein.

In step 812, the ranking module 206 selects and ranks two or more wines based on the correlation. As discussed herein, the system may rank wines based on an objective assessment calibrated to the user's preferences based on the user's personal experience. In step 814, the ranking module 206 may provide identification(s) of the selected wines (e.g., a ranked list) to the digital device 102.

Figure 9:
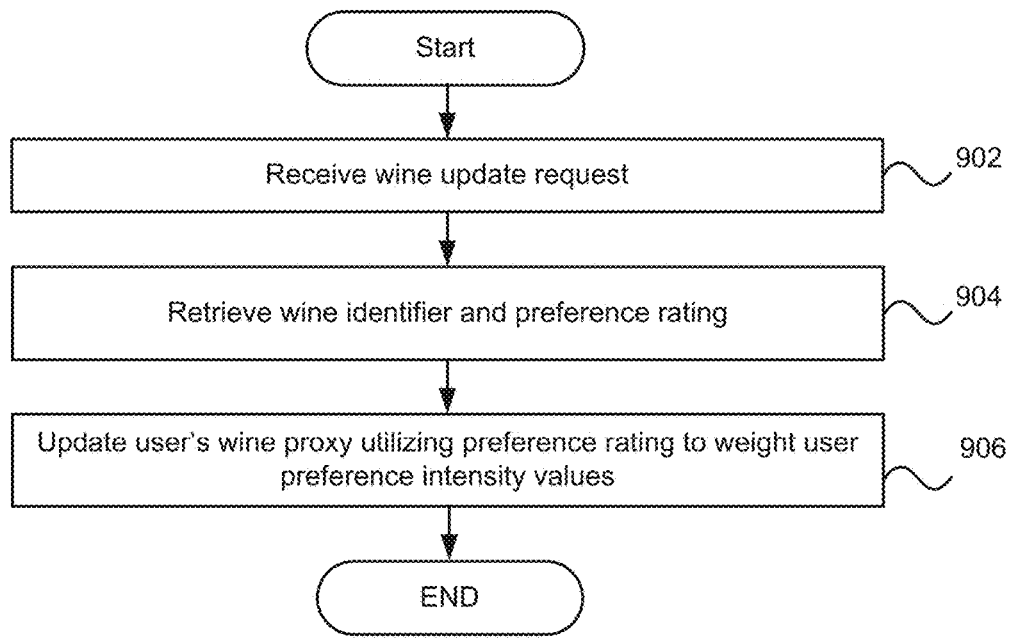
FIG. 9 depicts a flowchart of a method for updating a user wine database, according to some embodiments.

FIG. 9 is a flowchart of a method for updating a user wine database in some embodiments. In various embodiments, the wine ranking system 108 receives a wine update request from a digital device 102. The wine update request may comprise a wine identifier and/or a preference rating (e.g., a score of 1-5 indicating the user's preference or enjoyment of the identified wine). Those skilled in the art will appreciate that there may be any range of ratings (e.g., 1-4 stars, 1-10 points, or the like). Further, those skilled in the art will appreciate that rankings may be any numerical or non-numerical value.

In step 904, the update module 208 may retrieve the wine identifier and the preference rating. The update module 208 may incorporate the new observations into the user's wine proxy. In some embodiments, the process is similar to a mathematical regression whereby a new lambda is generated (see equation 7 herein) which updates the user's lamba for future rankings in step 906. The wine average <ch> is also updated. As a result, as new wines are tried and added to the system, the rankings, selections, and/or recommendations of the wine ranking system 108 may improve.

Those skilled in the art will appreciate that systems and methods described herein may be applied outside of wine. In various embodiments, systems and methods described herein may be utilized to recommend and/or rank food and wine pairings, foods in general, or the like. In some embodiments, a "pseudo-wine" may be calculated based on shared descriptors between wines and food. For example, there may be eight descriptors that related to food and wine. The eight descriptors may be used to describe the characteristics of the food in question. Different foods with different intensities (i.e., intensity values) related to descriptors may be used to create a "food proxy" in a manner similar to the construction of the wine proxy (e.g., utilizing the wine descriptors and associated intensity scores for the food(s) of interest). Similarity between the food proxy and wines in the wine database may be utilized to provide a wine pairing recommendation. Those skilled in the art will appreciate that any number of descriptors may be utilized to describe food.

In one example, experts and/or trained individuals may establish or may utilize a common parameter set of descriptors to describe foods. The experts and/or trained individuals may taste a wide variety of foods and/or types of one or more foods (e.g., meats). The experts and/or trained individuals may score intensity values based on the wine descriptors to describe the food. This information may be used to translate a request for a food and wine pairing (e.g., a request to match rib eye steak and wine) into a food proxy as described herein that may be utilized for the similarity assessment, selection, and/or ranking.

Various embodiments described herein may be utilized to apply to foods (e.g., olive oils or combinations of different foods such as different meats combined with other non-meat consumables) or other goods. For example, the ranking module 206 of the wine ranking system 108 described with regard to FIG. 2 may be configured to identify foods of interest to users based on descriptors and user preference intensity values from an associated user database (e.g., user profile). Similar to the wine method, the ranking module 206 may take parametric information (characters and intensities) from the user training database, perform a spatial correlation across parameters and food entries, and use the resulting statistical correlations to mathematically reduce the parameter set to a limited number of new uncorrelated variables which, taken in linear combination, may uniquely define the user's food preference (i.e., the user food proxy).

Describing an approach utilizing principal component analysis as one example, the mathematical procedure transforms, a number of correlated variables (i.e., food characters in this case) into an equal number of uncorrelated variables (vectors) (principal components) while maintaining full variance and ordering the components by contribution. The resulting transformation may be such that the first principal component represents the largest amount of variability (i.e., has the largest weight), while each successive component may account for at least some of the remaining variability.

For example, a training database, similarly generated as that of the training database for the wine example, has M foods and that each food has N characters (e.g., descriptors). A food character covariance (N×N) matrix then can be estimated from the training database according to the approximation:

$$C = 1/M \sum_{i=1}^{M} [ch_i - \langle ch \rangle]^T [ch_i - \langle ch \rangle] \quad (8)$$

where M is the total number of foods in the training database, $\langle ch \rangle$ is the food mean character intensity vector computed for all N characters (i.e., intensity values) across all M foods, and $ch_i$ is each character intensity vector (length=N) for each of the M foods in database.

Since C is a symmetric semi-positive definite matrix, the principal components of the training database may be computed by solving the Eigenvalue problem for the N food characters:

$$C\lambda = \lambda V \quad (9)$$

The matrix V contains the N Eigenvectors (i.e., principal components) of the de-correlated user food parameter basis. The vector $\lambda$ contains the N Eigenvalues (principal component weights representing the relative importance of each individual Eigen-character, $V_i$, in describing the user's food "type").

The ranking module 206 may pick a small or smallest subset, P<<N, of Eigenvectors from this base that adequately account for most of our food character variability according to the criteria, e.g.:

$$\Sigma \lambda_i [1:P]/\text{trace}[C] \geq 70\%. \quad (10)$$

Whether the system uses all N or just P components of the de-correlated basis, these new food Eigen-characters approximate the variance (and to a lesser extent the correlation) of food characteristics follow the mathematical form:

$$\text{Var}[\text{food}]_{user} = \langle ch \rangle + \lambda_{user} V \quad (11)$$

In this context, the larger each $\lambda_i$, the more important (and more correlated across the database) each component, $V_i$, may be in describing the likes of the user for the particular set of foods in the training.

As similarly described herein, equation 4 may project the food characters into a new mathematical space (i.e., the user "proxy space") that exploits the statistical relationship between different food characters.

Those skilled in the art will appreciate that the largest Eigenvalue ($\lambda_1$) in equation 4 may represent the least distinguishing proxy character for food, because all food may share this character (this $v_1$ represents the maximum correlation between all wines in the subset), while the smallest Eigenvalue ($\lambda_N$) may represent the most distinguishing proxy character, because it is correlated between foods less than all other food characters—it may be the most unique Eigen-character.

In some embodiments, matrix V is consistent with equation 2 and specific to the user. The statistical proxy may include the user's $\lambda$ values, V, and CH. The ranking module 206 may utilize this process to create a basis for initial ranking of food.

Once the user proxy is computed, future user food requests may be filtered by the operator V in order to transform all foods from a new "dynamic" database into the user's proxy space. To this end, equation 4 may allow the user to specify new food descriptors they are currently interested in having the system rank. The update module 208 then uses this information to build a dynamic database which is distinct from the training discussed herein. In one example, the update module 208 updates the existing user database with foods to those of current interest. Then the update module 208 "projects" each food (e.g., the update module 208 projects each wine's characteristics as defined herein) contained in this dynamic database to the user proxy space by solving the small (P×P) principal component (PC) problem:

$$\lambda_{food_i} = [ch_{food_i} - \langle ch \rangle] V \quad (12)$$

Here, $\lambda_{food}$ is each of i foods PC defined by each character vector, $ch_{food}$, contained in the dynamic database and filtered by the Eigen-vector operator V.

Then the system can rank (in either ascending or descending order) all i foods from the dynamic database according to their mathematical similarity/difference, $S_i$, in the proxy space to the previously defined user food proxy values, $\lambda_{user}$, from equation 4:

$$s_i = \Sigma_{i=1}^{P} |\lambda_{user} - \lambda_{food_i}| \quad (13)$$

In various embodiments, every food in a database that matches a search may be assessed. In one example, foods are retrieved that match a search based on a user food request and then the related descriptors may be converted to a mathematical space to look for similarity with the statistical proxy.

Retrieved (e.g., selected) foods may be ranked based on the similarity to the statistical proxy. The identifiers (e.g., labels, names, or the like) of the foods may be ranked. In some embodiments, when the ranked foods are provided, food identifiers, location where the food is available, degree of similarity, and/or pricing may be provided to the user. In some embodiments, the ranking module 206 may provide a value number based on price and fitness.

As discussed herein regarding wine, the user food proxy may then be updated to reflect these user feedback ratings by solving a regression problem (mathematical fitting problem). This technique (which has many embodiments) may incorporate new observations (user ratings) into the user proxy vector (λ) via the general mathematical form:

$$[\lambda_{update}] = [\lambda R_w \lambda^T + \epsilon I]^{-1} \lambda^T R_w C \quad (14)$$

As discussed herein, $R_w$ is a diagonal weighting matrix containing the relative user ratings for each wine, I is identity matrix, $\epsilon$ is a damping term for stabilization, C is the vector containing the sum of each wine vector residual (projected into the proxy space) for all wines (stored by the system from the previous training and ranking steps), and λ is per equation 5 for each wine. This updated $\lambda_{update}$ is used to update $\lambda_{user}$ ($\lambda_{new} = \lambda_{update}$), is stored by the system, and replaces $\lambda_{user}$ in all future Step 4 rankings. The average $\langle ch \rangle$ is also updated accordingly from the composite list of all wines rated and in the dynamic database. Then as the user tries/rates more wines, the system will better adapt to the user's likes/dislikes and rankings will increase in accuracy going forward.

In various embodiments, the food ranking system 108 provides a ranking of foods based on a subset of the foods in the food database. For example, the user may request foods that are available based on location (e.g., restaurant, wine bar, or the like) and/or based on categorical classifications (e.g., meat, vegetable, texture, or consistency). In some embodiments, the system may select a subset of the wine database to correlate with the user's food proxy.

Those skilled in the art will appreciate that systems and methods described herein may not be limited to consumable good such as food and drink, but may be extended to ranking and/or recommendation of coupons or the like.

Figure 10:
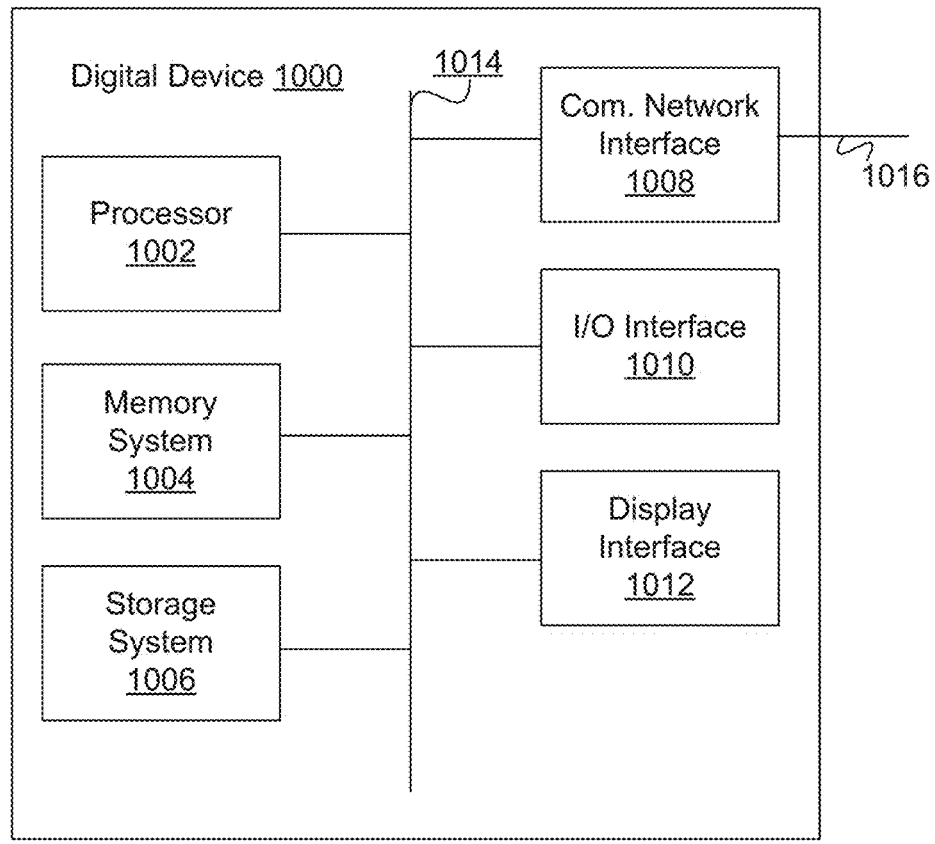
FIG. 10 depicts a block diagram of an exemplary digital device, according to some embodiments.

FIG. 10 depicts an exemplary digital device 1000 according to some embodiments. The digital device 1000 comprises a processor 1002, a memory system 1004, a storage system 1006, a communication network interface 1008, an I/O interface 1010, and a display interface 1012 communicatively coupled to a bus 1014. The processor 1002 may be configured to execute executable instructions (e.g., programs). In some embodiments, the processor 1002 comprises circuitry or any processor capable of processing the executable instructions.

The memory system 1004 is any memory configured to store data. Some examples of the memory system 1004 are storage devices, such as RAM or ROM. The memory system 1004 may comprise the RAM cache. In various embodiments, data is stored within the memory system 1004. The data within the memory system 1004 may be cleared or ultimately transferred to the storage system 1006.

The storage system 1006 is any storage configured to retrieve and store data. Some examples of the storage system 1006 are flash drives, hard drives, optical drives, and/or magnetic tape. In some embodiments, the digital device 1000 includes a memory system 1004 in the form of RAM and a storage system 1006 in the form of flash data. Both the memory system 1004 and the storage system 1006 comprise computer readable media which may store instructions or programs that are executable by a computer processor including the processor 1002.

The communication network interface (com. network interface) 1008 may be coupled to a data network (e.g., communication network 106) via a link. The communication network interface 1008 may support communication over an Ethernet connection, a serial connection, a parallel connection, or an ATA connection, for example. The communication network interface 1008 may also support wireless communication (e.g., 802.11 a/b/g/n, WiMAX). It will be apparent to those skilled in the art that the communication network interface 1008 may support many wired and wireless standards.

The optional input/output (I/O) interface 1010 is any device that receives input from the user and output data. The optional display interface 1012 is any device that may be configured to output graphics and data to a display. In one example, the display interface 1012 is a graphics adapter.

It will be appreciated by those skilled in the art that the hardware elements of the digital device 1000 are not limited to those depicted in FIG. 10. A digital device 1000 may comprise more or less hardware elements than those depicted. Further, hardware elements may share functionality and still be within various embodiments described herein. In one example, encoding and/or decoding may be performed by the processor 1002 and/or a co-processor located on a GPU.

In various embodiments, a system accurately predicts tastes and sensations of users who experience wines. A panel of people who have experience with wines may be provided with a variety of wines in a relevant order. The order may be related to a specific flight and/or pairings. The panelists' tastes and sensations may be recorded using data entry techniques, such as techniques involving Scantron® sheets, punch cards, and electronic devices. The tastes and sensations may correspond, for example, to descriptors associated with one or more properties of wine. Once recorded, a multitude of panelists' responses may be evaluated to determine global intensity values of each descriptor. Using statistical measures, the global intensity values may approximate objective measures of these descriptors.

A panelist's individual score(s) (e.g., a panelist's intensity value) associated with a descriptor may be excluded if the score(s) significantly deviate from global intensity scores, deviate from the panelist's scores related to similar descriptors, or suggest the panelist is unable to accurately score the wine descriptors. Further, in some embodiments, a panelist's bias may be detected and accommodated (e.g., corrected and/or updated) by normalizing intensity scores provided by the panelist. The updated global intensity scores may be used to populate the user wine database (e.g., the wine database 214 in FIG. 2) as discussed herein.

Figure 11:
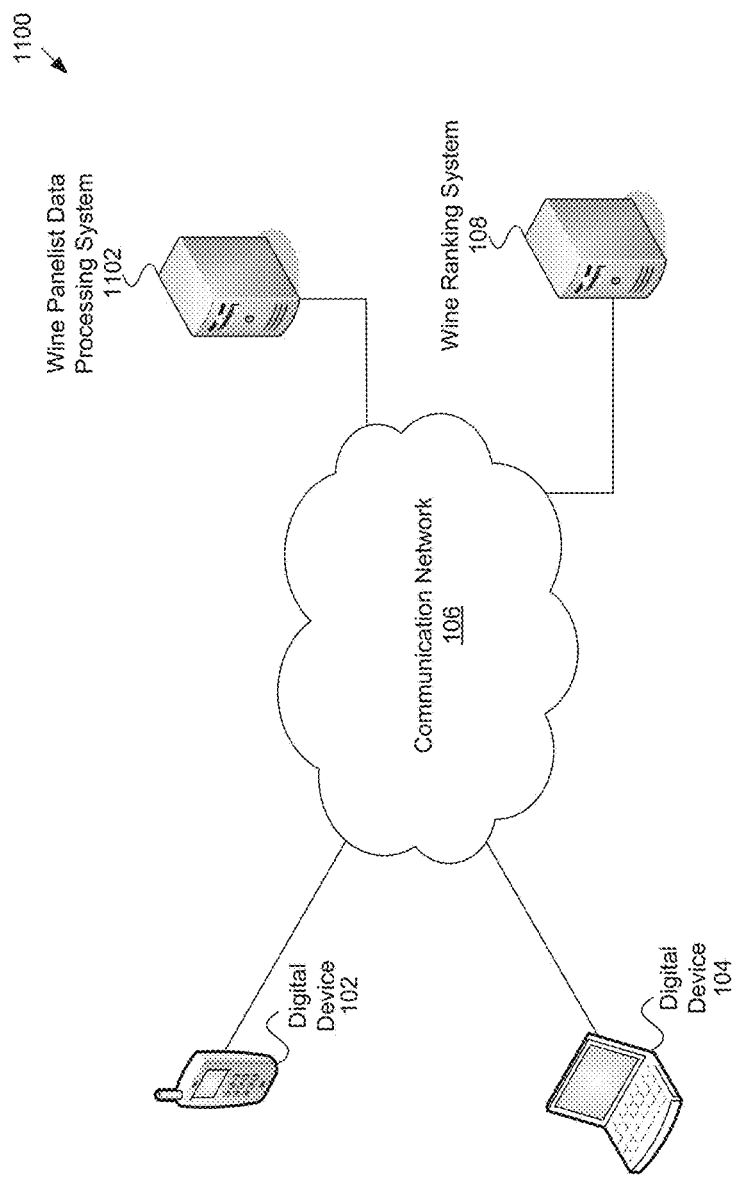
FIG. 11 depicts an environment that facilitates identifying properties of wines and matching wines with the preferences of users.

FIG. 11 depicts an environment 1100 that facilitates identifying properties of wines and matching wines with the preferences of users. The environment 1100 includes a first digital device 102, a second digital device 104, a communication network 106, a wine ranking system 108, and a wine panelist data processing system 1102. The first digital device 102, the second digital device 104, and the wine ranking system 108 are coupled to the communications network 106. In various embodiments, each of the first digital device 102, the second digital device 104, the communications network 106, and the wine ranking system 108 corresponds to its respective counterpart in FIG. 1.

The wine panelist data processing system 1102 may be coupled to the communications network 106. The wine panelist data processing system 1102 may be implemented using a digital device. As discussed, a digital device is any device with memory and a processor. The wine panelist data processing system 1102 may comprise a mobile or stationary digital device such as, but not limited to: a desktop computer, a laptop computer, a tablet computing device, a smartphone, a networked server, a dedicated server, and/or portions of a distributed server. The wine panelist data processing system 1102 may include any number of digital devices (e.g., servers). In various embodiments, the wine panelist data processing system 1102 comprises an application that communicates with the wine ranking system 108. For example, the wine panelist data processing system 1102 may comprise a standalone computer application that is executed on the wine panelist data processing system 1102, and/or portions of a web page that are displayed in a container application (e.g., an Internet browser or a sandboxed computing environment) on the wine panelist data processing system 1102.

In some embodiments, wine panelist data processing system 1102 comprises a mobile application. In some implementations, the wine panelist data processing system 1102 comprises or is associated with a web server that provides wine recommendations and/or rankings to the digital device 102 via the Internet.

The wine panelist data processing system 1102 may send data to and receive data from the wine database 214, shown in FIG. 2 and discussed further herein. In some embodiments, the wine panelist data processing system 1102 provides to the wine database 214 measures (e.g., intensity scores) of wine descriptors (e.g., acidity, alcohol, aroma intensity, baking spices, berries, Brett, candied fruit, citrus, dried fruits jam, earthy, flavor intensity, floral, green notes, hay straw, lees butter, length of finish, mineral, native grapy, palate weight, pepper, perceived sugar, petrol, sweet aromas, texture, tree fruits, tropical fruits melon, woody) for various wines.

As discussed herein, a wine identifier identifies a particular wine (e.g., Robert Foley Claret 2010). A wine descriptor is a characteristic of a wine. Each wine descriptor may have an associated intensity score. The intensity score represents a degree of actual and/or perceived presence of the wine descriptor. An intensity score may be defined as a certain range. For example, an intensity score may be zero to six, with zero indicating that a wine characteristic related to the wine descriptor is not present and a six being a maximum amount of the wine characteristic related to the wine descriptor. Those skilled in the art will appreciate that there may be any range or representation of intensity values.

In some embodiments, the wine panelist data processing system 1102 obtains intensity values associated with wine characteristics from one or more panels of wine tasting panelists. The panelists in a panel may have some level of expertise in recognizing the characteristics of wines. For example, in some embodiments, the wine panelist data processing system 1102 obtains intensity values of wine characteristics from wine experts who have expertise to recognize the characteristics of wines. The wine experts may have been formally trained in recognizing the characteristics of wines, may be able to recognize the characteristics of wines based on their experience, and/or may be qualified to recognize the characteristics of wines in some other way.

The wine panelist data processing system 1102 may receive intensity values from panelists of similar or different levels of expertise in recognizing the characteristics of wines. In some embodiments, the wine panelist data processing system 1102 receives intensity values from panelists who have expertise in recognizing only a specific set of characteristics (e.g., only peppers, hay, and perceived sugar) of wines. Further, the wine panelist data processing system 1102 may receive intensity values from different panels of wine experts for different varieties of wines. The wine of a panel may be ordered in accordance with the method shown in FIG. 40.

In various embodiments, the wine panelist data processing system 1102 receives intensity values from panels that are likely to produce subjective information related to wine characteristics. Panels that are likely to yield statistically meaningful results may have a large number of panelists. In various embodiments, the wine panelist data processing system 1102 may only use panels having dozens, hundreds, or thousands of panelists.

Panels with a sufficiently large number of panelists may produce information that follows a Gaussian or near-Gaussian distribution. Panels with a sufficiently large number of panelists may utilize means, deviations, and/or other statistically relevant properties related to intensities of wine characteristics in a meaningful manner. By utilizing a sufficiently large number of panelists, it is less likely that the overall intensity values (e.g., global intensity values) will be skewed by inaccurate, imprecise, and/or biased assessments of a single panelist or a handful of panelists.

In various embodiments, the wine panelist data processing system 1102 receives intensity values from panels of "blind" panelists. For example, panels may include panelists who are unaware of a specific variety, vintage, geographic locale, label, price, or producer (i.e., winery) of wine that is being tested. Although the panelists in a panel may have experience in recognizing flavors, they need not know which variety or the exact flavors in a variety of wine being tested when the variety is being tasted.

Panelists may be required to repeat sampling of one or more wines. For example, each panelist may be required to sample Robert Foley Claret 2010 twice, three times, etc. Repeat sampling may indicate the consistency or inconsistency of one or more panelists. Adjusting global intensity values based on consistency may assist in ensuring that the information about wine characteristics from the panel is sufficiently precise and/or unbiased. In various examples, panels may be constituted according to Tables 2, 3, and 4 shown as follows:

TABLE 2

Example random sequence used for blind scoring

| Record | Number Sequence | Letter | Number | Scantron Code |
|---|---|---|---|---|
| 1 | 1 | A | 520 | A520 |
| 2 | 1 | B | 520 | B520 |
| 3 | 1 | C | 520 | C520 |
| 4 | 1 | D | 520 | D520 |
| 5 | 1 | E | 520 | E520 |
| 6 | 1 | F | 520 | F520 |
| 7 | 1 | G | 520 | G520 |
| 8 | 1 | H | 520 | H520 |
| 9 | 1 | I | 520 | I520 |
| 10 | 1 | J | 520 | J520 |
| 11 | 1 | K | 520 | K520 |
| 12 | 1 | L | 520 | L520 |
| 13 | 1 | M | 520 | M520 |
| 14 | 1 | N | 520 | N520 |
| 15 | 1 | O | 520 | O520 |
| 16 | 2 | A | 820 | A820 |
| 17 | 2 | B | 820 | B820 |
| 18 | 2 | C | 820 | C820 |
| 19 | 2 | D | 820 | D820 |
| 20 | 2 | E | 820 | E820 |
| 21 | 2 | F | 820 | F820 |
| 22 | 2 | G | 820 | G820 |
| 23 | 2 | H | 820 | H820 |
| 24 | 2 | I | 820 | I820 |
| 25 | 2 | J | 820 | J820 |
| 26 | 2 | K | 820 | K820 |
| 27 | 2 | L | 820 | L820 |
| 28 | 2 | M | 820 | M820 |
| 29 | 2 | N | 820 | N820 |
| 30 | 2 | O | 820 | O820 |

TABLE 2-continued

Example random sequence used for blind scoring

| Record | Number Sequence | Letter | Number | Scantron Code |
|---|---|---|---|---|
| 31 | 3 | A | 558 | A558 |
| 32 | 3 | B | 558 | B558 |
| . | . | . | . | . |
| . | . | . | . | . |
| . | . | . | . | . |
| 13335 | 889 | O | 128 | O128 |

TABLE 3

An example of Random-number-assignment worksheet

| | Day 1 | | | | Day 2 | | | | Day 3 | | |
|---|---|---|---|---|---|---|---|---|---|---|---|
| Varietal | Flight No. | Wine No. | Random No. | Varietal | Flight No. | Wine No. | Random No. | Varietal | Flight No. | Wine No. | Random No. |
| Dry Riesling | 1 | 1 | 160 | Chardonnay | 7 | 1 | 209 | Pinot Noir | 13 | 1 | 310 |
| Dry Riesling | 1 | 2 | 650 | Chardonnay | 7 | 2 | 899 | Pinot Noir | 13 | 2 | 541 |
| Dry Riesling | 1 | 3 | 667 | Chardonnay | 7 | 3 | 958 | Pinot Noir | 13 | 3 | 975 |
| Dry Riesling | 1 | 4 | 225 | Chardonnay | 7 | 4 | 587 | Pinot Noir | 13 | 4 | 977 |
| Dry Riesling | 1 | 5 | 791 | Chardonnay | 7 | 5 | 809 | Pinot Noir | 13 | 5 | 755 |
| Dry Riesling | 1 | 6 | 466 | Chardonnay | 7 | 6 | 796 | Pinot Noir | 13 | 6 | 970 |
| Dry Riesling | 1 | 7 | 969 | Chardonnay | 7 | 7 | 241 | Pinot Noir | 13 | 7 | 562 |
| Dry Riesling | 1 | 8 | 406 | Chardonnay | 7 | 8 | 304 | Pinot Noir | 13 | 8 | 954 |
| Dry Riesling | 1 | 9 | 963 | Chardonnay | 7 | 9 | 351 | Pinot Noir | 13 | 9 | 430 |
| Dry Riesling | 1 | 10 | 511 | Chardonnay | 7 | 10 | 636 | Pinot Noir | 13 | 10 | 625 |
| Pinot Noir | 2 | 1 | 984 | Cab. Sauvignon | 8 | 1 | 951 | Merlot | 14 | 1 | 547 |
| Pinot Noir | 2 | 2 | 994 | Cab. Sauvignon | 8 | 2 | 824 | Merlot | 14 | 2 | 992 |
| Pinot Noir | 2 | 3 | 965 | Cab. Sauvignon | 8 | 3 | 553 | Merlot | 14 | 3 | 713 |
| Pinot Noir | 2 | 4 | 217 | Cab. Sauvignon | 8 | 4 | 283 | Merlot | 14 | 4 | 897 |
| Pinot Noir | 2 | 5 | 850 | Cab. Sauvignon | 8 | 5 | 690 | Merlot | 14 | 5 | 998 |
| Pinot Noir | 2 | 6 | 730 | Cab. Sauvignon | 8 | 6 | 367 | Merlot | 14 | 6 | 588 |
| Pinot Noir | 2 | 7 | 853 | Cab. Sauvignon | 8 | 7 | 604 | Merlot | 14 | 7 | 971 |
| Pinot Noir | 2 | 8 | 538 | Cab. Sauvignon | 8 | 8 | 781 | Merlot | 14 | 8 | 269 |
| Pinot Noir | 2 | 9 | 996 | Cab. Sauvignon | 8 | 9 | 306 | Merlot | 14 | 9 | 286 |
| Pinot Noir | 2 | 10 | 747 | Cab. Sauvignon | 8 | 10 | 318 | Merlot | 14 | 10 | 391 |
| Flight no. 3 | | | | Flight no. 9 | | | | Flight no. 15 | | | |
| . | | | | . | | | | . | | | |
| . | | | | . | | | | . | | | |
| . | | | | . | | | | . | | | |
| Flight no. 6 | | | | Flight no. 12 | | | | Flight no. 18 | | | |

TABLE 4

An example of sample order with the 3-digit random number for a flight of 10 wines.

| Panelists | Randomized wine order for a flight of 10 wines serving 12 panelists | | | | | | | | | | Wine No. | Random No. |
|---|---|---|---|---|---|---|---|---|---|---|---|---|
| A | 253 | 181 | 880 | 479 | 498 | 238 | 266 | 363 | 484 | 490 | 1 | 490 |
| B | 181 | 479 | 253 | 238 | 880 | 363 | 498 | 490 | 266 | 484 | 2 | 484 |
| C | 479 | 238 | 181 | 363 | 253 | 490 | 880 | 484 | 498 | 266 | 3 | 266 |
| D | 238 | 363 | 479 | 490 | 181 | 484 | 253 | 266 | 880 | 498 | 4 | 498 |
| E | 363 | 490 | 238 | 484 | 479 | 266 | 181 | 498 | 253 | 880 | 5 | 880 |
| F | 490 | 484 | 363 | 266 | 238 | 498 | 479 | 880 | 181 | 253 | 6 | 253 |
| G | 484 | 266 | 490 | 498 | 363 | 880 | 238 | 253 | 479 | 181 | 7 | 181 |
| H | 266 | 498 | 484 | 880 | 490 | 253 | 363 | 181 | 238 | 479 | 8 | 479 |
| I | 498 | 880 | 266 | 253 | 484 | 181 | 490 | 479 | 363 | 238 | 9 | 238 |
| J | 880 | 253 | 498 | 181 | 266 | 479 | 484 | 238 | 490 | 363 | 10 | 363 |
| K | 880 | 498 | 253 | 266 | 181 | 484 | 479 | 490 | 238 | 363 | | |
| L | 253 | 880 | 181 | 498 | 479 | 266 | 238 | 484 | 363 | 490 | | | medians, deviations, and other statistically relevant patterns related to how one or more panelists have assessed wine characteristics.

The wine panelist data processing system 1102 is capable to remove assessments and/or intensity values associated with panelists that are deemed inaccurate or imprecise. The wine panelist data processing system 1102 is capable to adjust assessments and/or intensity values deemed biased. An assessment of a wine characteristic by a panelist's may be deemed inaccurate if it significantly deviates from how a panel or multiple panels assess the wine characteristic (e.g., relative to a global intensity value). In one example, the wine In some embodiments, the wine panelist data processing system 1102 statistically processes information related to wine characteristics. The wine panelist data processing system 1102 may identify common patterns in the information produced by panelists. For example, the wine panelist data processing system 1102 may identify averages, means, panelist data processing system 1102 may use statistical measures to deem an assessment by a panelist inaccurate, e.g., if the panelist's intensity value of fruitiness of Robert Foley Claret 2010 is two standard deviations from a global intensity value (e.g., the mean intensity value of fruitiness of Robert Foley Claret 2010 of the panel). In one example, the wine panelist data processing system 1102 may use statistical measures to deem an assessment of a wine characteristic as imprecise, e.g., if a panelist's first assessment of a wine characteristic of a wine significantly deviates from how the panelist previously assessed the same wine characteristic for the same or similar wine. An example of an imprecise assessment may include a panelist's first intensity value of fruitiness of Robert Foley Claret 2010 being five points (e.g., of a scale of six) and the panelist's prior intensity value of fruitiness of the same wine (e.g., the Robert Foley Claret 2010) as being two points.

The wine panelist data processing system 1102 may deem an a panelist's assessment of a particular wine characteristic as biased if the panelist's evaluation of this characteristic across a significant percentage (e.g., more than 50%) of wines deviates in a statistically significant way (e.g., one standard deviation, 1.5 standard deviations, fails a statistical hypothesis test such as ANOVA, etc.) from how the panel at large assesses the wine characteristic across the wines. An example of a biased assessment may include a panelist's repeated intensity value of fruitiness of all tasted wines being one or two points higher than the mean intensity value of fruitiness of those wines by a panel. In various embodiments, the wine panelist data processing system 1102 may normalize data to accommodate a panelist's bias. In the previous example, the wine panelist data processing system 1102 may lower the biased panelist's intensity values for fruitiness (e.g., by one or two points) for wines when bias was detected or, alternately, for all wines, a subset of wines (e.g., red wines). Such normalization may be performed to compute averages, means, medians, deviations, and other statistically relevant attributes of assessments.

The wine panelist data processing system 1102 may use the statistically processed information from the panels to provide specific intensities for specific descriptors for wines in the wine database 214. More specifically, the wine panelist data processing system 1102 may provide intensities and/or descriptors as database entries for storage in the wine database 214. As discussed herein, the wine database 214 may be used to match the intensities and/or descriptors with information users are seeking when they are looking for wines to experience. It will be appreciate that the wine database 214 may be stored on any digital device, such as the first digital device 102, the second digital device, 104, the wine ranking system 108, or the wine panelist data processing system 1102. Further, the wine database 214 may be stored on any other device coupled to the communication network 106.

Although only two digital devices are depicted in FIG. 11, those skilled in the art will appreciate that there may be any number of users with user databases and/or associated digital devices. Further, there may be any number of networks 106, wine ranking systems 108, and/or wine ranking processing systems 1102.

Figure 12:
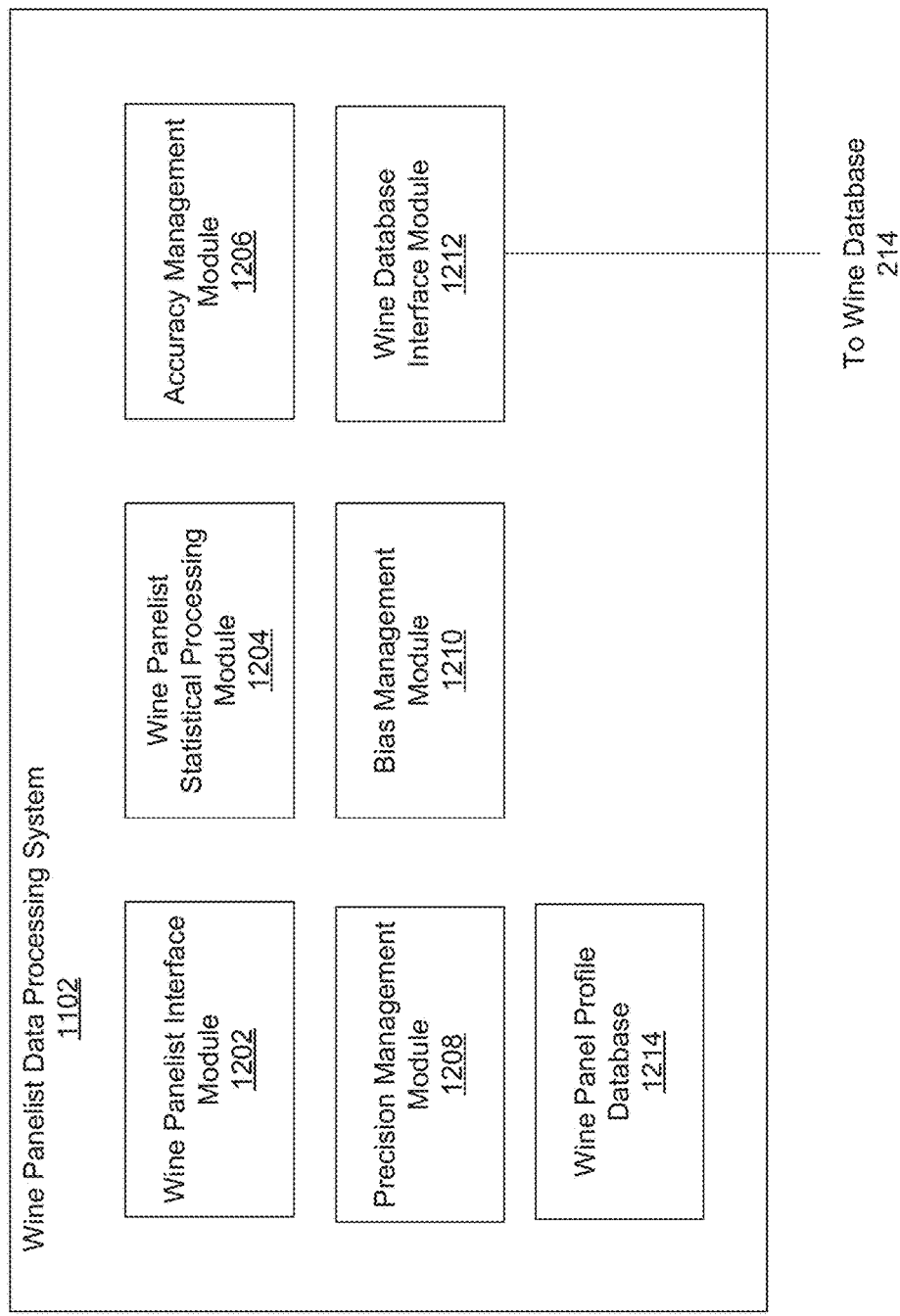
FIG. 12 depicts a block diagram of a wine panelist data processing system, according to some embodiments.

FIG. 12 depicts a block diagram of a wine panelist data processing system 1102, according to some embodiments. The wine panelist data processing system 1102 includes a wine panelist interface module 1202, a wine panelist statistical processing module 1204, an accuracy management module 1206, a precision management module 1208, a bias management module 1210, a wine database interface module 1212, and a wine panel profile database 1214. One or more of the wine panelist interface module 1202, the wine panelist statistical processing module 1204, the accuracy management module 1206, the precision management module 1208, the bias management module 1210, the wine database interface module 1212, and the wine panel profile database 1214 may be coupled to each other or to components external to the components depicted in FIG. 12. One or more of the wine panelist interface module 1202, the wine panelist statistical processing module 1204, the accuracy management module 1206, the precision management module 1208, the bias management module 1210, the wine database interface module 1212, and the wine panel profile database 1214 may include hardware, software, and/or firmware.

The wine panelist interface module 1202 may receive evaluations of wines from wine panels. The wine panelist interface module 1202 may include at least portions of an application that receives evaluations containing wine identifiers, wine descriptors, and intensity values related to wine descriptors for specific wine identifiers. For example, the wine panelist interface module 1202 may include an application to receive names of wines a panel will taste, and intensity values for wine descriptors of the wines the panelists taste.

Figure 39:
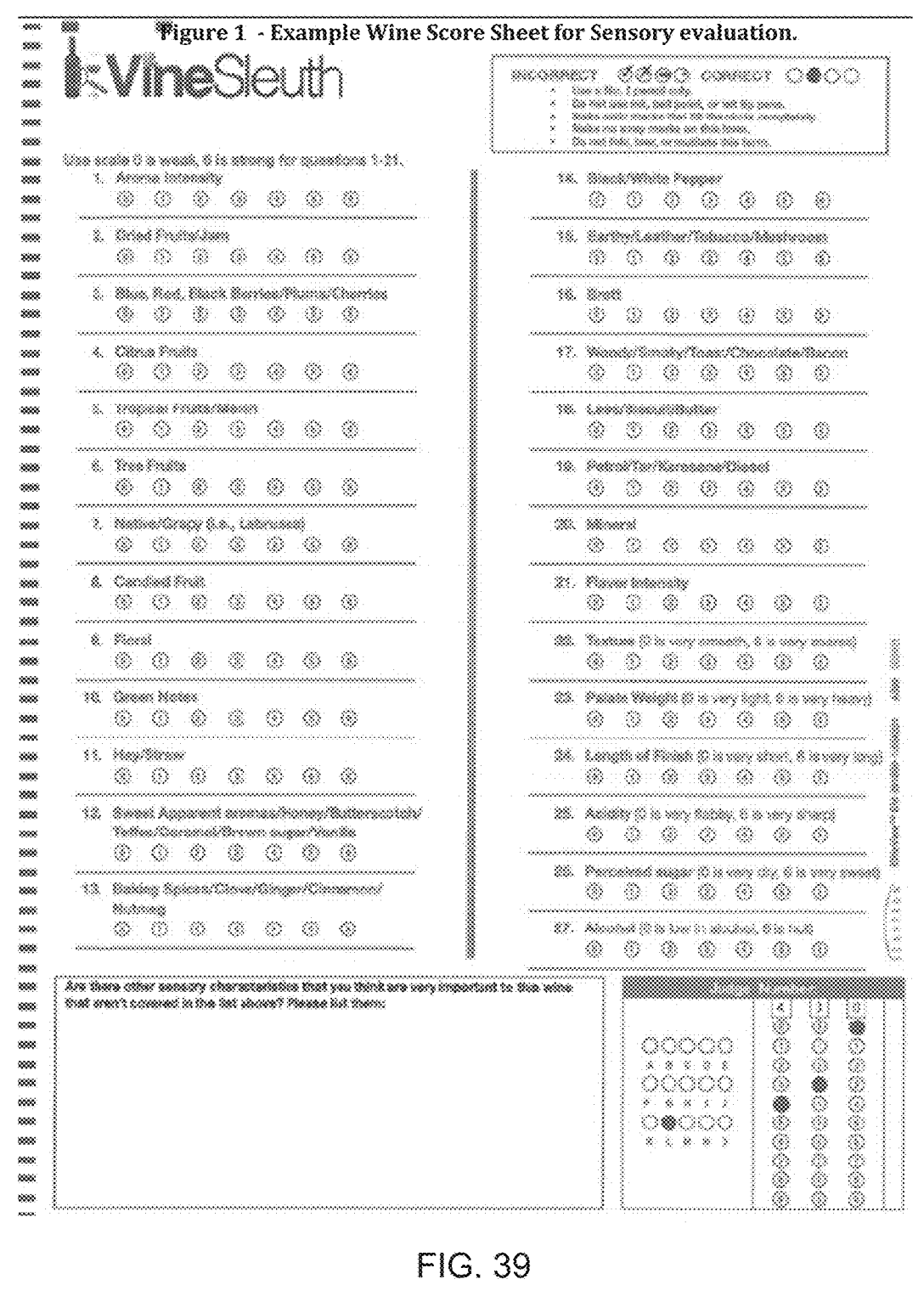

The wine panelist interface module 1202 may receive evaluations (e.g., sets of intensity values) with information related to panels and/or specific panelists. The information may include identities, backgrounds, experience levels, past tests, and other information related to specific panelists. The wine panelist interface module 1202 may store information related to tests, panelists, and/or panels in the wine panel profile database 1214. In some embodiments, the wine panelist interface module 1202 interfaces with a scanner that receives portions of Scantron® sheets or other sheets related to a panel's tasting. An example of a sheet that may be received is shown in FIG. 39. The wine panelist interface module 1202 may receive information on punch cards or other convenient format. In some embodiments, the wine panelist interface module 1202 includes a Graphical User Interface (GUI) that allows panelists or data entry personnel to electronically enter (e.g., via textual input or through selection of elements in a menu) wine identifiers, wine descriptors, and/or intensity values. As an example, the wine panelist interface module 1202 may provide panelists with a GUI generated by a mobile application to enter the results of wine tasting. As another example, the wine panelist interface module 1202 may allow data entry personnel to manually enter the results of a panel's wine tasting using a keyboard or other input device.

The wine panelist statistical processing module 1204 may perform statistical analysis on intensity values provided by panelists. The wine panelist statistical processing module 1204 may include libraries that compute averages of intensity values. In some embodiments, the wine panelist statistical processing module 1204 may include libraries that compute medians of intensity values. The wine panelist statistical processing module 1204 may include libraries that perform statistical significance tests to determine extent specific intensity values deviate from other intensity values for the same or similar wine descriptors.

In some embodiments, the wine panelist statistical processing module 1204 performs Gaussian analysis on intensity values from panelists. For example, the wine panelist statistical processing module 1204 may identify means, standard deviations, principal components, etc. of intensity values from panelists. In some embodiments, the wine panelist statistical processing module 1204 exposes libraries to other modules, such as one or more of the accuracy management module 1206, the precision management module 1208, and the bias management module 1210.

The accuracy management module 1206 may evaluate accuracy of the intensity values from a specific panelist. For example, the accuracy management module 1206 may gather (e.g., from the wine panel profile database 1214) intensity values a specific panelist has assigned to a specific descriptor of a specific wine. The accuracy management module 1206 may further obtain a global intensity value that represents how a larger group of panelists have measured the specific descriptor of the specific wine. The global intensity value may comprise an average value of intensity values from other panelists. The accuracy management module 1206 may compare the specific panelist's intensity value to the global intensity value to determine variation (if any). For example, the accuracy management module 1206 may determine a number of standard deviations between the specific panelist's intensity value and the global intensity value. In some embodiments, when the panelist's intensity value deviates from the global intensity value (e.g., the deviation is greater than a predetermined deviation threshold), the accuracy management module 1206 may remove the specific panelist's intensity value, and/or other information related to the specific panelist (other intensity values by the same panelist, etc.) from the wine panel profile database 1214. In some embodiments, removal of an assessment occurs only if the number of standard deviations exceeds a specific threshold (e.g., 1 standard deviations, 1.5 standard deviations, 2 standard deviations, or the like). In some embodiments, removal of a panelist's assessment of a particular descriptor across all wines occurs if a statistically significant number (e.g., 10%, 25%, 50%, etc.) of inaccuracy deviations are identified across the wines.

In various embodiments, the accuracy management module 1206 instructs the wine panelist statistical processing module 1204 to update the global intensity value for the specific descriptor after all wine panelists' assessments deemed inaccurate have been removed. The accuracy management module 1206 may store the updated global intensity value in the wine panel profile database 1214.

The precision management module 1208 may evaluate the precision of intensity values from a specific panelist. In some embodiments, the precision management module 1208 gathers from the wine panel profile database 1214 a plurality of intensity values that a specific panelist has assigned to a specific descriptor of a specific wine in a plurality of tastings. The precision management module 1208 compares the plurality of values to one another. The precision management module 1208 may remove one or more of the plurality of intensity values from the wine panel profile database 1214 if the intensity values sufficiently deviate from one another (e.g., two or more intensity values deviate from each other beyond a deviation threshold). In some embodiments, removal of the panelist's intensity value occurs only if the standard deviations exceeds a specific threshold (e.g., 1 standard deviations, 1.5 standard deviations, 2 standard deviations, or the like). In some embodiments, removal of a panelist's assessment of a particular descriptor across all wines occurs if a statistically significant number (e.g., 10%, 25%, 50%, etc.) of imprecision deviations are identified across the wines.

In various embodiments, the precision management module 1208 instructs the wine panelist statistical processing module 1204 to update the global intensity value for the specific descriptor after all wine panelists' assessments deemed imprecise have been removed. The precision management module 1208 may store the updated global intensity value in the wine panel profile database 1214.

The bias management module 1210 may identify bias in the intensity values of a specific panelist. In some embodiments, the bias management module 1210 gathers from the wine panel profile database 1214 all of a specific panelist's intensity values related to a specific wine descriptor or to similar wine descriptors across a plurality of wines. The bias management module 1210 may compare the specific panelist's intensity values with global intensity values for the same or similar wine descriptors across the plurality of wines. In an embodiment, the bias management module 1210 determines whether a substantial number of intensity values deviate from global intensity values and form a common deviation pattern. For example, the bias management module 1210 may determine whether a majority of a specific panelist's intensity values are consistently one point higher than the global intensity value for the same or similar wine descriptors across the wines.

The bias management module 1210 may take corrective actions if biased panelists are identified. In an embodiment, the bias management module 1210 corrects the intensity values of a biased individual based on the common deviation pattern. To continue the foregoing example of the specific panelist whose intensity values were consistently one point higher than the global intensity value, the bias management module 1210 may reduce the specific panelist's intensity values by one for those relevant descriptors (e.g., for those descriptors related to intensity values that deviated from global intensity values in a common deviation pattern).

The wine database interface module 1212 may couple the modules of the wine panelist data processing system 1102 to the communications network 1106. In an embodiment, the wine database interface module 1212 provides information related to wine tests, wine panelists, and/or wine panels to the wine database 214 (shown in FIG. 2). The wine database interface module 1212 may instruct the wine database 214 to store the relevant information in the form of data records that can be accessed by the other modules of the first digital device 102, the second digital device 104, and/or the wine ranking system 108.

The wine panel profile database 1214 may include hardware, software, and/or firmware that stores information related to wine tests, wine panelists, and/or wine panels. In various embodiments, the wine panel profile database 1214 receives information related to wine tests, wine panelists, and/or wine panels from the wine panelist interface module 1202. The wine panel profile database 1214 may also provide information related to wine tests, wine panelists, and/or wine panels to the other modules of the wine panelist data processing system 1102.

It will be appreciated that a module may include hardware, software, and/or firmware.

Figure 13:
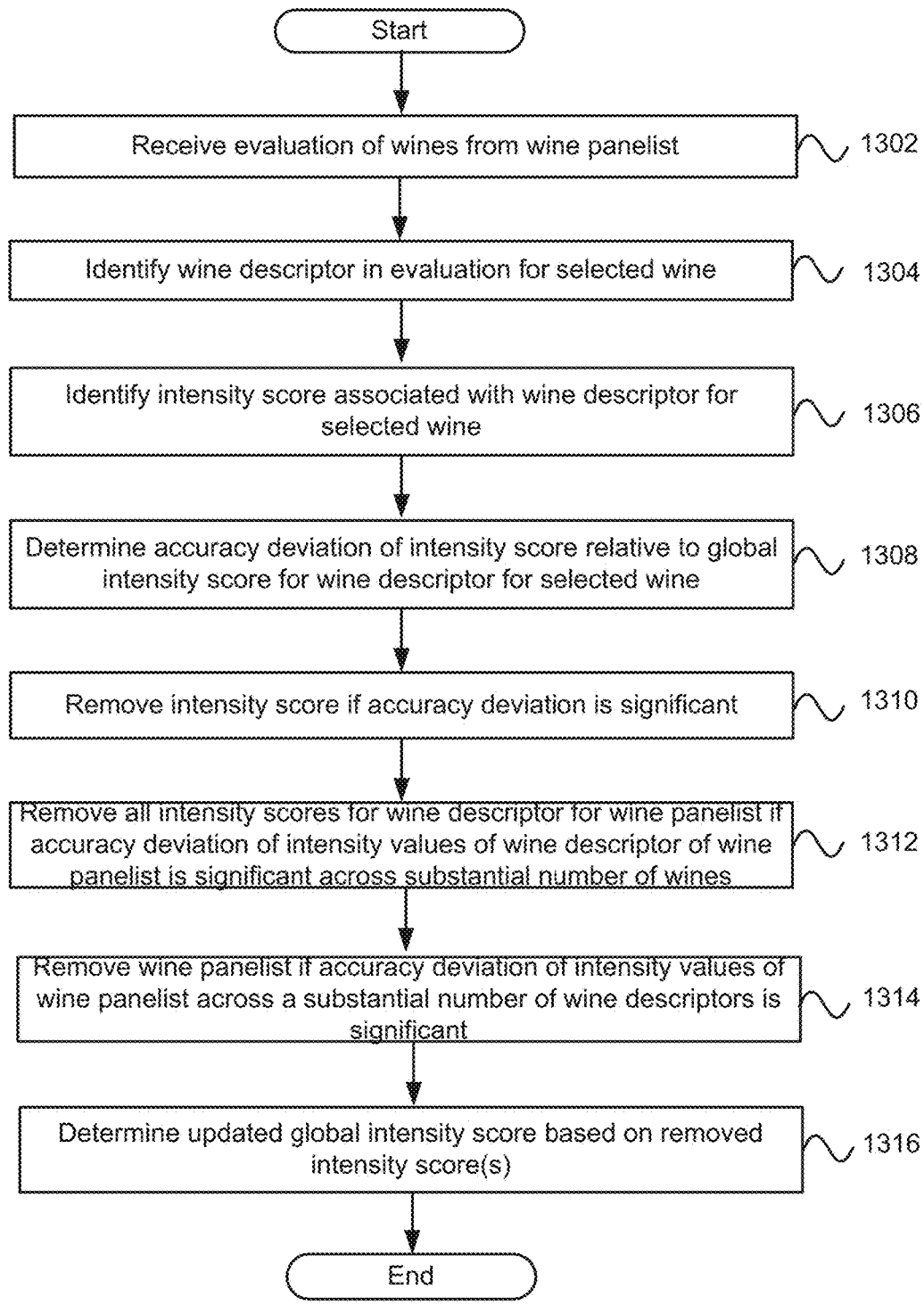
FIG. 13 depicts a flowchart of a method for processing wine rankings using the accuracy of an evaluation of wines from a wine panelist, according to some embodiments.

FIG. 13 depicts a flowchart of a method 1300 for processing wine rankings using the accuracy of an evaluation of wines from a wine panelist, according to some embodiments. The method 1300 is discussed in conjunction with the wine panelist data processing system 1102, shown in FIG. 12. It is noted at least some embodiments may include more or fewer steps than the steps shown in the method 1300.

At step 1302, the wine panelist interface module 1202 receives an evaluation of wines from a wine panelist. In an embodiment, the wine panelist interface module 1202 receives evaluations identified on a Scantron® sheet (see, e.g., the sheet in FIG. 39) or punch card. In some embodiments, the wine panelist interface module 1202 receives evaluations entered in an electronic format. The evaluations may contain information related to wine identifiers, wine descriptors, and/or intensities related to wine descriptors. In some embodiments, the wine panelist interface module 1202 stores evaluations in a known or convenient format in the wine panel profile database 1214.

At step 1304, the wine processing statistical panelist module 1204 identifies a wine descriptor in the evaluation for the selected wine. More specifically, the wine panelist statistical processing module 1204 may identify one or more of the wine descriptors in the evaluations for further statistical processing. In an embodiment, the wine panelist statistical processing module 1204 identifies a single wine descriptor. In other embodiments, the wine panelist statistical processing module 1204 identifies groups of wine descriptors that are similar to one another and that can be analyzed together. For example, the wine panelist statistical processing module 1204 may identify all wine descriptors that are associated with fruity characteristics.

At step 1306, the wine panelist statistical processing module 1204 identifies an intensity value associated with the wine descriptor for the selected wine. For example, the wine panelist statistical processing module 1204 may identity the intensity value a panelist assigned to the identified wine descriptor. The intensity value may comprise the intensity value provided on the panelist's evaluation. The wine panelist statistical processing module 1204 may adjust the intensity value so that it can be compared with a global intensity value for the wine descriptor.

At step 1308, the accuracy management module 1206 determines an accuracy deviation (if any) of the intensity value relative to a global intensity value for the wine descriptor for the selected wine. In some embodiments, the accuracy management module 1206 determines a number of standard deviations between the intensity value and the global intensity value. The accuracy management module 1206 may also determine the accuracy deviation in other ways, such as computing a simple difference between the intensity value and the global intensity value. The accuracy management module 1206 may provide the accuracy deviation to the wine panelist statistical processing module 1204.

At step 1310, the accuracy management module 1206 removes the intensity value if the accuracy deviation is significant. As discussed, in some embodiments, the accuracy management module 1206 determines the number of standard deviations between the intensity value and the global intensity value. If the number of standard deviations meets a specific threshold (e.g., 1 standard deviation, 1.5 standard deviations, 2 standard deviations, or greater) the accuracy management module 1206 may delete, hide, the intensity value from the wine panel profile database 1214 or mark the intensity value in a manner so that the intensity value is not used for future computations of the general intensity value.

At step 1312, the accuracy management module 1206 removes all intensity values for the wine descriptor for the wine panelist if the accuracy deviation of the intensity values of the wine descriptor for the wine panelist is significant across a substantial number of wines. For example, if the number of standard deviations meets another specific threshold (which may or may not correspond to the threshold for removing a single intensity value), the accuracy management module 1206 may remove all intensity values for the wine descriptor from the wine panelist. As an example, if the panelist's intensity value for hay straw is more than two standard deviations from the global intensity value for hay straw for a given wine, the accuracy management module 1206 may remove all of the panelist's intensity values for hay straw across all wines.

At step 1314, the accuracy management module 1206 removes the wine panelist if accuracy deviation of the intensity values of the wine descriptor across a substantial number of wine descriptors is significant. The number of wines required to constitute a "substantial" number of wine descriptors may vary depending on the specific implementation. However, if a panelist's accuracy deviation on a number of intensity values of the panelist are inaccurate, the accuracy management module 1314 may remove the wine panelist's input from the wine panel profile database 1214.

At step 1316, the wine panelist statistical processing module 1204 determines an updated global intensity value without the removed intensity value(s). More specifically, the wine panelist statistical processing module 1204 may recalculate the global intensity value without the contribution of the intensity value(s) removed from the wine panel profile database 1214. Such recalculation may involve calculating the mean, median, etc. value of intensity values for wine descriptors that were processed by the accuracy management module 1206.

Figure 14:
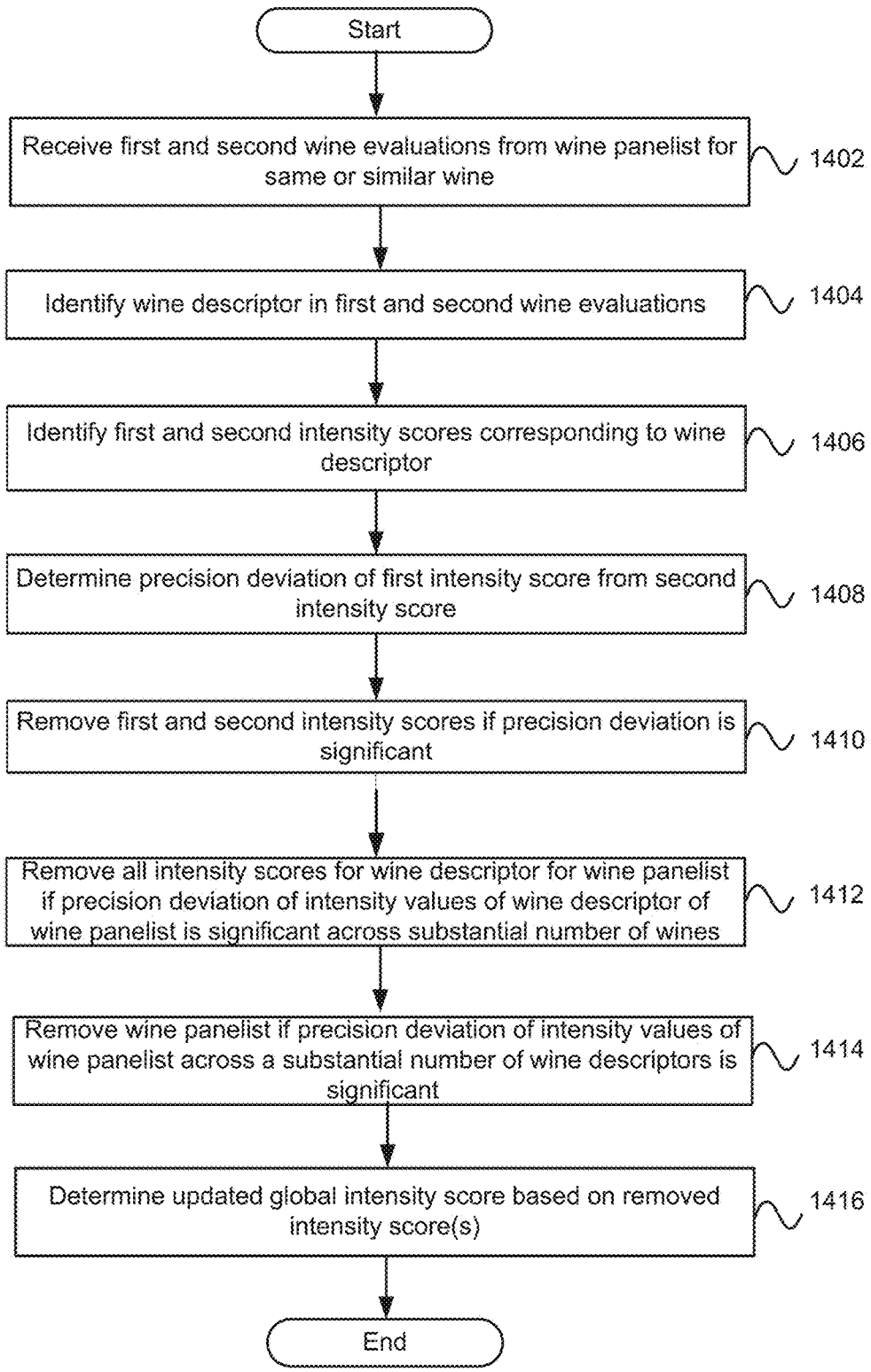
FIG. 14 depicts a flowchart of a method for processing wine rankings using precision of an evaluation of wines from a wine panelist, according to some embodiments.

FIG. 14 depicts a flowchart of a method 1400 for processing wine rankings using precision of an evaluation of wines from a wine panelist, according to some embodiments. The method 1400 is discussed in conjunction with the wine panelist data processing system 1102, shown in FIG. 12. It is noted at least some embodiments may include more or fewer steps than the steps shown in the method 1400.

At step 1402, the wine panelist interface module 1202 receives first and second wine evaluations from a wine panelist for the same or a similar wine. In an embodiment, the wine panelist interface module 1202 receives first and second evaluations from a Scantron® sheet or punch card. In some embodiments, the wine panelist interface module 1202 receives evaluations entered in an electronic format. The first and second evaluations may contain information related to wine identifiers, wine descriptors, and/or intensities related to wine descriptors. In some embodiments, the wine panelist interface module 1202 stores the first and second evaluations in a known or convenient format in the wine panel profile database 1214. The first and second wine evaluations may be related to the same wine or wines with similar characteristics.

At step 1404, the wine processing statistical panelist module 1204 identifies a wine descriptor in the first and second evaluations. More specifically, the wine panelist statistical processing module 1204 may identify a wine descriptor in the first and second evaluations for further statistical processing. As an example, the wine panelist statistical processing module 1204 may identify a wine descriptor corresponding to floral characteristics.

At step 1406, the wine panelist statistical processing module 1204 identifies first and second intensity values from the same panelist, the first and second intensity values corresponding to the wine descriptor. For example, the wine panelist statistical processing module 1204 may identify a first intensity value for the wine descriptor in the first evaluation, and a second intensity value for the wine descriptor in the second evaluation. The first and second intensity values may correspond to different times the same wine panelist has evaluated the same characteristic of the same or similar wine.

At step 1408, the precision management module 1208 determines a precision deviation (if any) of the first intensity value from the second intensity value. More specifically, the precision management module 1208 may determine the extent the first and second intensity values differ from one another. In some embodiments, the precision management module 1208 determines the extent the first and second intensity values deviate from a global intensity value for the wine descriptor.

At step 1410, the precision management module 1208 removes the first and second intensity values from the wine panel profile database 1214 and/or the global intensity value if the precision deviation is significant. In some implementations, the precision management module 1208 may delete, hide, the intensity value from the wine panel profile database 1214 or mark the first and/or second intensity values in a manner so that the first and/or second intensity values are not used for future computations of the general intensity value. At step 1412, the precision management module 1208 removes all intensity values for the wine descriptor for the wine panelist if the precision deviation of the intensity values of the wine descriptor of the wine panelist is significant (e.g., exceeds a predetermined precision deviation threshold) across a substantial number of wines. At step 1414, the precision management module 1208 removes the wine panelist if the precision deviation of the intensity values of the wine panelist is across a substantial number of wine descriptors is significant.

At step 1416, the wine panelist statistical processing module 1204 determines an updated global intensity value without the removed intensity value(s). More specifically, the wine panelist statistical processing module 1204 may recalculate the global intensity value without the contribution of the intensity value(s) removed from the wine panel profile database 1214. Such recalculation may involve calculating the mean, median, etc. value of intensity values for wine descriptors that were processed by the accuracy management module 1206.

Figure 15:
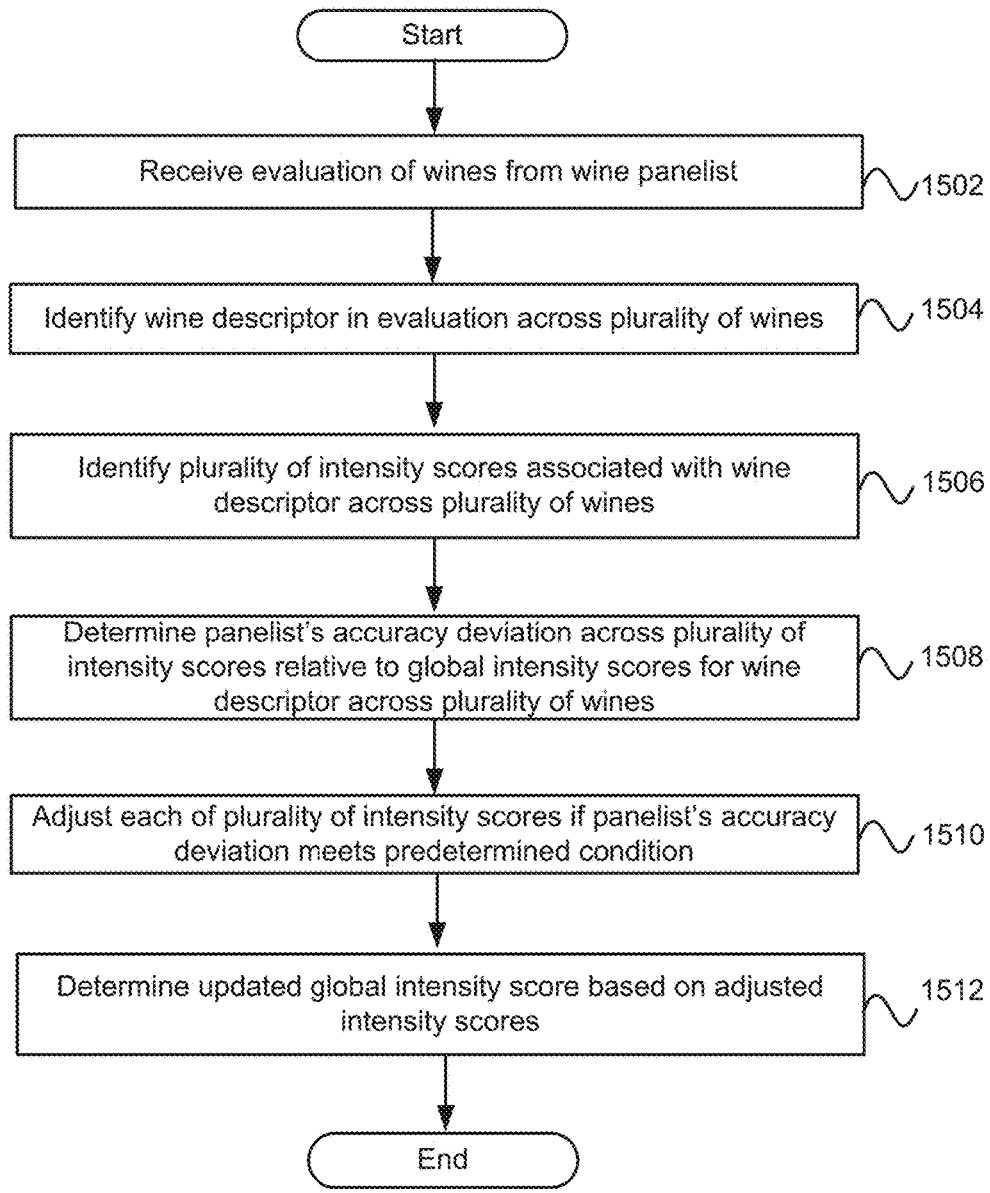
FIG. 15 depicts a flowchart of a method for processing wine rankings using an identified bias on the part of a wine panelist, according to some embodiments.

FIG. 15 depicts a flowchart of a method 1500 for processing wine rankings using an identified bias on the part of a wine panelist, according to some embodiments. The method 1500 is discussed in conjunction with the wine panelist data processing system 1102, shown in FIG. 12. It is noted at least some embodiments may include more or fewer steps than the steps shown in the method 1500.

At step 1502, the wine panelist interface module 1202 receives an evaluation of wines from a wine panelist. As discussed herein, the evaluation may contain information related to wine identifiers, wine descriptors, and/or intensities related to wine descriptors. In some embodiments, the wine panelist interface module 1202 stores the evaluation in a known or convenient format in the wine panel profile database 1214.

At step 1504, the wine processing statistical panelist module 1204 identifies a wine descriptor in the evaluation across a plurality of wines. More specifically, the wine panelist statistical processing module 1204 may identify a wine descriptor in the evaluation for further statistical processing. For example, the wine panelist statistical processing module 1204 may identify the wine descriptor associated with petrol characteristics.

At step 1506, the bias management module 1210 identifies a plurality of intensity values associated with the wine descriptor across the plurality of wines. The bias management module 1210 may determine all or a significant number (e.g., beyond a threshold) of the intensity values the wine panelist has provided related to the wine descriptor. To continue the foregoing example, the bias management module 1210 may identify all intensity values related to petrol the wine panelist has provided for all wines.

At step 1508, the bias management module 1210 determines the wine panelist's accuracy deviation across the plurality of intensity values relative to a global intensity value for the wine descriptor across the plurality of wines. In an embodiment, the bias management module 1210 determines the extent the wine panelist's intensity values for the wine descriptor have deviated (if any) from the global intensity value for that wine descriptor across all wines the wine panelist has tasted. To continue the foregoing example, the bias management module 1210 may determine the extent a wine panelist's intensity values for petrol deviate from the global intensity value. An example of such a biased panelist may include one who consistently provides an intensity value for petrol an average of two points higher than the global intensity value for petrol across all wines.

At step 1510, the bias management module 1210 adjusts each of the plurality of intensity values if the panelist's accuracy deviation meets a predetermined condition. That is, the bias management module 1210 may raise or lower the panelist's intensity values for the wine descriptor by the number of points the intensity values deviated from the global intensity value for the wine descriptor across all wines. To continue the foregoing example, the bias management module 1210 may lower the petrol-biased panelist's intensity values for petrol by two points across all wines.

At step 1512, the wine panelist statistical processing module 1204 determines an updated global intensity value based on the adjusted intensity values. More specifically, the wine panelist statistical processing module 1204 may recalculate the global intensity using the adjusted intensity value. Such recalculation may involve calculating the mean, median, etc. value of intensity values for wine descriptors that were processed by the accuracy management module 1206.

FIG. 16 depicts a table that illustrates the difference between intensity values of two wine panels, according to some embodiments. The first column of the table includes wine descriptors. The second column of the table shows intensity values of a first wine panel. The third column of the table shows the intensity values of a second wine panel. The fourth column of the table shows a measure of the statistical significance (e.g., the p-value) for each wine descriptor. In the example of FIG. 16, panels were constituted for a variety of red wines. FIG. 17 depicts a table that illustrates the difference between intensity values of two wine panels, according to some embodiments. The table is similar to the table in FIG. 16, but the panels identified in FIG. 17 were constituted for a variety of white wines. FIG. 18 depicts a table that illustrates the difference between intensity values of two wine panels (e.g., different than those panels of FIG. 16), according to some embodiments. FIG. 19 depicts a table that illustrates the difference between intensity values of two wine panels (e.g., different than those panels of FIG. 16), according to some embodiments.

FIG. 20 depicts a table that illustrates the difference between the scores by the number of wines per flight, according to some embodiments. The wines for the table are varieties of red wines. FIG. 21 depicts a table that illustrates the difference between the scores by the number of wines per flight, according to some embodiments. The wines for the table include different varieties of white wines.

Figure 22:
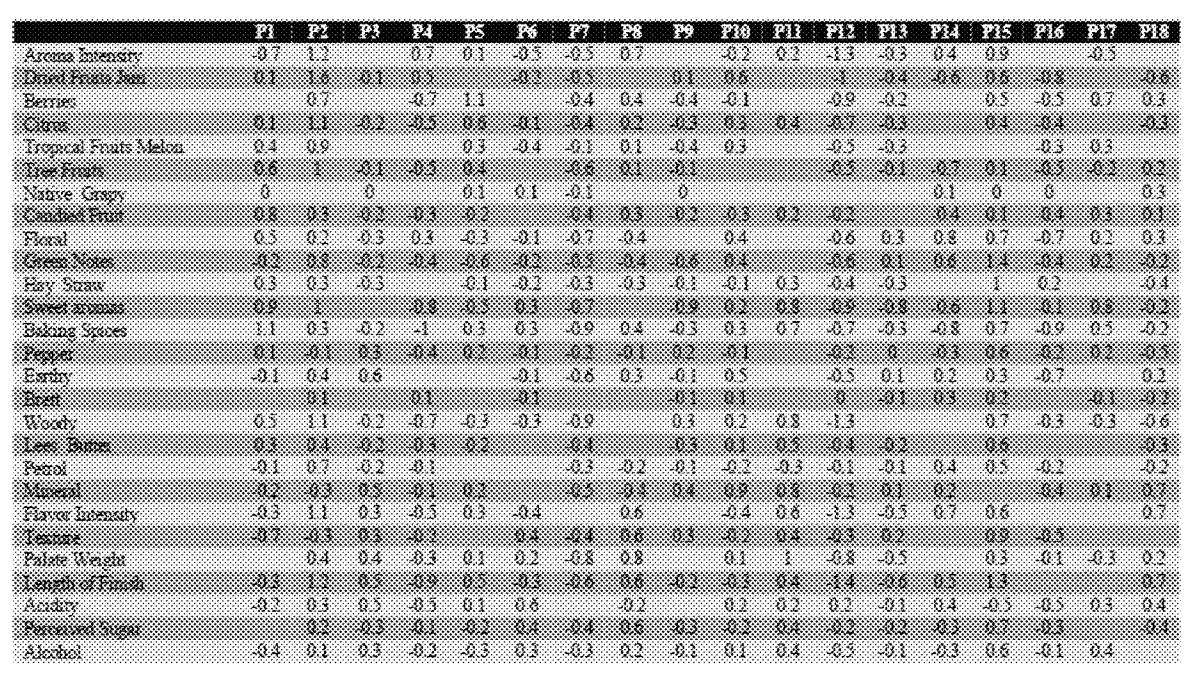

FIG. 22 depicts a table that illustrates average panelist bias for a set of panels, according to some embodiments. FIG. 23 depicts a table that illustrates the results of wine ranking processing for several varieties of wine, according to some embodiments.

Figure 28:
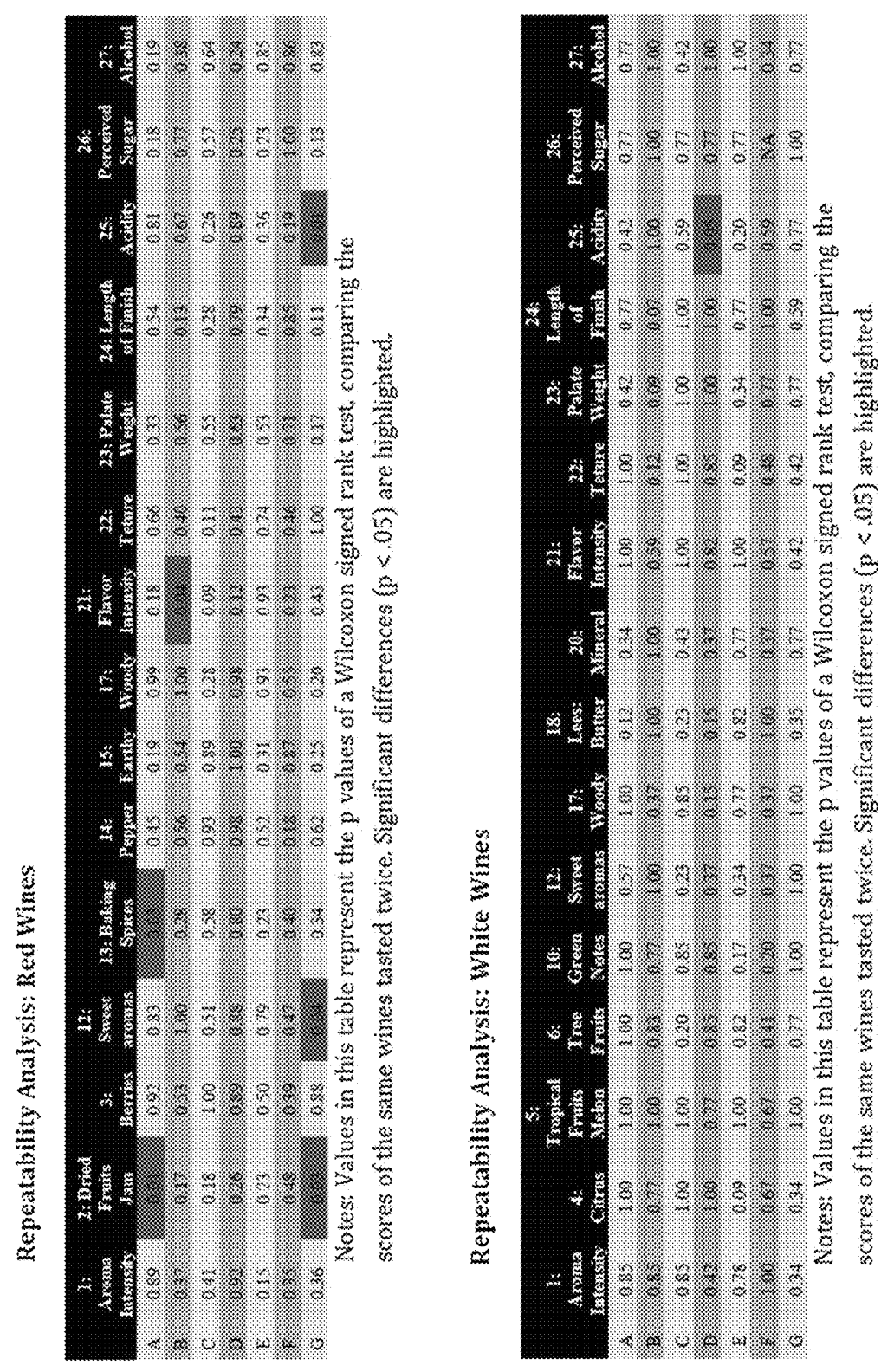

FIG. 24 depicts a table that illustrates principal component analysis of a dataset of descriptors, according to some embodiments. It will be appreciated that any statistical model or analytical approach may be used. FIG. 25 depicts a table that illustrates principal component analysis of a dataset that excludes non-repeatable descriptors, according to some embodiments. FIG. 26 depicts a table that illustrates principal component analysis of a dataset that excludes non-repeatable descriptors and outliers, according to some embodiments. FIG. 27 depicts a table that illustrates principal component analysis of a dataset that excludes outliers, according to some embodiments. FIG. 28 depicts a table that illustrates repeatability analysis of a dataset of wines, according to some embodiments.

Figure 29A:
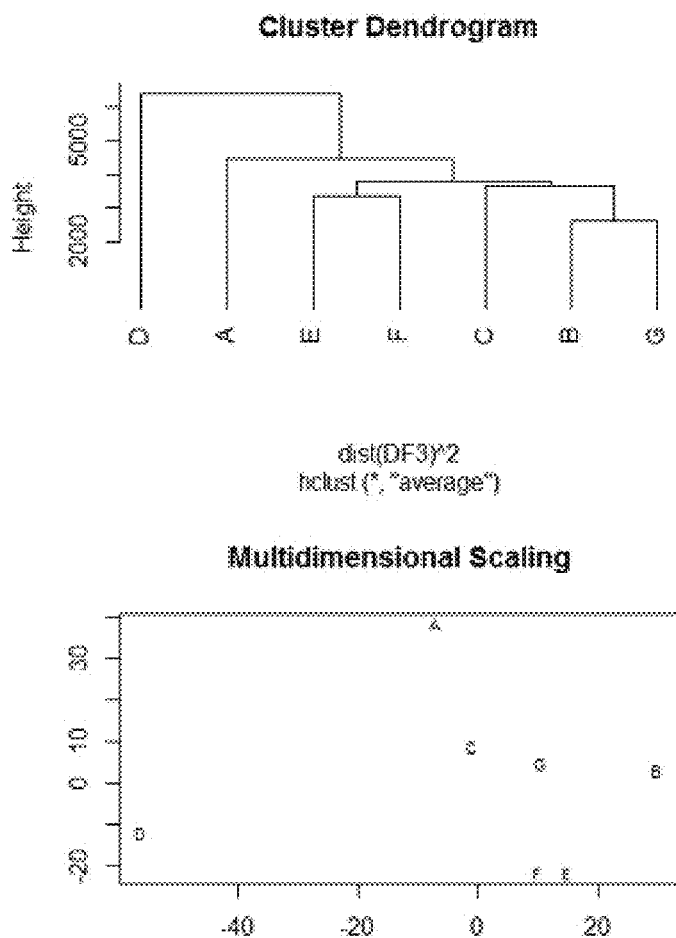
FIG. 29A depicts a diagrams that illustrates a cluster dendogram and multidimensional scaling of panelist groupings, according to some embodiments.
Figure 29B:
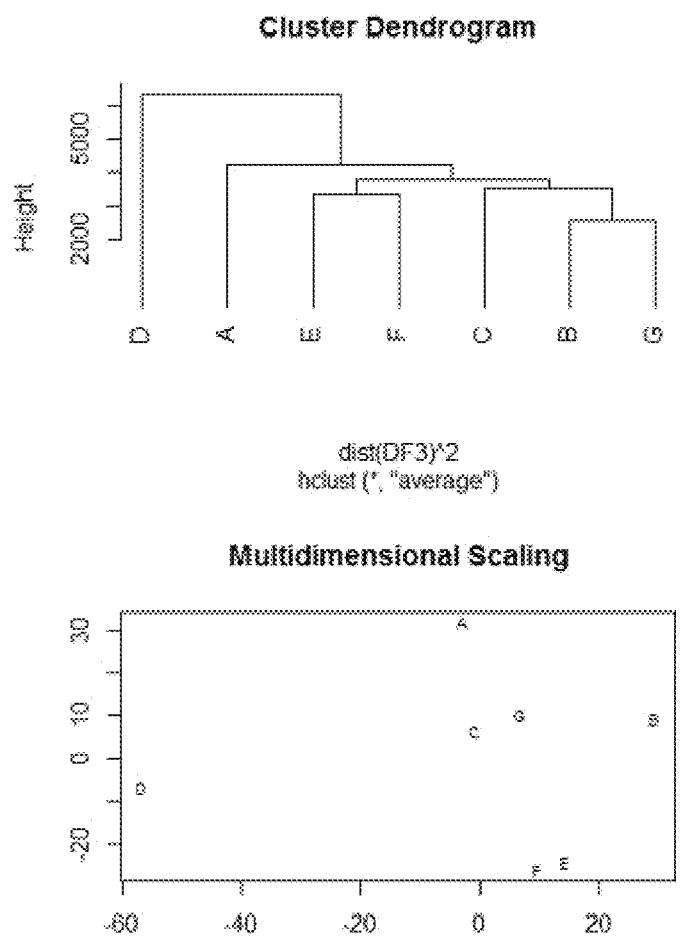
FIG. 29B depicts a diagrams that illustrates a cluster dendogram and multidimensional scaling of panelist groupings, according to some embodiments.
Figure 29C:
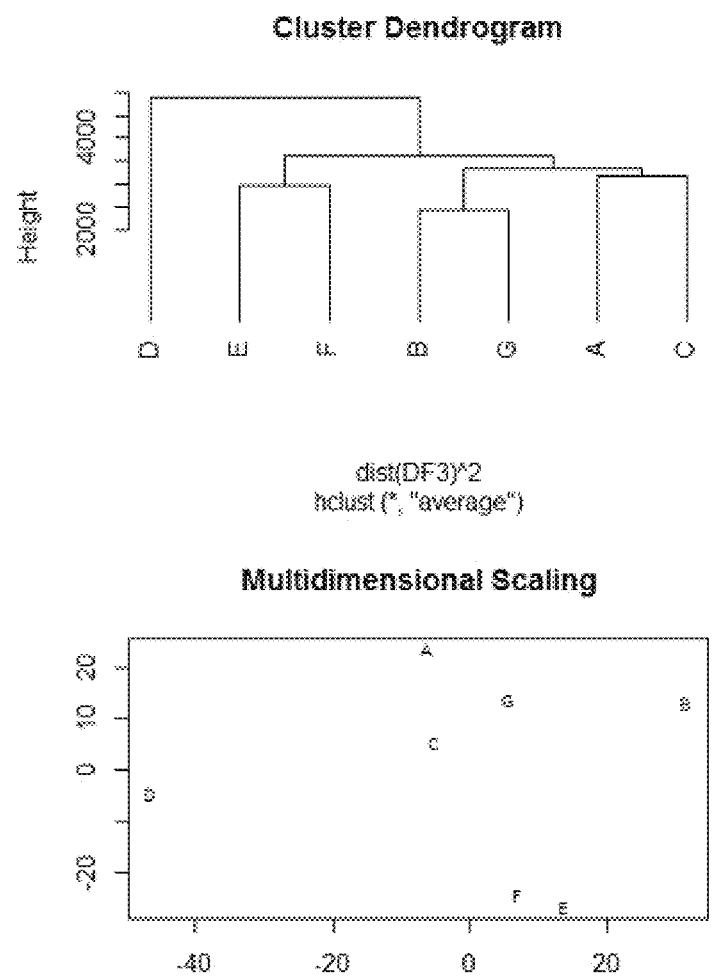
FIG. 29C depicts a diagrams that illustrates a cluster dendogram and multidimensional scaling of panelist groupings, according to some embodiments.
Figure 29D:
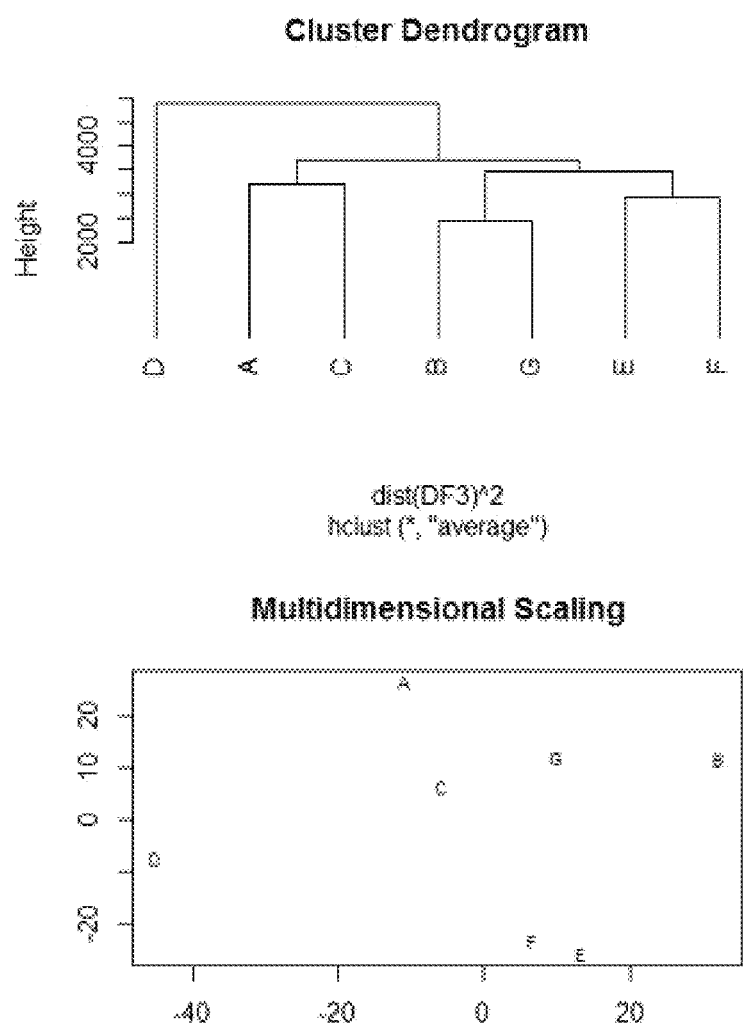
FIG. 29D depicts a diagrams that illustrates a cluster dendogram and multidimensional scaling of panelist groupings, according to some embodiments.

FIG. 29A depicts a diagram that illustrates a cluster dendogram and a multidimensional scaling of panelist groupings, according to some embodiments. In the example of FIG. 29A, the dataset for the cluster dendogram and multidimensional scaling is the full dataset. FIG. 29B depicts a diagram that illustrates a cluster dendogram and a multidimensional scaling of panelist groupings, according to some embodiments. In the example of FIG. 29b, the dataset for the cluster dendogram and multidimensional scaling includes non-repeatable wine descriptors. FIG. 29C depicts a diagram that illustrates a cluster dendogram and a multidimensional scaling of panelist groupings, according to some embodiments. In the example of FIG. 29B, the dataset for the cluster dendogram and multidimensional scaling excludes non-repeatable wine descriptors. FIG. 29D depicts a diagram that illustrates a cluster dendogram and a multidimensional scaling of panelist groupings, according to some embodiments. In the example of FIG. 29D, the dataset for the cluster dendogram and multidimensional scaling excludes outliers. These cluster dendograms and multidimensional scalings become progressively more accurate, precise, and less biased as statistical analysis on the dataset is performed. For example, the cluster dendogram and multidimensional scaling is more accurate, more precise, and less biased than the cluster dendogram and multidimensional scaling of FIG. 29A.

Figure 30A:
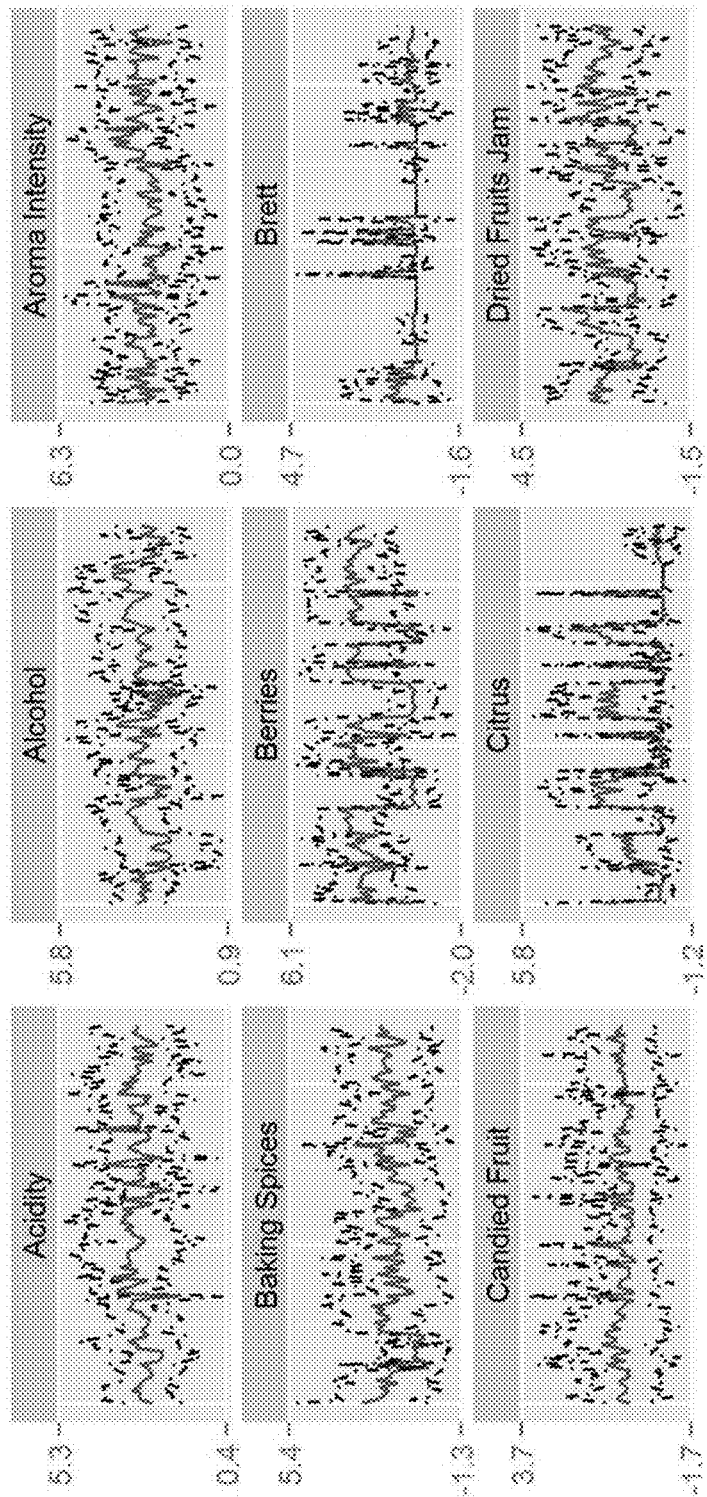
FIG. 30A depicts the results of wine ranking processing for a set of descriptor of wine, according to some embodiments.
Figure 30B:
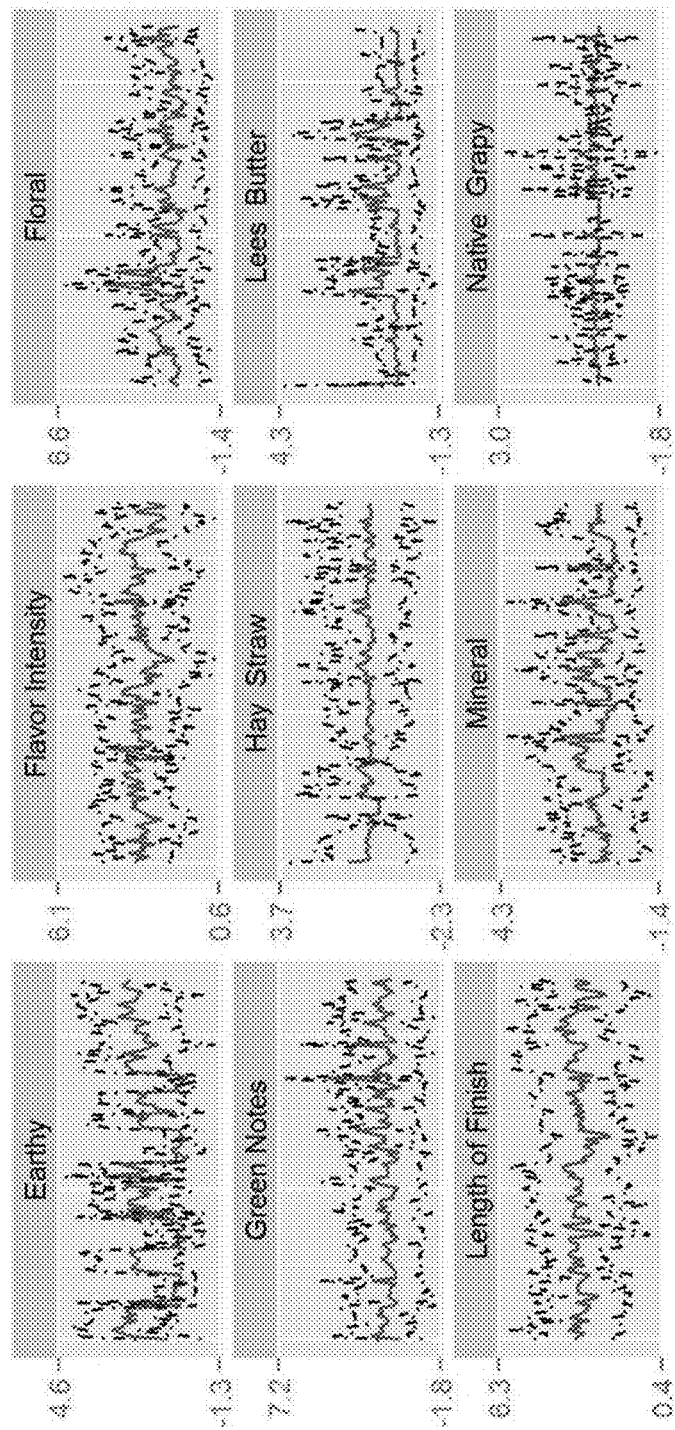
FIG. 30B depicts the results of wine ranking processing for a set of descriptor of wine, according to some embodiments.
Figure 30C:
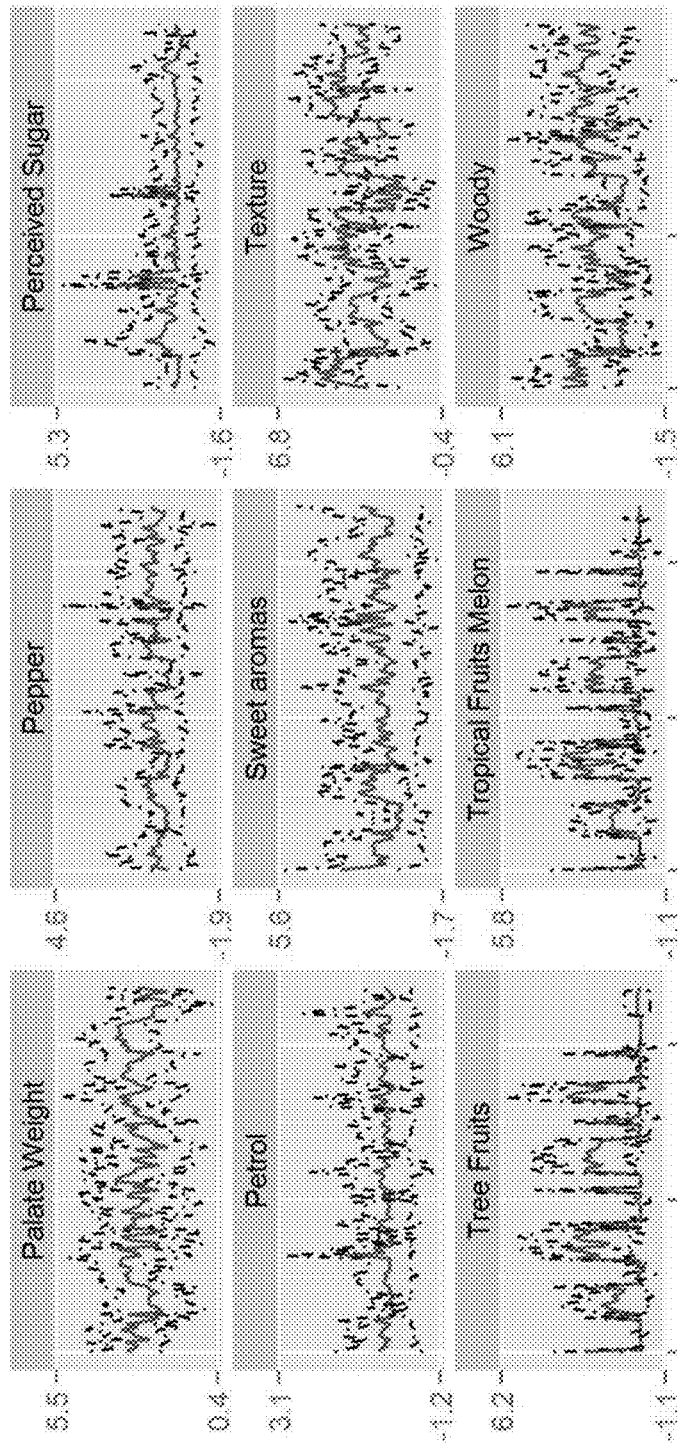
FIG. 30C depicts the results of wine ranking processing for a set of descriptor of wine, according to some embodiments.

FIG. 30A depicts the results of wine ranking processing for a set of descriptor of wine, according to some embodiments. FIG. 30B depicts the results of wine ranking processing for a set of descriptor of wine, according to some embodiments. FIG. 30C depicts the results of wine ranking processing for a set of descriptor of wine, according to some embodiments. The results shown in FIGS. 30A-30C include a full dataset from a tasting by a panel.

Figure 31A:
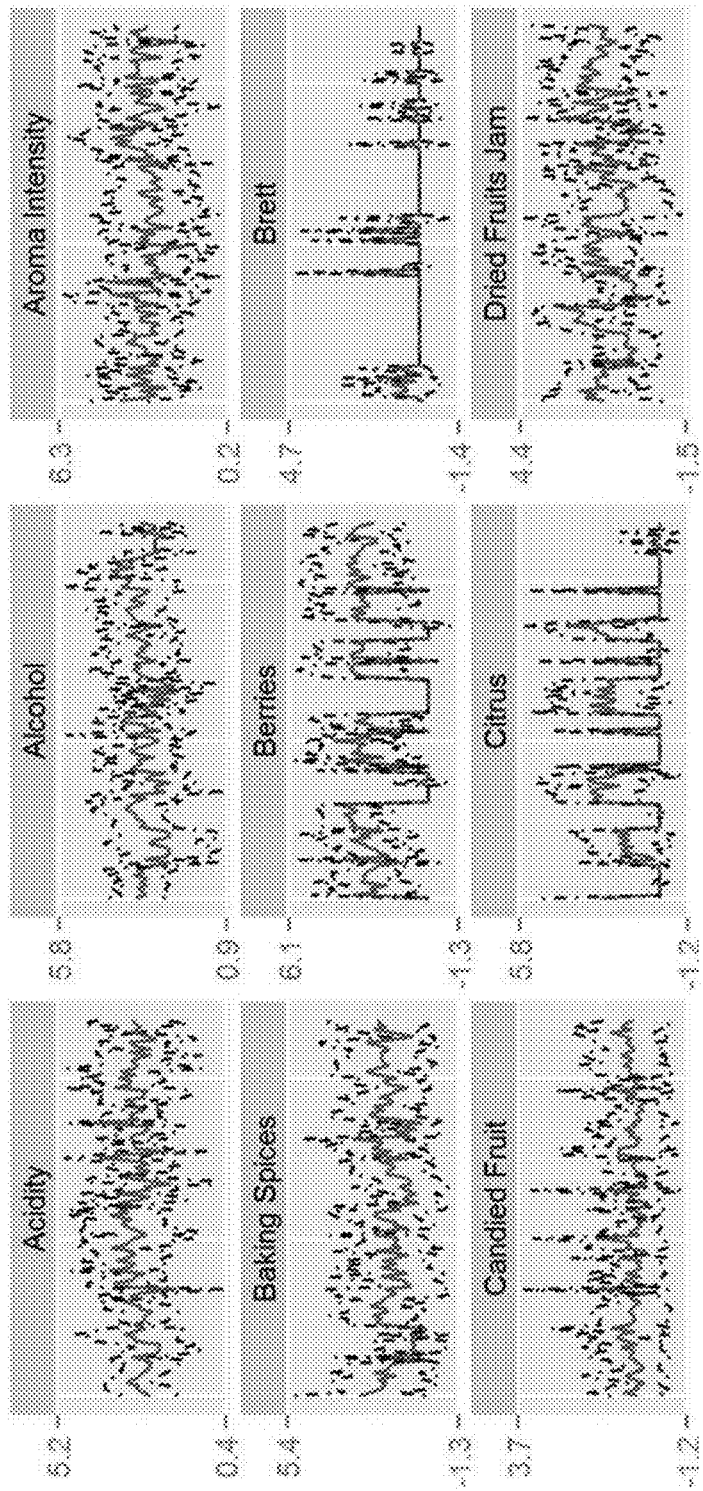
FIG. 31A depicts the results of wine ranking processing for a set of descriptor of wine, according to some embodiments.
Figure 31B:
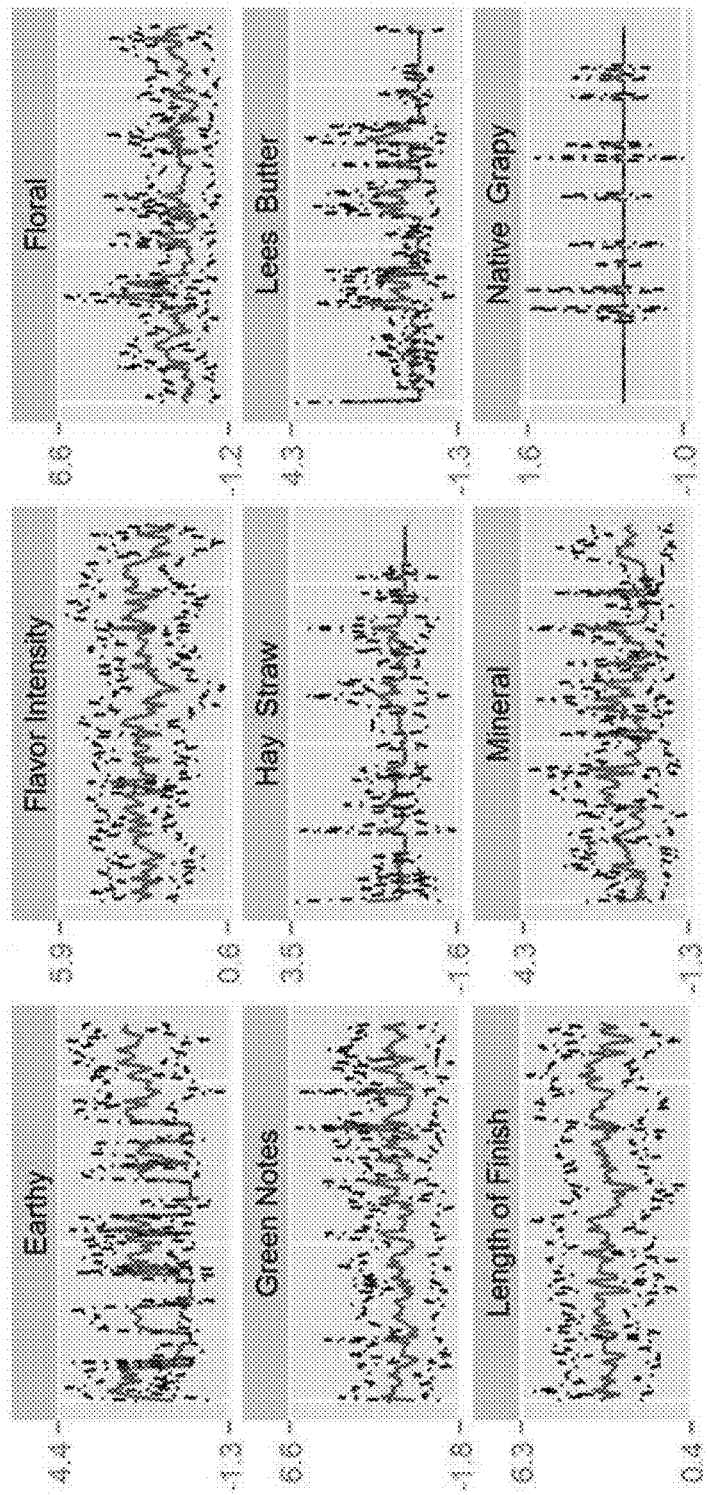
FIG. 31B depicts the results of wine ranking processing for a set of descriptor of wine, according to some embodiments.
Figure 31C:
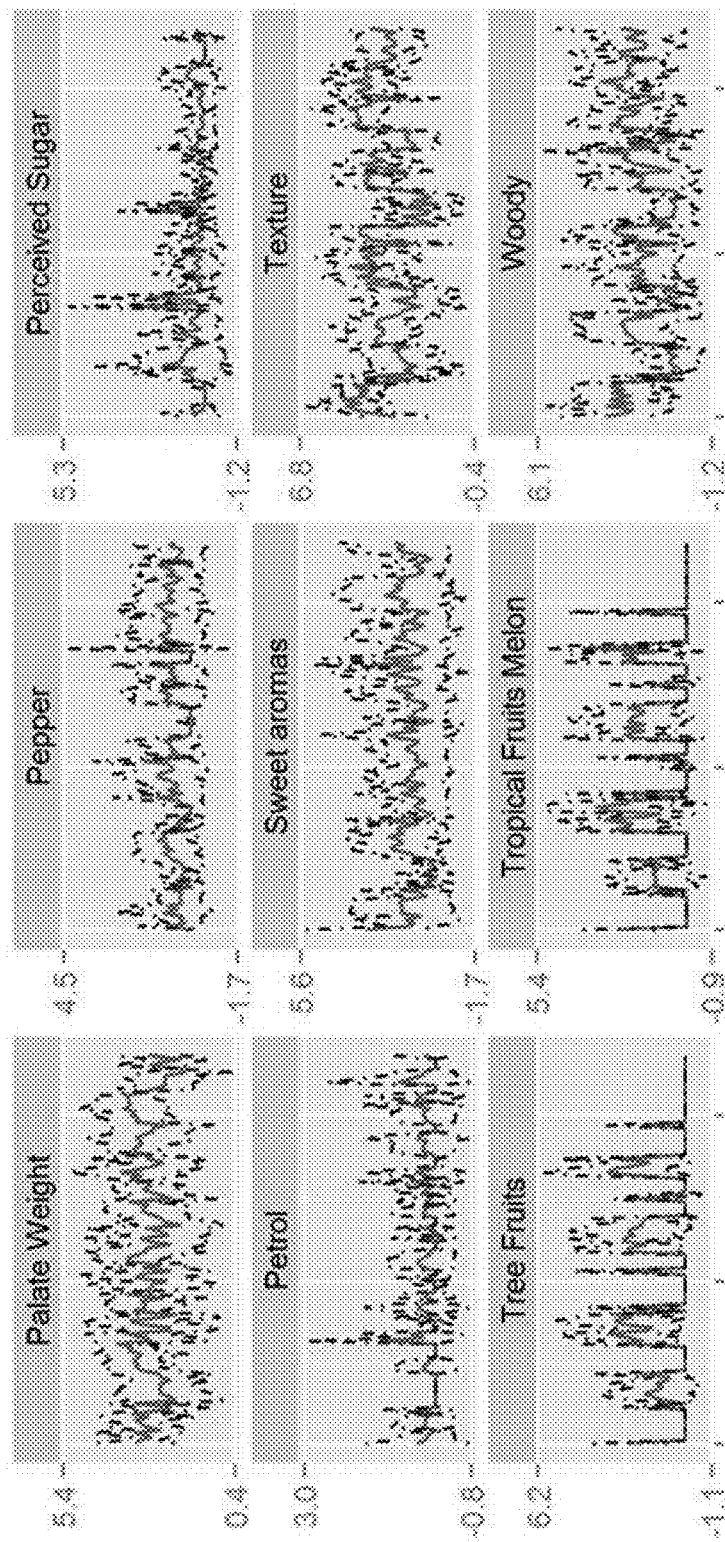
FIG. 31C depicts the results of wine ranking processing for a set of descriptor of wine, according to some embodiments.

FIG. 31A depicts the results of wine ranking processing for a set of descriptor of wine, according to some embodiments. FIG. 31B depicts the results of wine ranking processing for a set of descriptor of wine, according to some embodiments. FIG. 31C depicts the results of wine ranking processing for a set of descriptor of wine, according to some embodiments. The results shown in FIGS. 31A-31C exclude outliers.

Figure 32A:
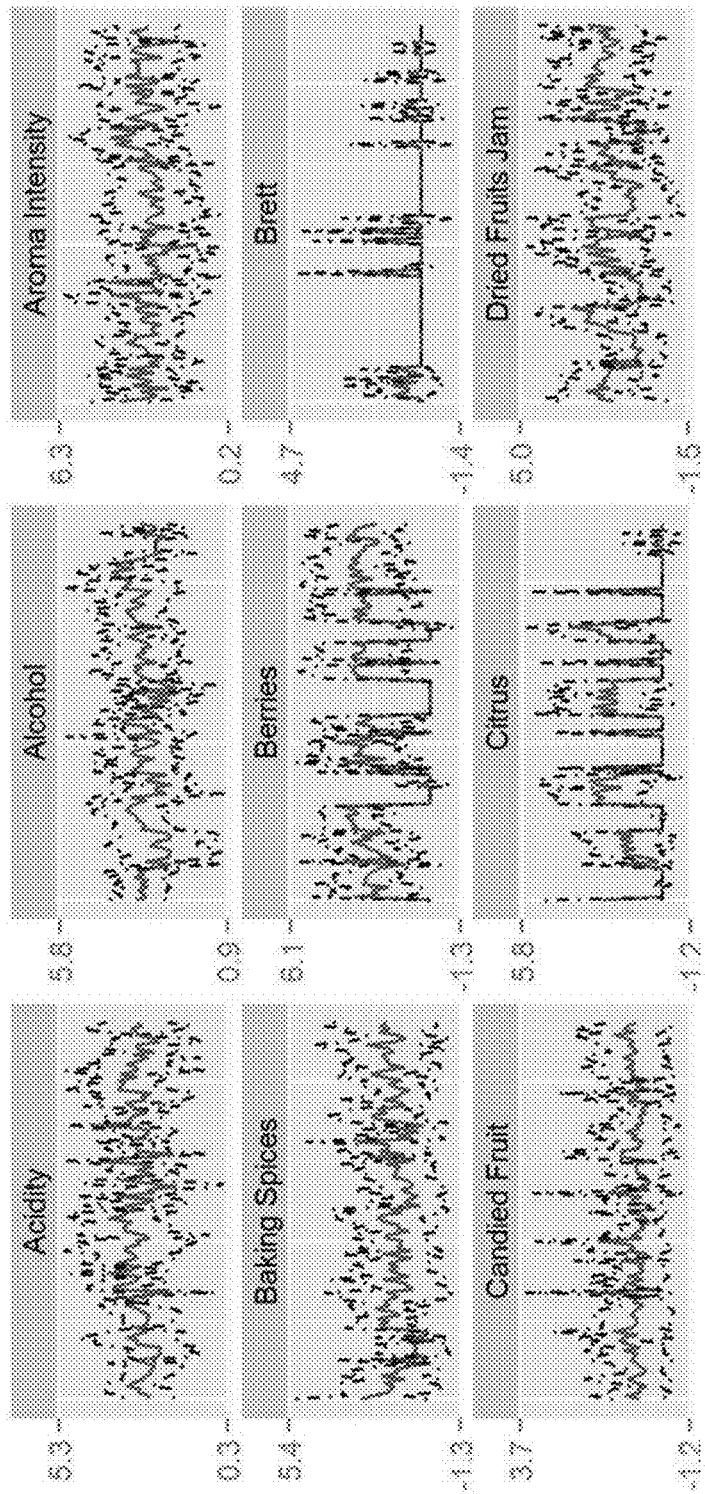
FIG. 32A depicts the results of wine ranking processing for a set of descriptor of wine, according to some embodiments.
Figure 32B:
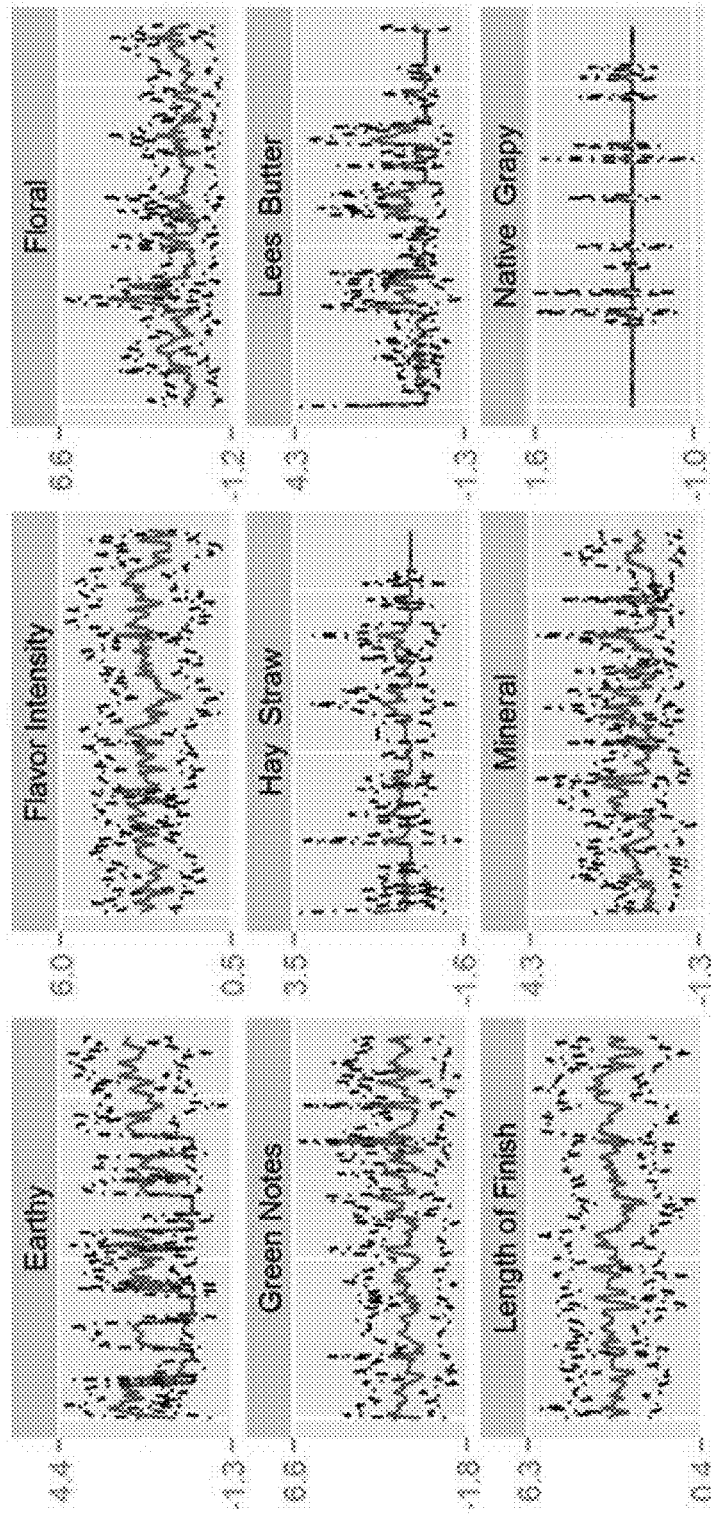
FIG. 32B depicts the results of wine ranking processing for a set of descriptor of wine, according to some embodiments.
Figure 32C:
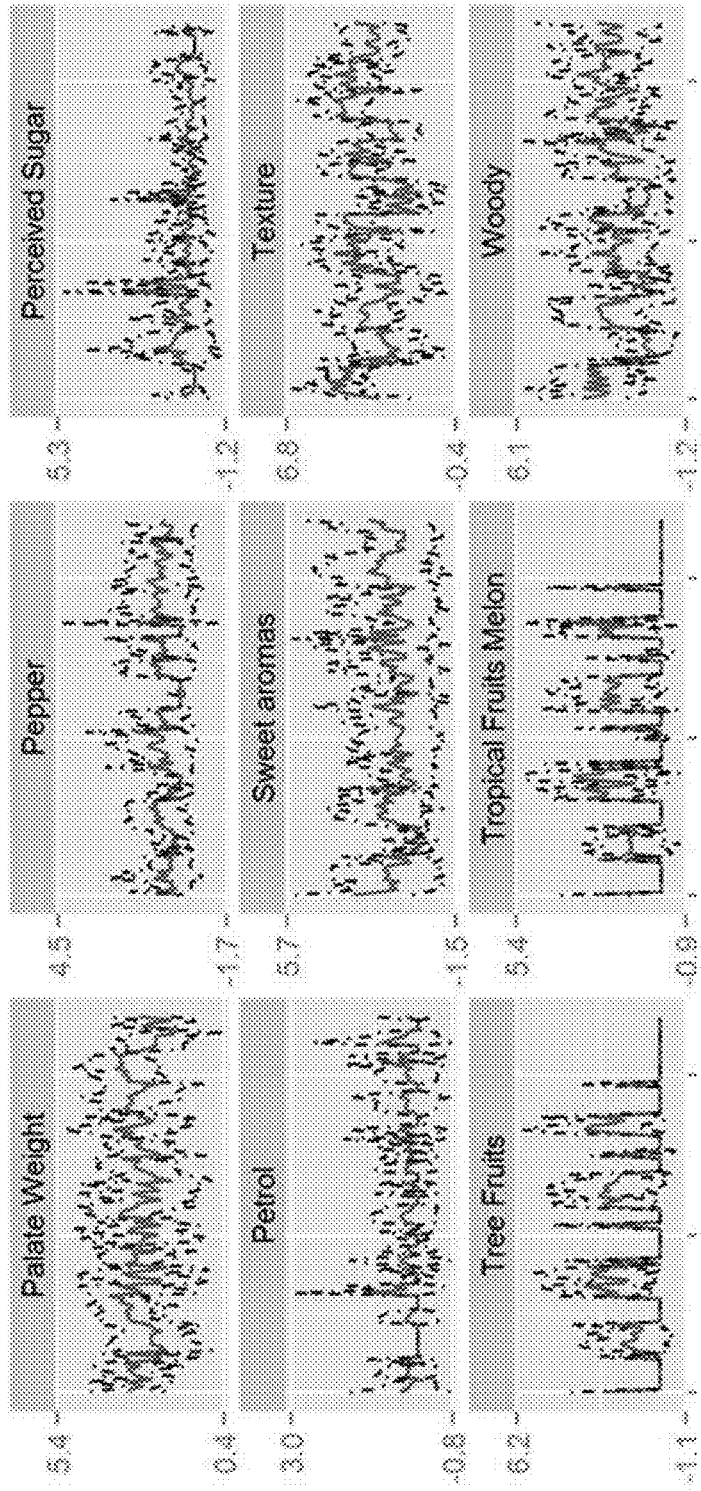
FIG. 32C depicts the results of wine ranking processing for a set of descriptor of wine, according to some embodiments.

FIG. 32A depicts the results of wine ranking processing for a set of descriptor of wine, according to some embodiments. FIG. 32B depicts the results of wine ranking processing for a set of descriptor of wine, according to some embodiments. FIG. 32C depicts the results of wine ranking processing for a set of descriptor of wine, according to some embodiments. The results shown in FIGS. 32A-32C exclude imprecise intensity values and outliers.

Figure 33A:
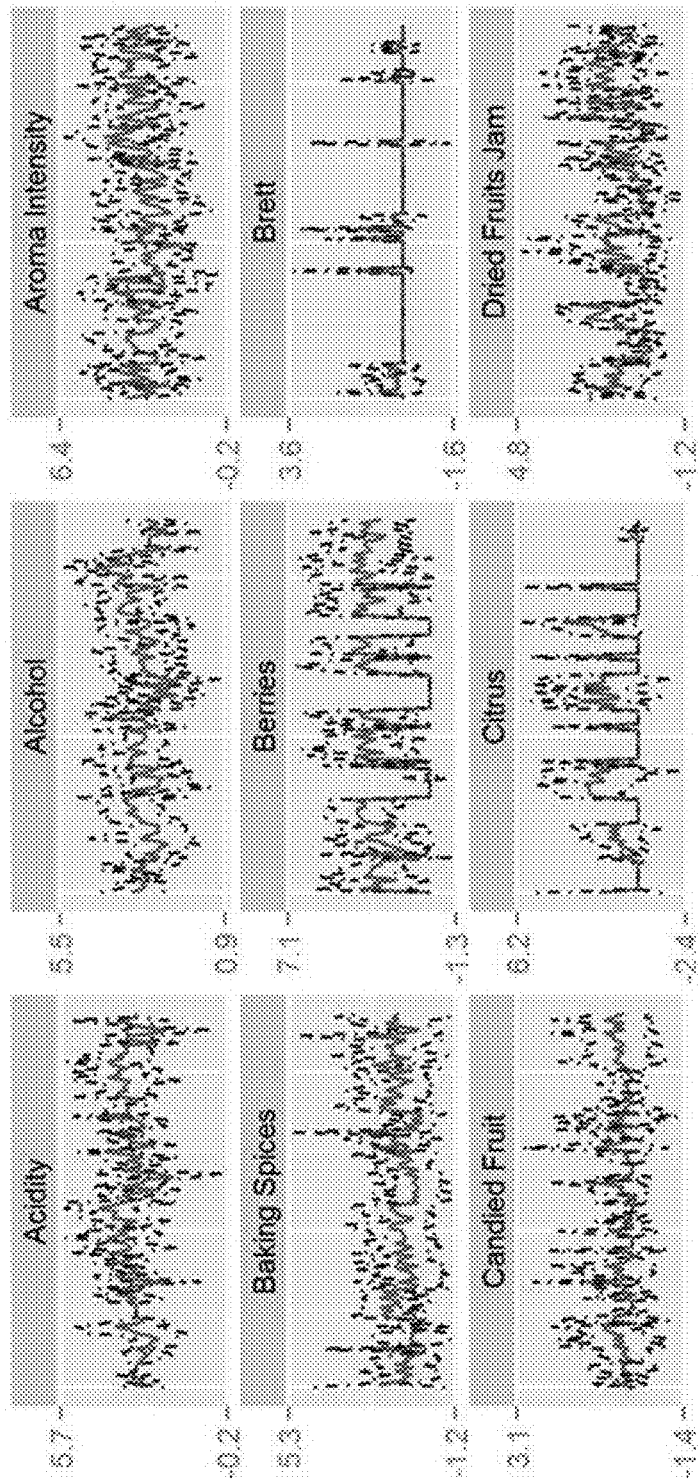
FIG. 33A depicts the results of wine ranking processing for a set of descriptor of wine, according to some embodiments.
Figure 33B:
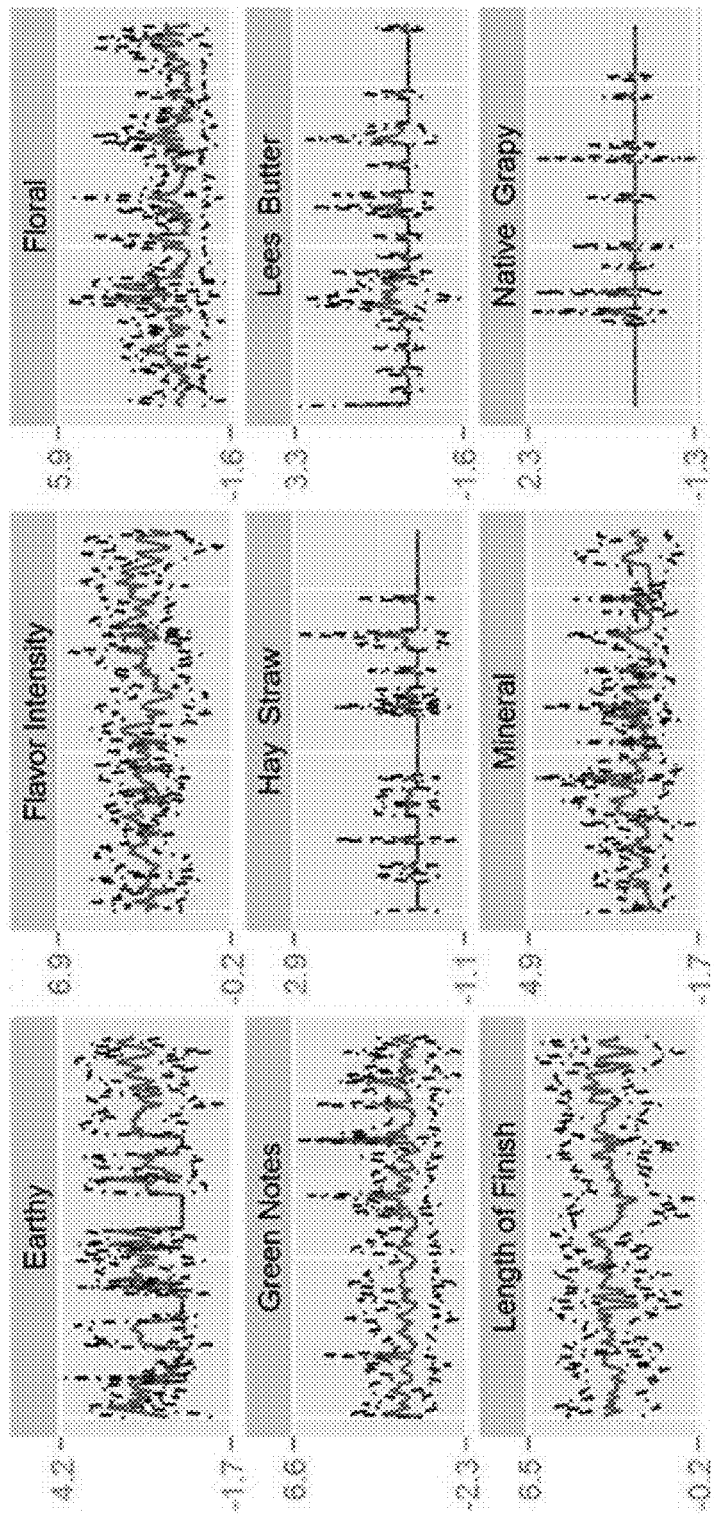
FIG. 33B depicts the results of wine ranking processing for a set of descriptor of wine, according to some embodiments.
Figure 33C:
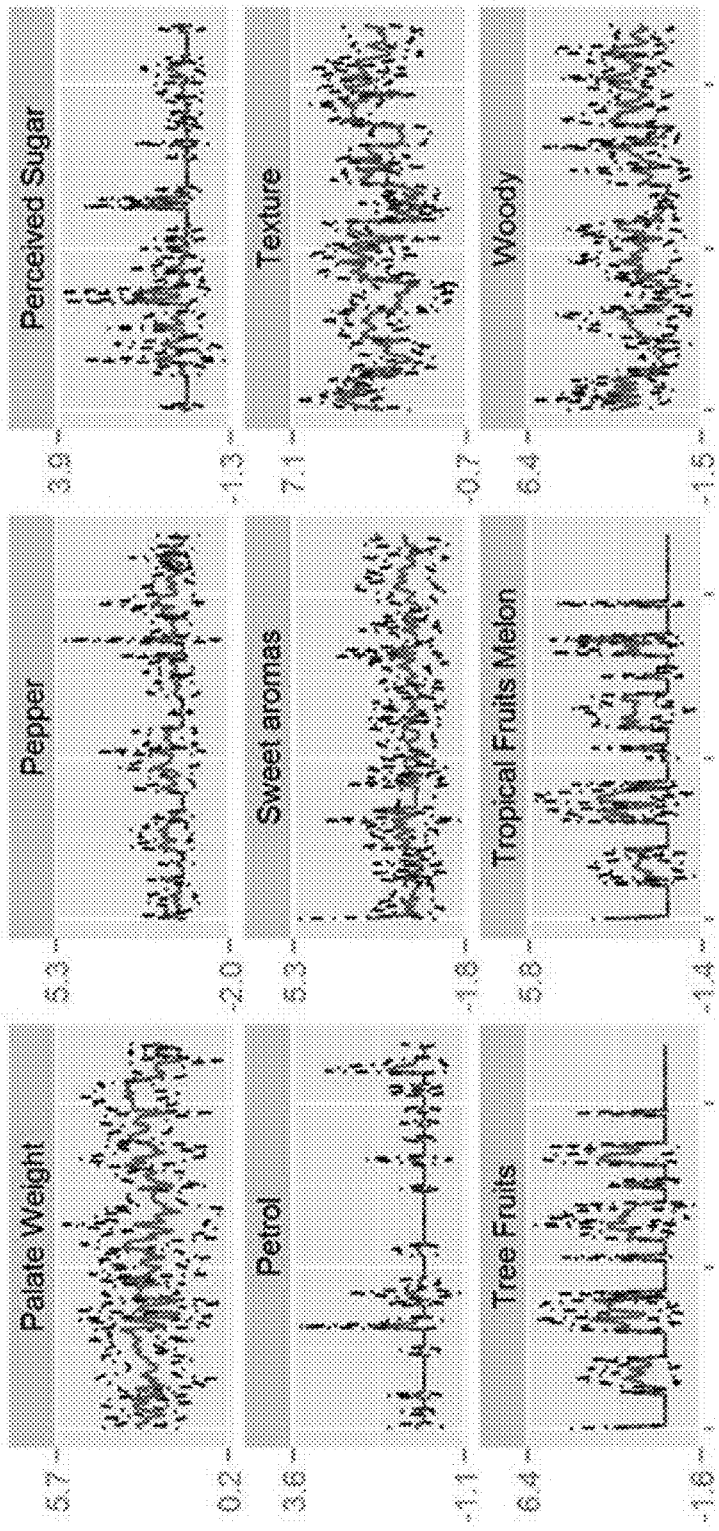
FIG. 33C depicts the results of wine ranking processing for a set of descriptor of wine, according to some embodiments.

FIG. 33A depicts the results of wine ranking processing for a set of descriptor of wine, according to some embodiments. FIG. 33B depicts the results of wine ranking processing for a set of descriptor of wine, according to some embodiments. FIG. 33C depicts the results of wine ranking processing for a set of descriptor of wine, according to some embodiments. The results shown in FIGS. 33A-33C exclude non-repeatable intensity values and outliers, and have grouped the intensity values that cluster together.

Figure 34A:
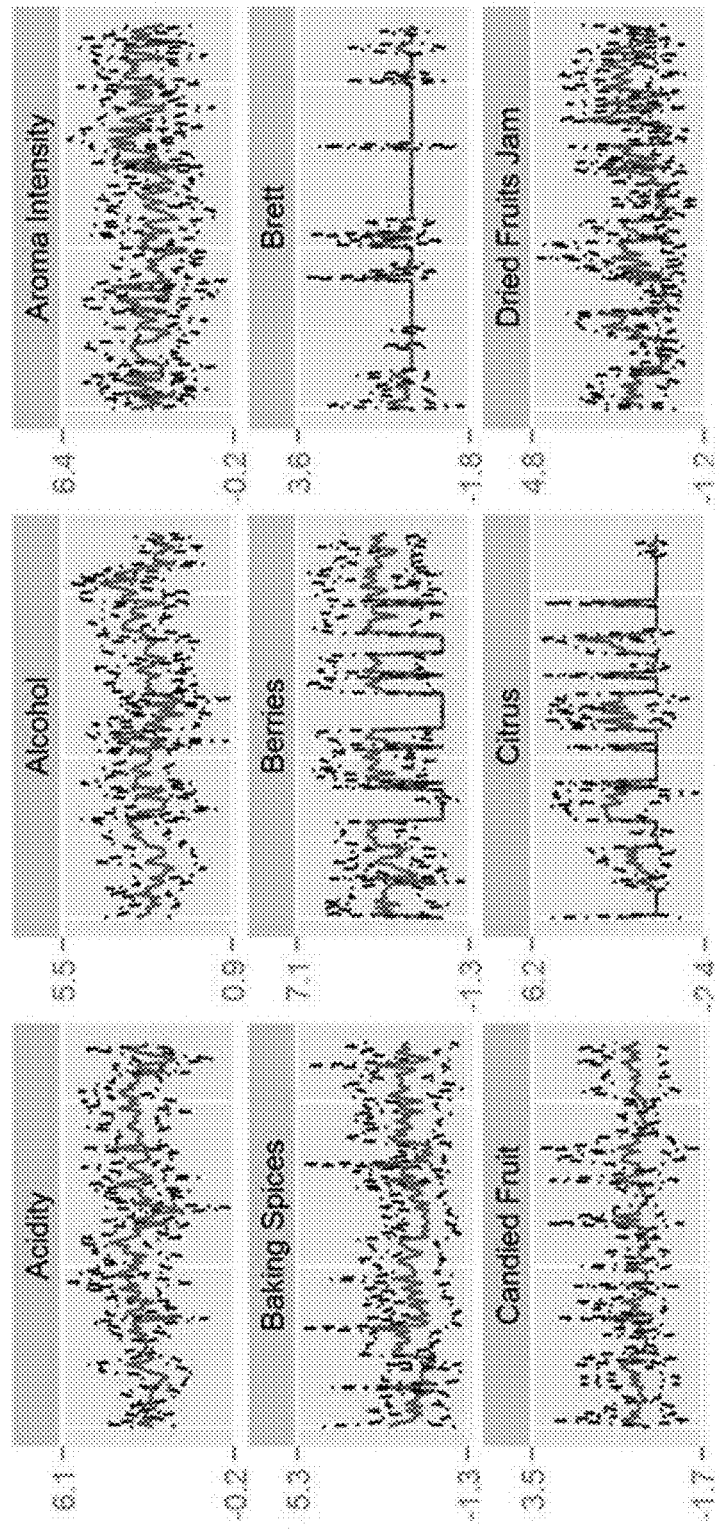
FIG. 34A depicts the results of wine ranking processing for a set of descriptor of wine, according to some embodiments.
Figure 34B:
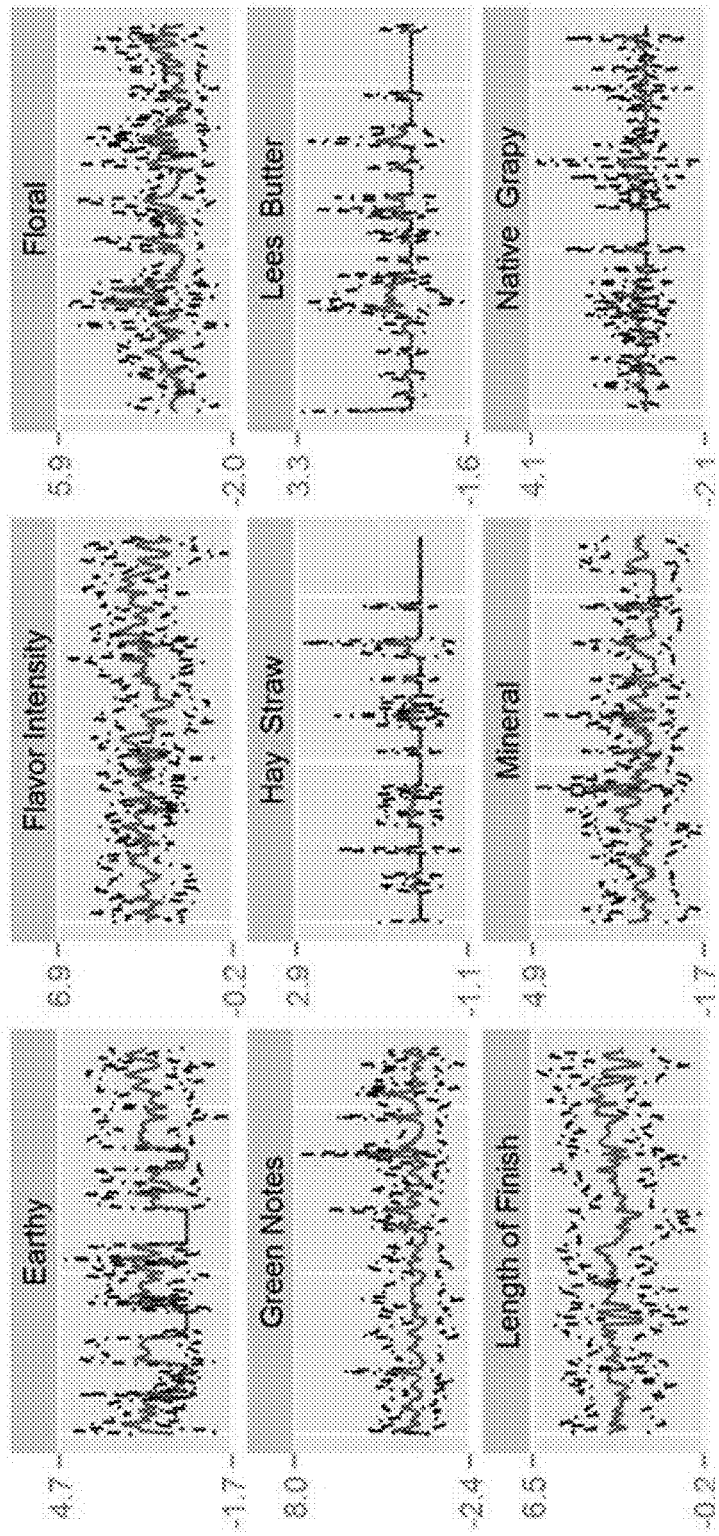
FIG. 34B depicts the results of wine ranking processing for a set of descriptor of wine, according to some embodiments.
Figure 34C:
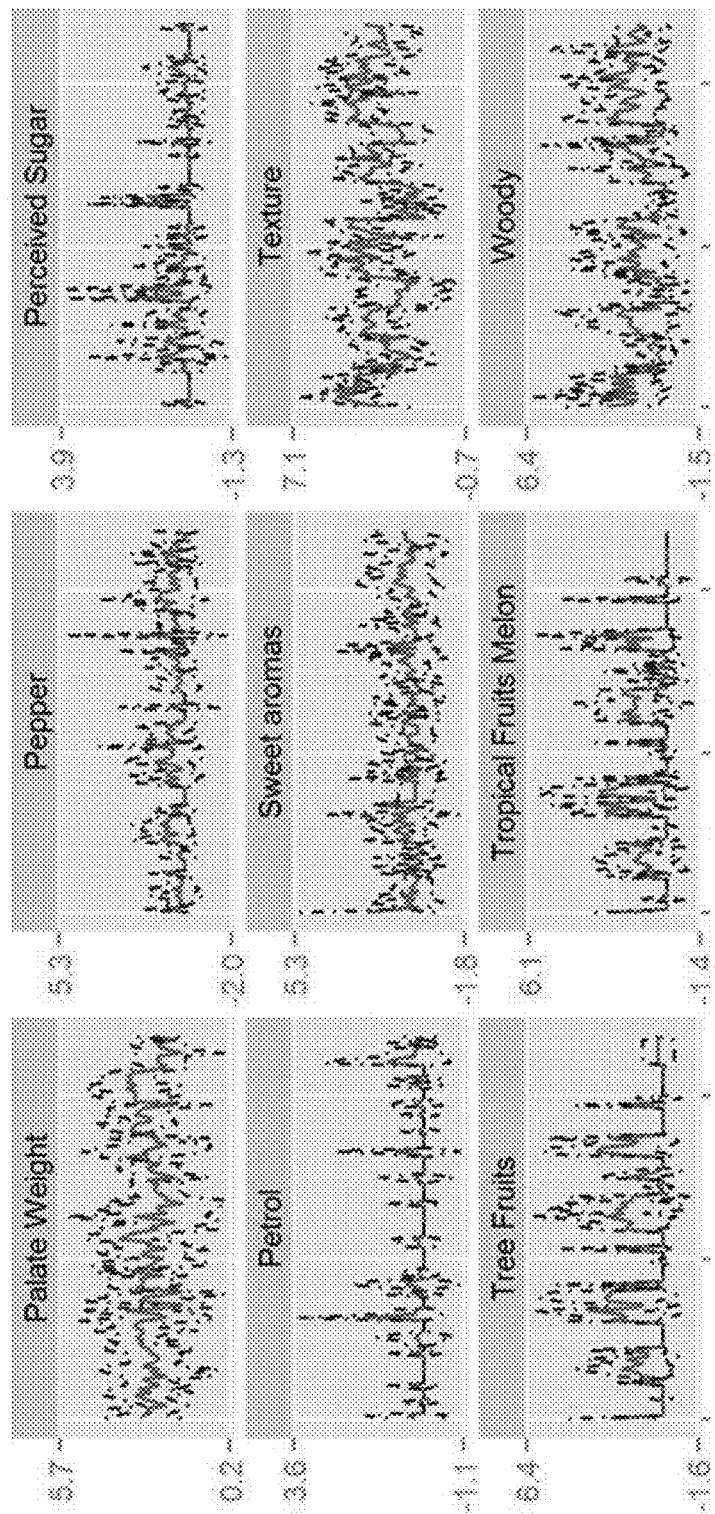
FIG. 34C depicts the results of wine ranking processing for a set of descriptor of wine, according to some embodiments.

FIG. 34A depicts the results of wine ranking processing for a set of descriptor of wine, according to some embodiments. FIG. 34B depicts the results of wine ranking processing for a set of descriptor of wine, according to some embodiments. FIG. 34C depicts the results of wine ranking processing for a set of descriptor of wine, according to some embodiments. The results shown in FIGS. 34A-34C exclude non-repeatable intensity values, and have grouped the intensity values that cluster together.

Figure 35A:
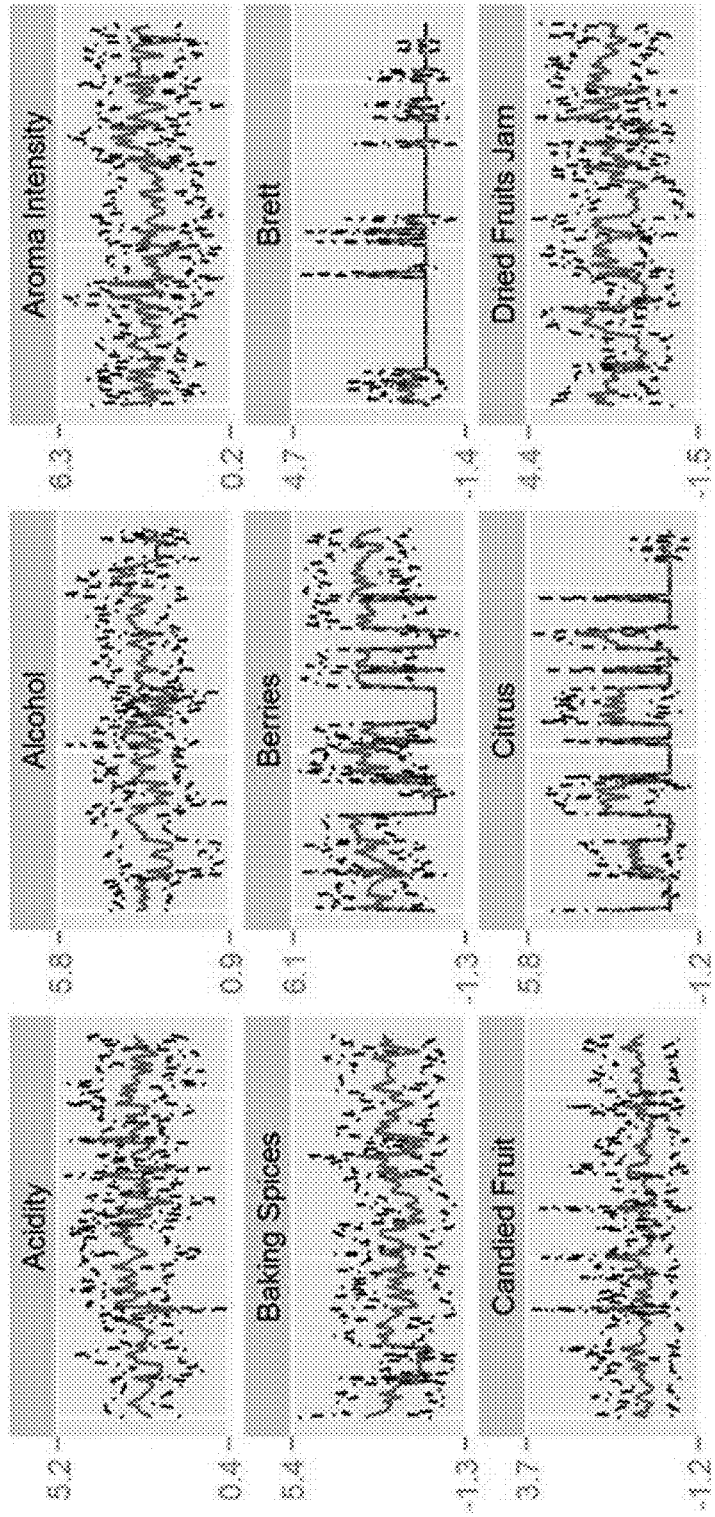
FIG. 35A depicts the results of wine ranking processing for a set of descriptor of wine, according to some embodiments.
Figure 35B:
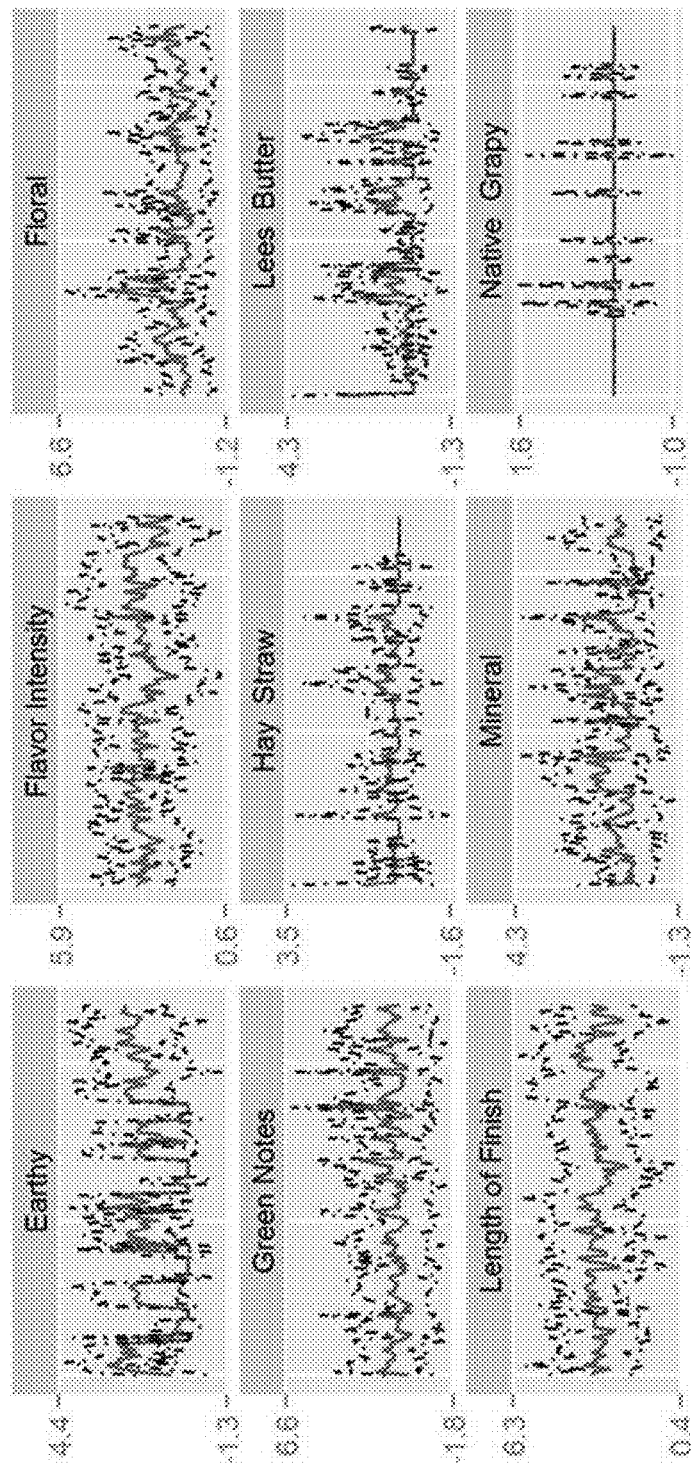
FIG. 35B depicts the results of wine ranking processing for a set of descriptor of wine, according to some embodiments.
Figure 35C:
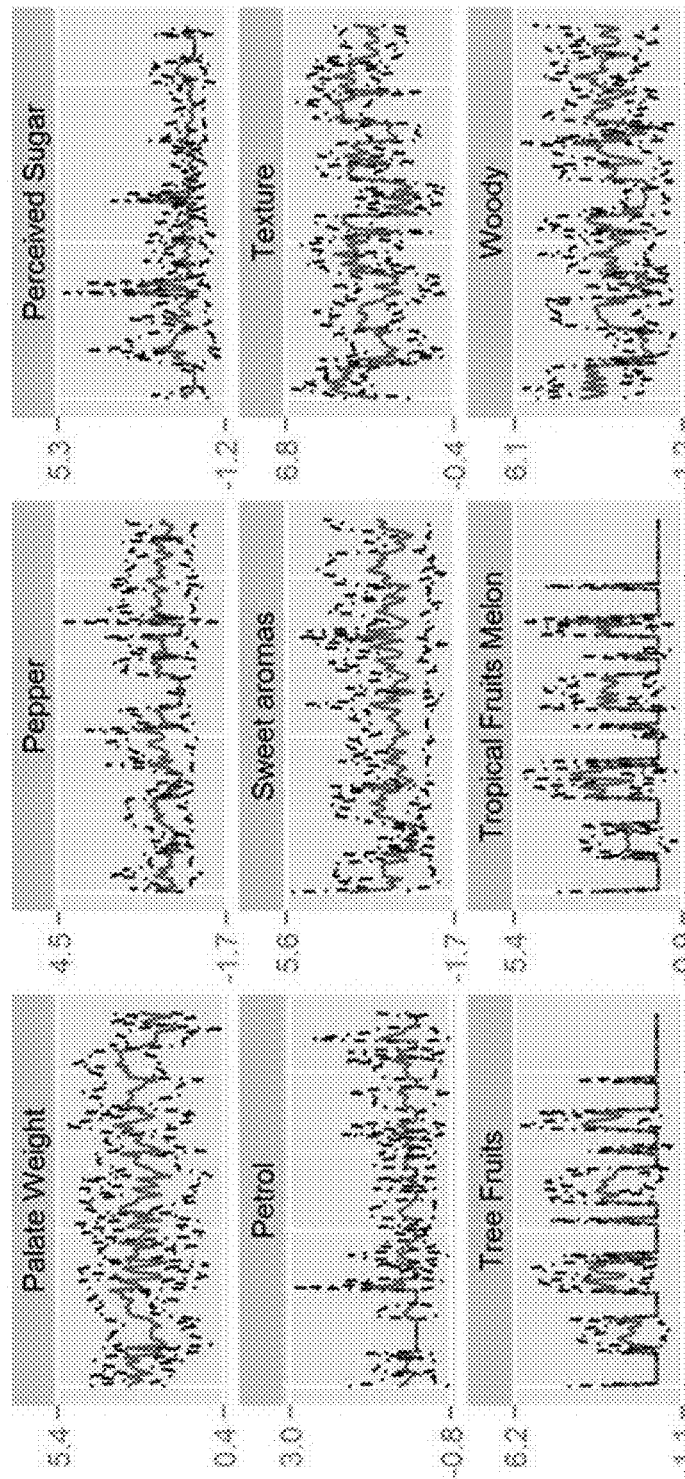
FIG. 35C depicts the results of wine ranking processing for a set of descriptor of wine, according to some embodiments.

FIG. 35A depicts the results of wine ranking processing for a set of descriptor of wine, according to some embodiments. FIG. 35B depicts the results of wine ranking processing for a set of descriptor of wine, according to some embodiments. FIG. 35C depicts the results of wine ranking processing for a set of descriptor of wine, according to some embodiments. The results shown in FIGS. 35A-35C exclude outliers.

Figure 36A:
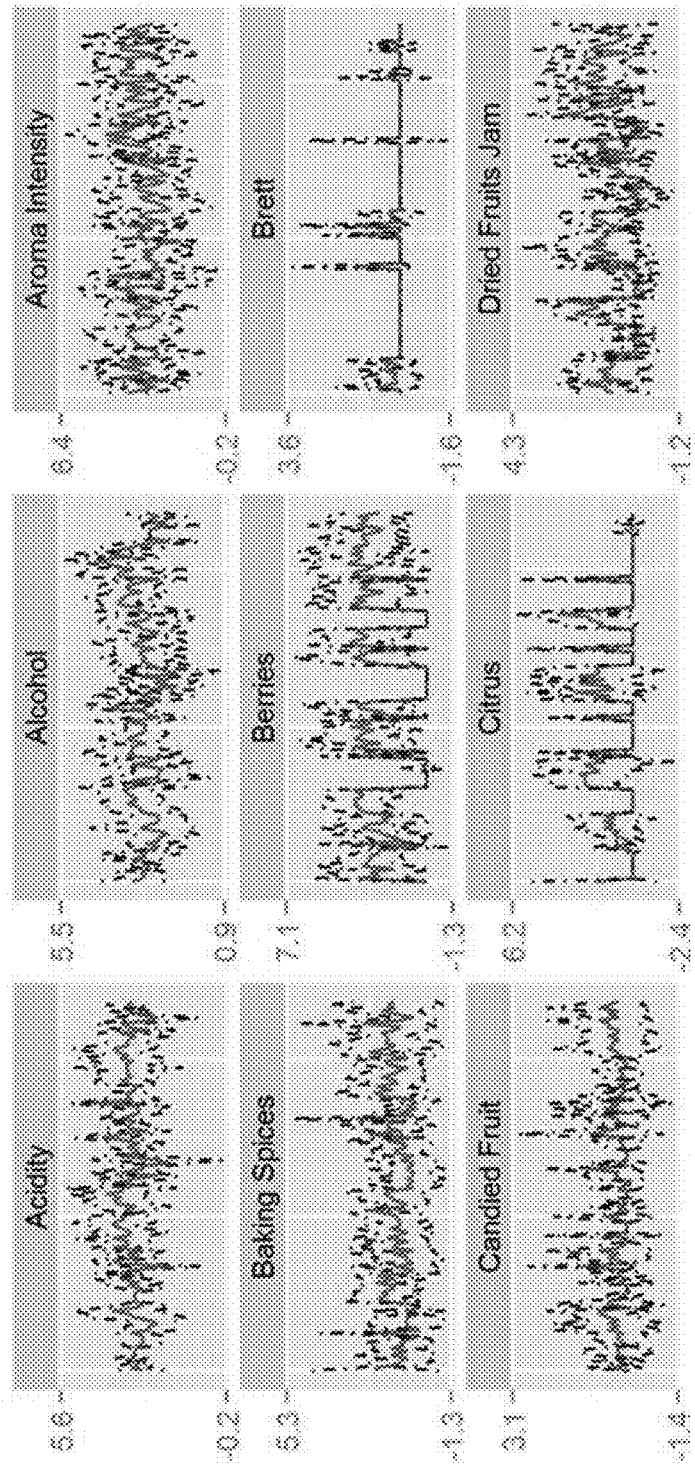
FIG. 36A depicts the results of wine ranking processing for a set of descriptor of wine, according to some embodiments.
Figure 36B:
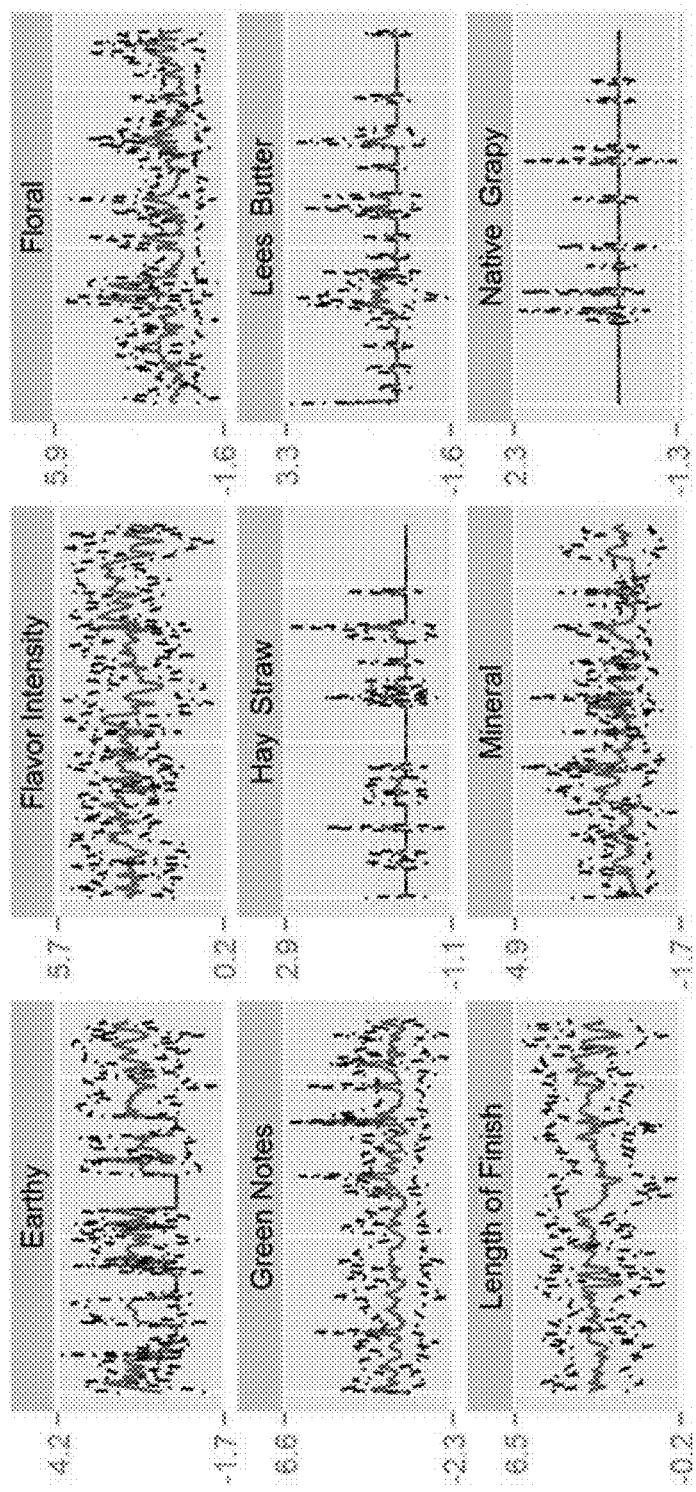
FIG. 36B depicts the results of wine ranking processing for a set of descriptor of wine, according to some embodiments.
Figure 36C:
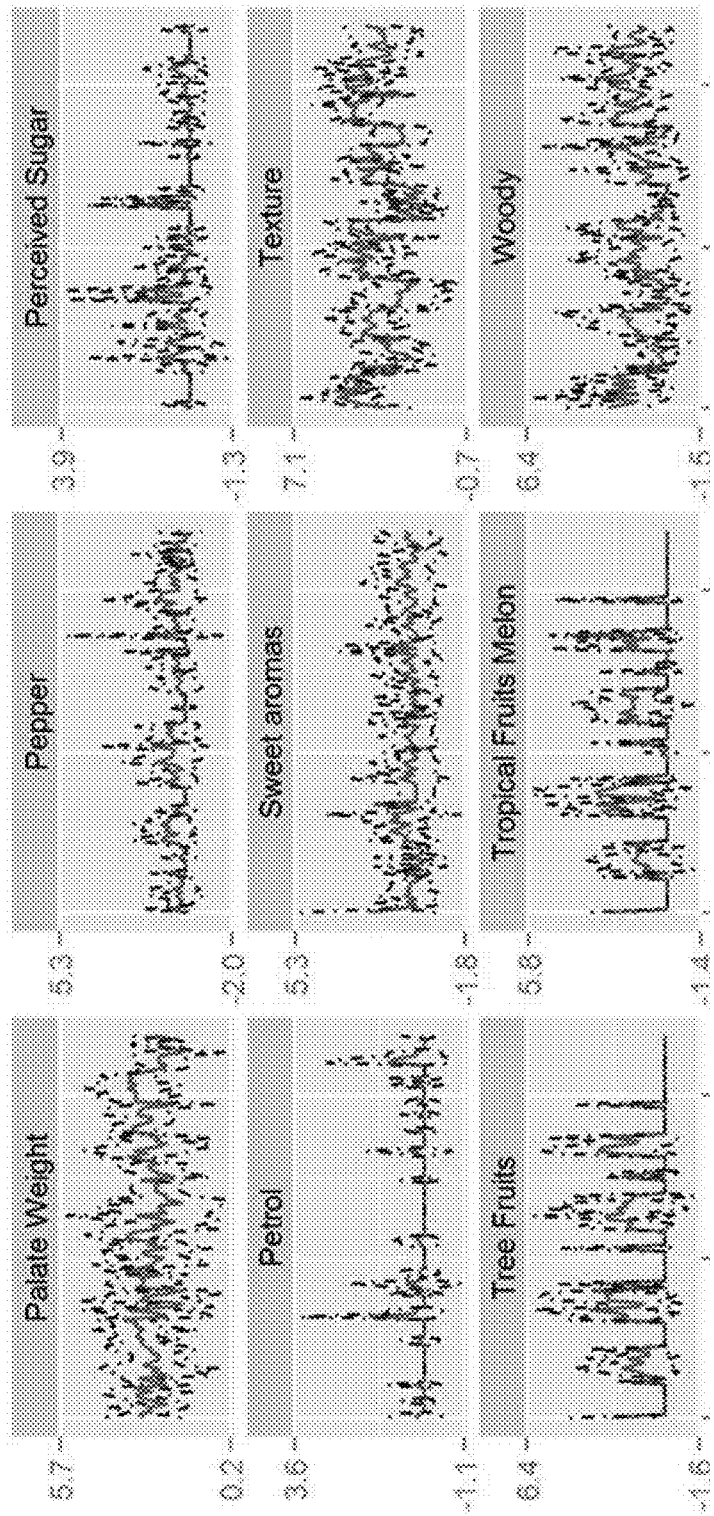
FIG. 36C depicts the results of wine ranking processing for a set of descriptor of wine, according to some embodiments.

FIG. 36A depicts the results of wine ranking processing for a set of descriptor of wine, according to some embodiments. FIG. 36B depicts the results of wine ranking processing for a set of descriptor of wine, according to some embodiments. FIG. 36C depicts the results of wine ranking processing for a set of descriptor of wine, according to some embodiments. The results shown in FIGS. 36A-36C exclude outliers, and have grouped the intensity values that cluster together.

Figure 37A:
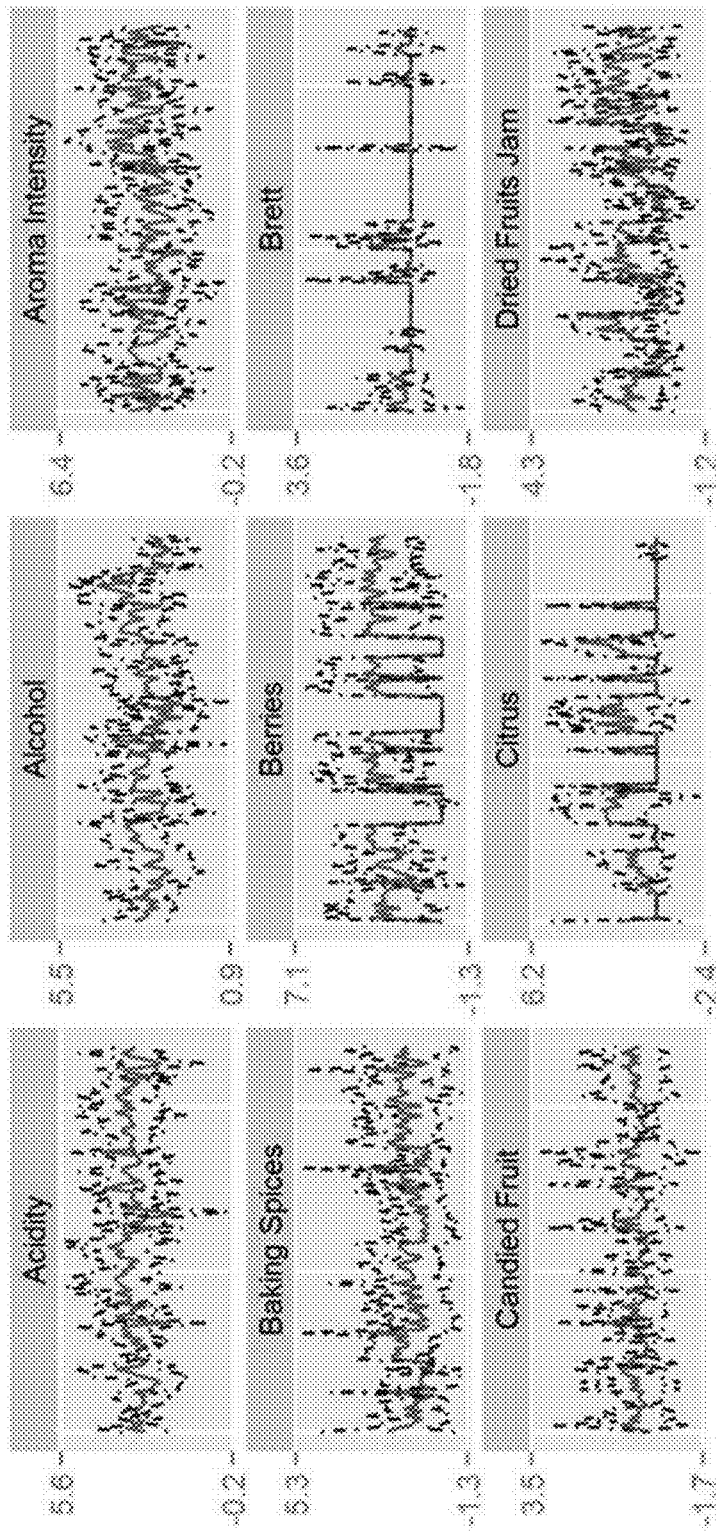
FIG. 37A depicts the results of wine ranking processing for a set of descriptor of wine, according to some embodiments.
Figure 37B:
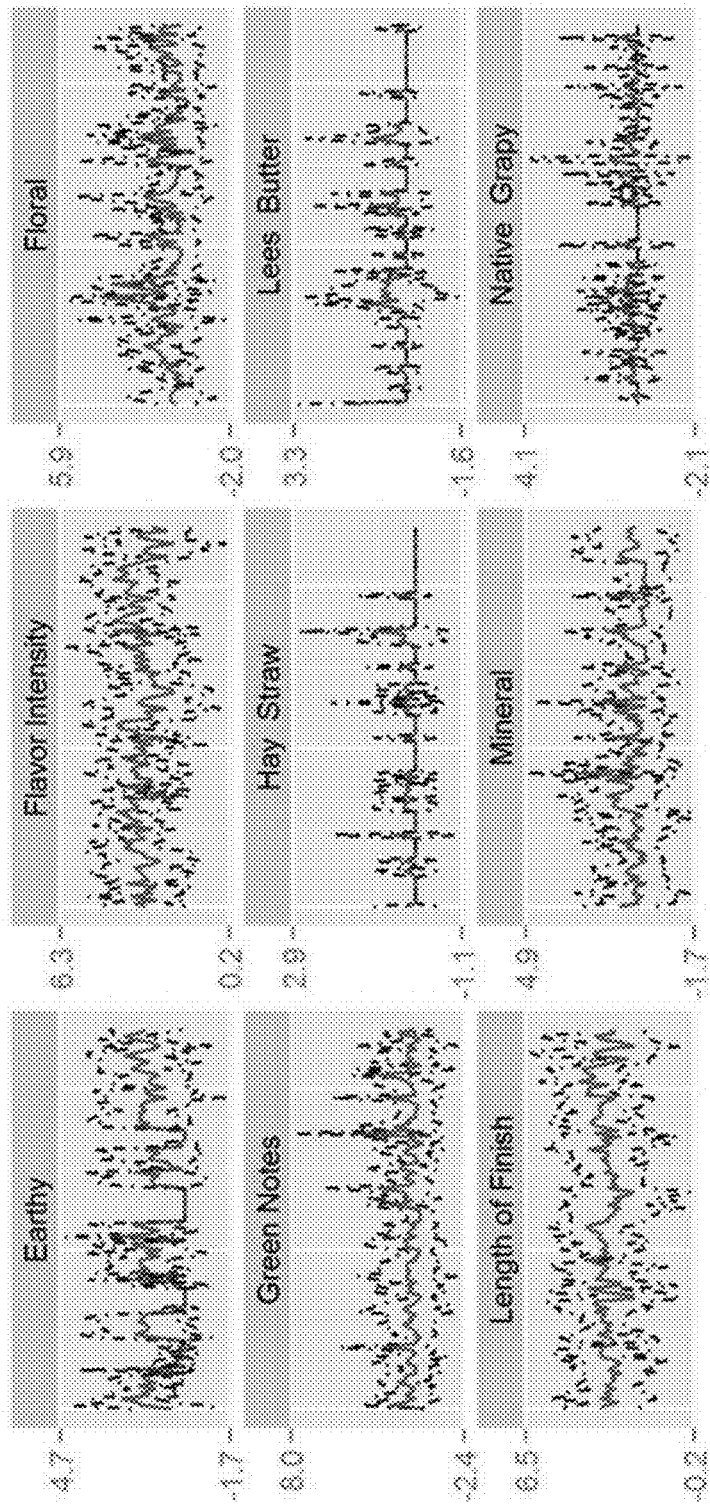
FIG. 37B depicts the results of wine ranking processing for a set of descriptor of wine, according to some embodiments.
Figure 37C:
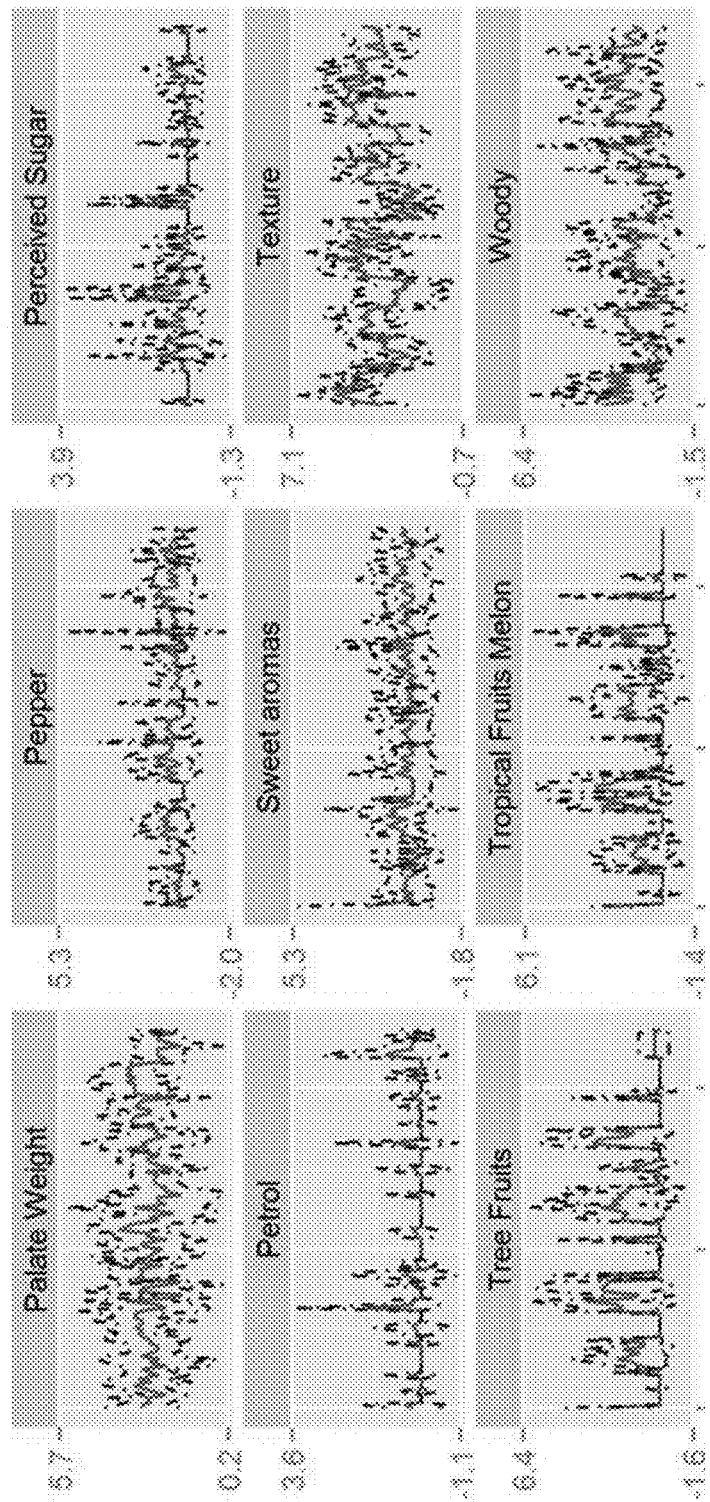
FIG. 37C depicts the results of wine ranking processing for a set of descriptor of wine, according to some embodiments.

FIG. 37A depicts the results of wine ranking processing for a set of descriptor of wine, according to some embodiments. FIG. 37B depicts the results of wine ranking processing for a set of descriptor of wine, according to some embodiments. FIG. 37C depicts the results of wine ranking processing for a set of descriptor of wine, according to some embodiments. The results shown in FIGS. 37A-37C include the full dataset, and have grouped the intensity values that cluster together.

Figure 38A:
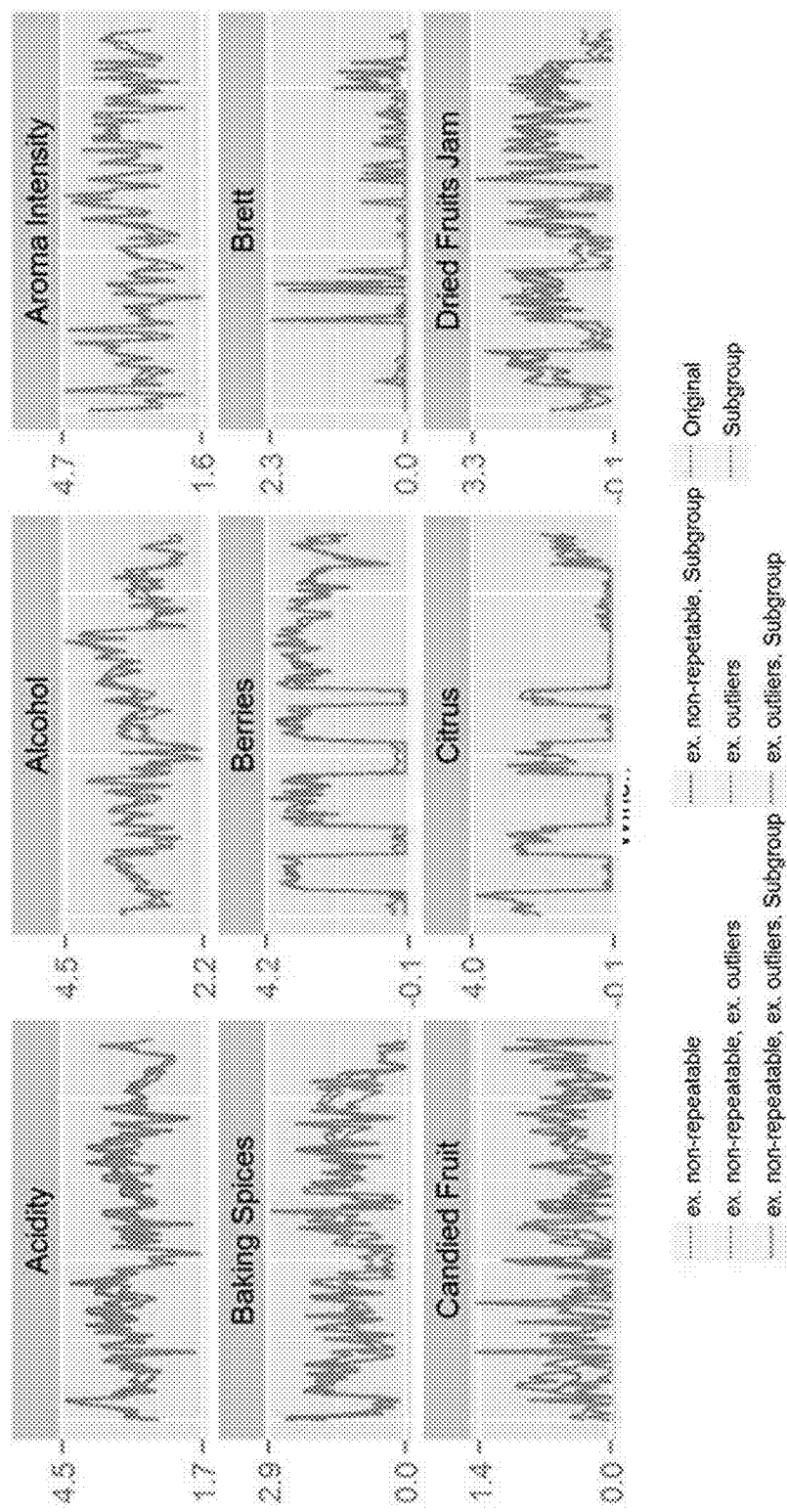
FIG. 38A depicts the results of wine ranking processing for a set of descriptor of wine, according to some embodiments.
Figure 38B:
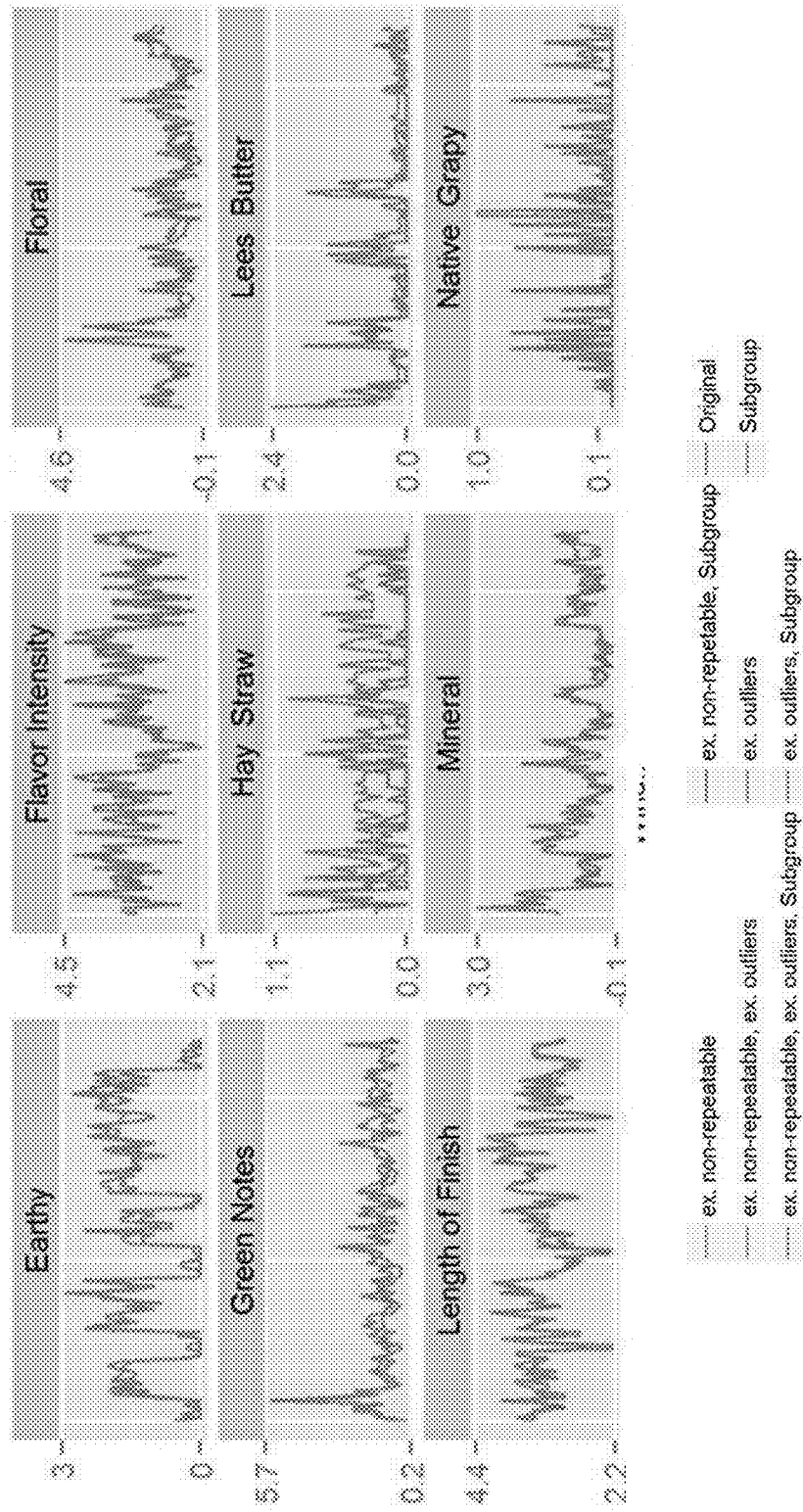
FIG. 38B depicts the results of wine ranking processing for a set of descriptor of wine, according to some embodiments.
Figure 38C:
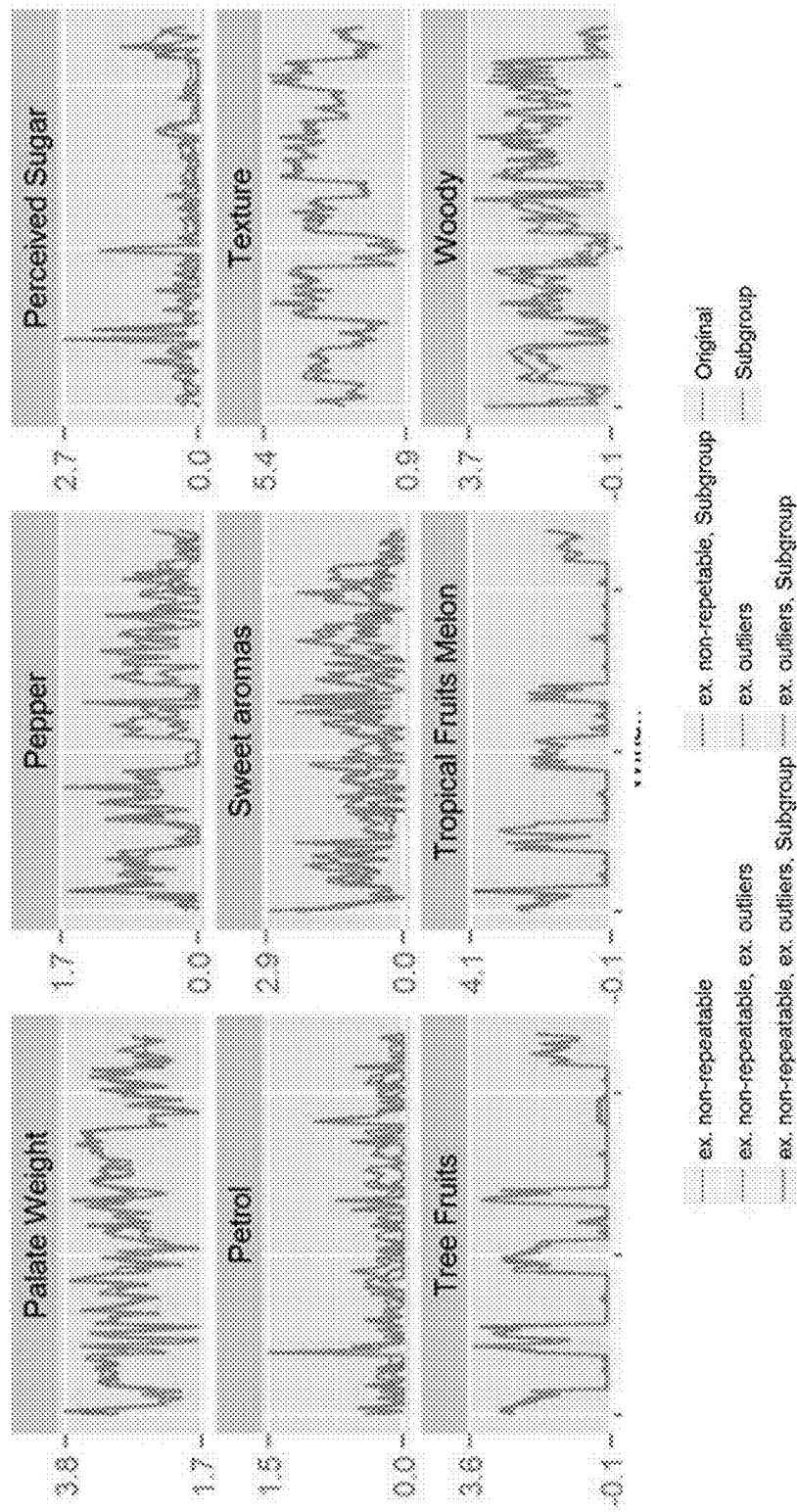
FIG. 38C depicts the results of wine ranking processing for a set of descriptor of wine, according to some embodiments.

FIG. 38A depicts the results of wine ranking processing for a set of descriptor of wine, according to some embodiments. FIG. 38B depicts the results of wine ranking processing for a set of descriptor of wine, according to some embodiments. FIG. 38C depicts the results of wine ranking processing for a set of descriptor of wine, according to some embodiments. In FIGS. 38A-38C, the red lines show the results of non-repeatable intensity values excluded; the yellow lines show the results of non-repeatable and outlier intensity values excluded; the lime green lines show the results of non-repeatable and outlier intensity values excluded with clusters grouped together; the forest green lines show the results of non-repeatable intensity values excluded with clusters grouped together; the light blue lines show the results of outliers excluded; the ocean green lines show the results of outlier intensity values excluded with clusters grouped together; the lavender lines show results of the full dataset; and the pink lines show the results with clusters grouped together.

FIG. 39 depicts an example of a wine score sheet for sensory evaluation, according to some embodiments. The wine score sheet comprises a Scantron® sheet that a panelist is to fill out. The wine score sheet has twenty-seven characteristics of wine that the panelist is asked to provide an intensity value between 0 to 6 for. The wine score sheet also has a write-in area for subjective evaluations and/or feedback. The wine score sheet also has a judge identification area to identify the panelist.

Figure 40:
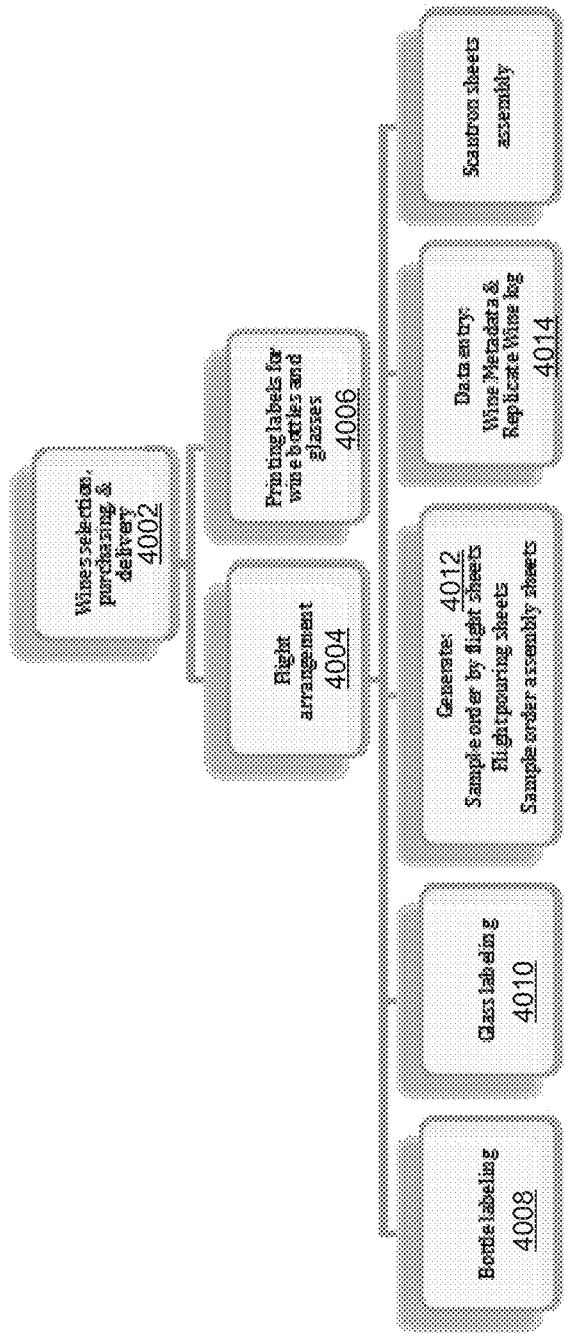
FIG. 40 depicts an example of a workflow for preparing wine panelists for tasting wines, according to some embodiments.

FIG. 40 depicts an example of a workflow process for preparing wine panelists for tasting wines, according to some embodiments. The work flow process may assist wine panelists in conduct a sensory evaluation of wines. At step 4002, wines are selected, purchased, and delivered to a wine panel. At step 4004, wine flights are arranged. At step 4006, labels are printed for wine bottles and glasses. At step 4008, bottles are labeled. At step 4010, glasses are labeled. At step 4012, a sample order by flight sheets, flight pouring sheets, and sample order assembly sheets are generated. At step 4014, data entry is performed; that is, wine metadata is gathered and a replicate wine log are entered. At step 4016, Scantron® sheets are assembled.

Figure 41:
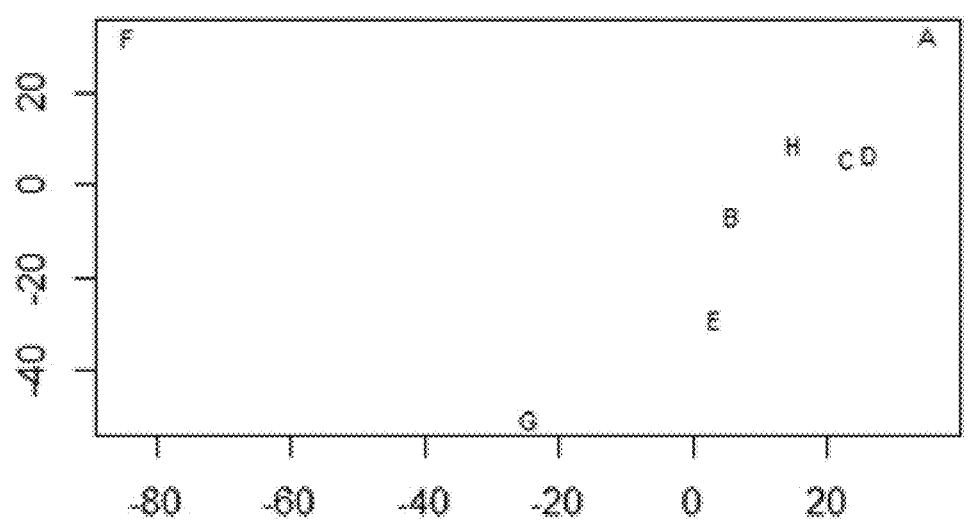
FIG. 41 depicts an example of multidimensional scaling of results from wine panelists, according to some embodiments.

FIG. 41 depicts an example of multidimensional scaling of results from wine panelists, according to some embodiments. The multidimensional scaling of the results in FIG. 41 shows relative panelist (A-H) grouping analysis based on multi-dimensional scaling of wine characteristic data. In this example, the panelists H, C, D, and B represent a close grouping that can be used as the basis for the global intensity value for a wine descriptor. The remaining panelists λ E, and G represent outliers whose intensity values need not be used as the global intensity value for the wine descriptor.

For purposes of explanation, numerous specific details are set forth in order to provide a thorough understanding of the description. It will be apparent, however, to one skilled in the art that embodiments of the disclosure can be practiced without these specific details. In some instances, modules, structures, processes, features, and devices are shown in block diagram form in order to avoid obscuring the description. In other instances, functional block diagrams and flow diagrams are shown to represent data and logic flows. The components of block diagrams and flow diagrams (e.g., modules, blocks, structures, devices, features, etc.) may be variously combined, separated, removed, reordered, and replaced in a manner other than as expressly described and depicted herein.

Reference in this specification to "one embodiment", "an embodiment", "other embodiments", "one series of embodiments", "some embodiments", "various embodiments", or the like means that a particular feature, design, structure, or characteristic described in connection with the embodiment is included in at least one embodiment of the disclosure. The appearances of, for example, the phrase "in one embodiment" or "in an embodiment" in various places in the specification are not necessarily all referring to the same embodiment, nor are separate or alternative embodiments mutually exclusive of other embodiments. Moreover, whether or not there is express reference to an "embodiment" or the like, various features are described, which may be variously combined and included in some embodiments, but also variously omitted in other embodiments. Similarly, various features are described that may be preferences or requirements for some embodiments, but not other embodiments. Moreover, the word "or" need not be construed using an exclusive OR operator, and may be construed as a non-exclusive OR (e.g., an "and/or").

The language used herein has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Various embodiments are described herein as examples. It will be apparent to those skilled in the art that various modifications may be made and other embodiments can be used without departing from the broader scope of the present invention. Therefore, these and other variations upon the exemplary embodiments are intended to be covered by the present invention.

The above-described functions and components may be comprised of instructions that are stored on a storage medium such as a non-transitory computer readable medium. The instructions may be retrieved and executed by a processor. Some examples of instructions are software, program code, and firmware. Some examples of storage medium are memory devices, tape, disks, integrated circuits, and servers. The instructions are operational when executed by the processor to direct the processor to operate in accord with some embodiments. Those skilled in the art are familiar with instructions, processor(s), and storage medium.

What is claimed is:

1. A system comprising:

at least one computer device with at least one processor;

at least one storage device configured to store wine evaluations from wine panelists, each wine evaluation generated by a respective wine panelist of the wine panelists, each wine evaluation including sets of intensity values for a set of wines, each set of intensity values describing a set of wine characteristics for each wine of the set of wines, each intensity value of the set of intensity values describing a particular wine characteristic of the set of wine characteristics, each set of intensity values from each wine panelist of the wine panelists including first intensity values describing the set of wine characteristics and second intensity values describing the set of wine characteristics for each of at least a few repeated wines of the set of wines;

a precision management module configured to be executed by the at least one processor to:

compare the first intensity values and the second intensity values from a particular wine panelist of the wine panelists for each of the at least a few repeated wines to determine precision deviations describing a particular wine characteristic of the set of wine characteristics, which includes to compare a particular first intensity value and a particular second intensity value describing the particular wine characteristic for a particular repeated wine of the set of wines to determine a particular precision deviation, evaluate each precision deviation to determine whether the first intensity value and the second intensity value describing the particular wine characteristic for each of the at least a few repeated wines are deemed imprecise, which includes to determine whether the particular first intensity value and the particular second intensity value describing the particular wine characteristic for the particular repeated wine are deemed imprecise, determine a quantity indicating how many of the first intensity values and the second intensity values from the particular wine panelist for the particular wine characteristic for the at least a few repeated wines are deemed imprecise, and determine based on the quantity whether the first intensity values and the second intensity values from the particular wine panelist describing the particular wine characteristic for a group of wines of the set of wines cannot be trusted; and a processing module configured to be executed by the at least one processor to:

if the precision management module determines that the first intensity values and the second intensity values from the particular wine panelist describing the particular wine characteristic for the group of wines of the set of wines cannot be trusted, generate global intensity values describing the particular wine characteristic for the group of wines by excluding the first intensity values and the second intensity values from the particular wine panelist describing the particular wine characteristic for the group of wines regardless of whether the first intensity values and the second intensity values for the particular wine characteristic for the group of wines are deemed imprecise, and if the precision management module does not determine that the first intensity values and the second intensity values from the particular wine panelist describing the particular wine characteristic for the group of wines cannot be trusted, generate a global intensity value for the particular wine characteristic for the particular repeated wine by excluding the particular first intensity value and the particular second intensity value from the particular wine panelist describing the particular wine characteristic for the particular repeated wine if the precision management module deemed the particular first intensity value and the particular second intensity value from the particular wine panelist describing the particular wine characteristic for the particular repeated wine imprecise.

2. The system of claim 1, wherein the wine evaluations are received from the wine panelists in response to a blind taste test.

3. The system of claim 2, wherein the blind taste test includes presenting a few repeated wines to the same wine panelist.

4. The system of claim 1, wherein the precision management module is further configured to determine that the particular first intensity value and the particular second intensity value are imprecise if they are a predetermined number of one or more standard deviations away.

5. The system of claim 1, further comprising:
 an engine configured to use the global intensity values to assist a user in selecting a particular wine; and
 an interface configured to present a recommendation for the particular wine to the user.

6. The system of claim 1,
 wherein the precision management module is further configured to be executed by the at least one processor to:
  compare the first intensity values and the second intensity values from the particular wine panelist for each of the at least a few repeated wines to determine precision deviations describing at least a few wine characteristics of the set of wine characteristics,
  evaluate each precision deviation to determine whether the first intensity value and the second intensity value describing the at least a few wine characteristics for each of the at least a few repeated wines are deemed imprecise,
  determine an indication of how many of the first intensity values and the second intensity values from the particular wine panelist for the at least a few wine characteristics for the at least a few repeated wines are deemed imprecise, and
  determine based on the indication whether the first intensity values and the second intensity values from the particular wine panelist for a group of wines of the set of wines cannot be trusted; and wherein the processing module is further configured to be executed by the at least one processor to:
  if the precision management module deemed that the first intensity values and the second intensity values from the particular wine panelist for the group of wines of the set of wines cannot be trusted, generate global intensity values describing the wine characteristics of the set of wine characteristics of the group of wines by excluding the first intensity values and the second intensity values generated by the selected wine panelist for the group of wines regardless of whether the first intensity values and the second intensity values for the group of wines are deemed imprecise.

7. A method by at least one processor, the method comprising:
 storing wine evaluations from wine panelists, each wine evaluation generated by a respective wine panelist of the wine panelists, each wine evaluation including sets of intensity values for a set of wines, each set of intensity values describing a set of wine characteristics for each wine of the set of wines, each intensity value of the set of intensity values describing a particular wine characteristic of the set of wine characteristics, each set of intensity values from each wine panelist of the wine panelists including first intensity values describing the set of wine characteristics and second intensity values describing the set of wine characteristics for each of at least a few repeated wines of the set of wines;
 comparing the first intensity values and the second intensity values from a particular wine panelist of the wine panelists for each of the at least a few repeated wines to determine precision deviations describing a particular wine characteristic of the set of wine characteristics, which includes comparing a particular first intensity value and a particular second intensity value describing the particular wine characteristic for a particular repeated wine of the set of wines to determine a particular precision deviation;
 evaluating each precision deviation to determine whether the first intensity value and the second intensity value describing the particular wine characteristic for each of the at least a few repeated wines are deemed imprecise, which includes to determine whether the particular first intensity value and the particular second intensity value describing the particular wine characteristic for the particular repeated wine are deemed imprecise;
 determining a quantity indicating how many of the first intensity values and the second intensity values from the particular wine panelist for the particular wine characteristic for the at least a few repeated wines are deemed imprecise;
 determining based on the quantity whether the first intensity values and the second intensity values from the particular wine panelist describing the particular wine characteristic for a group of wines of the set of wines cannot be trusted;
 if the precision management module determines that the first intensity values and the second intensity values from the particular wine panelist describing the particular wine characteristic for the group of wines of the set of wines cannot be trusted, generating global intensity values describing the particular wine characteristic for the group of wines by excluding the first intensity values and the second intensity values from the particular wine panelist describing the particular wine characteristic for the group of wines regardless of whether the first intensity values and the second intensity values for the particular wine characteristic for the group of wines are deemed imprecise;

if the precision management module does not determine that the first intensity values and the second intensity values from the particular wine panelist describing the particular wine characteristic for the group of wines cannot be trusted, generating a global intensity value for the particular wine characteristic for the particular repeated wine by excluding the particular first intensity value and the particular second intensity value from the particular wine panelist describing the particular wine characteristic for the particular repeated wine if the precision management module deemed the particular first intensity value and the particular second intensity value from the particular wine panelist describing the particular wine characteristic for the particular repeated wine imprecise; and storing the global intensity values.

8. The method of claim 7, further comprising receiving the wine evaluations from the wine panelists in response to a blind taste test.

9. The method of claim 8, wherein the blind taste test includes presenting a few repeated wines to the same wine panelist.

10. The method of claim 7, further comprising determining that the particular first intensity value and the particular second intensity value are imprecise if they are a predetermined number of one or more standard deviations away.

11. The method of claim 7, further comprising:

using the global intensity values to assist a user in selecting a particular wine; and presenting a recommendation for the particular wine to the user.

12. The method of claim 7, further comprising:

comparing the first intensity values and the second intensity values from the particular wine panelist for each of the at least a few repeated wines to determine precision deviations describing at least a few wine characteristics of the set of wine characteristics;

evaluating each precision deviation to determine whether the first intensity value and the second intensity value describing the at least a few wine characteristics for each of the at least a few repeated wines are deemed imprecise;

determining an indication of how many of the first intensity values and the second intensity values from the particular wine panelist for the at least a few wine characteristics for the at least a few repeated wines are deemed imprecise;

determining based on the indication whether the first intensity values and the second intensity values from the particular wine panelist for a group of wines of the set of wines cannot be trusted;

if the precision management module deemed that the first intensity values and the second intensity values from the particular wine panelist for the group of wines of the set of wines cannot be trusted, generating global intensity values describing the wine characteristics of the set of wine characteristics of the group of wines by excluding the first intensity values and the second intensity values generated by the selected wine panelist for the group of wines regardless of whether the first intensity values and the second intensity values for the group of wines are deemed imprecise.

\* \* \* \* \*